(12) United States Patent
Ouchi et al.

(10) Patent No.: US 8,865,731 B2
(45) Date of Patent: Oct. 21, 2014

(54) INHIBITOR OF ANALGESIC TOLERANCE

(75) Inventors: Jun Ouchi, Shizuoka (JP); Shunji Kunori, Shizuoka (JP); Yozo Kojima, Shizuoka (JP); Katsumi Shinoda, Tokyo (JP); Katsutoshi Sasaki, Shizuoka (JP); Shiro Shirakura, Shizuoka (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 473 days.

(21) Appl. No.: 12/994,923

(22) PCT Filed: May 29, 2009

(86) PCT No.: PCT/JP2009/059845
§ 371 (c)(1),
(2), (4) Date: Jan. 3, 2011

(87) PCT Pub. No.: WO2009/145289
PCT Pub. Date: Dec. 3, 2009

(65) Prior Publication Data
US 2011/0105465 A1    May 5, 2011

(30) Foreign Application Priority Data

May 29, 2008 (JP) ................................. 2008-141178
Nov. 27, 2008 (JP) ................................. 2008-302783

(51) Int. Cl.
| | | |
|---|---|---|
| A01N 43/90 | (2006.01) | |
| A61K 31/522 | (2006.01) | |
| A61K 31/52 | (2006.01) | |
| A01N 43/64 | (2006.01) | |
| A61K 31/41 | (2006.01) | |
| A01N 43/78 | (2006.01) | |
| A61K 31/425 | (2006.01) | |
| A01N 43/54 | (2006.01) | |
| A61K 31/517 | (2006.01) | |
| A61K 31/519 | (2006.01) | |
| C07D 471/04 | (2006.01) | |
| C07D 471/22 | (2006.01) | |
| C07D 487/04 | (2006.01) | |
| C07D 473/00 | (2006.01) | |
| C07D 273/00 | (2006.01) | |
| C07D 239/02 | (2006.01) | |
| C07D 249/16 | (2006.01) | |
| C07D 403/00 | (2006.01) | |
| A61K 31/4439 | (2006.01) | |
| C07D 473/34 | (2006.01) | |
| C07D 473/06 | (2006.01) | |
| C07D 487/14 | (2006.01) | |
| C07D 417/04 | (2006.01) | |
| C07D 417/14 | (2006.01) | |
| A61K 31/506 | (2006.01) | |
| A61K 45/06 | (2006.01) | |
| A61K 31/343 | (2006.01) | |
| A61K 31/427 | (2006.01) | |
| A61K 31/485 | (2006.01) | |

(52) U.S. Cl.
CPC ............ *C07D 417/14* (2013.01); *A61K 31/522* (2013.01); *A61K 31/4439* (2013.01); *C07D 473/34* (2013.01); *C07D 473/06* (2013.01); *C07D 487/14* (2013.01); *C07D 417/04* (2013.01); *A61K 31/506* (2013.01); *A61K 45/06* (2013.01); *A61K 31/343* (2013.01); *C07D 487/04* (2013.01); *A61K 31/52* (2013.01); *A61K 31/427* (2013.01); *A61K 31/519* (2013.01); *A61K 31/485* (2013.01)
USPC .................. 514/263.34; 514/263.1; 514/359; 514/365; 514/258.1; 514/257; 544/267; 544/264; 544/317; 548/257

(58) Field of Classification Search
USPC ................. 514/263.34, 257, 258.1, 365, 264, 514/263.1, 359; 544/267, 264, 317; 548/257
See application file for complete search history.

(56) References Cited

U.S. PATENT DOCUMENTS

| | | | |
|---|---|---|---|
| 5,587,378 A | 12/1996 | Suzuki et al. | |
| 6,545,000 B1 | 4/2003 | Shimada et al. | |
| 6,630,475 B2 | 10/2003 | Neustadt et al. | |
| 7,141,575 B2 | 11/2006 | Gillespie et al. | |
| 7,189,717 B2 | 3/2007 | Yasuda et al. | |

(Continued)

FOREIGN PATENT DOCUMENTS

| | | |
|---|---|---|
| JP | 2003-201254 | 7/2003 |
| WO | 99/13799 | 3/1999 |

(Continued)

OTHER PUBLICATIONS

Yao et al. "Adenosine A2a blockade prevents synergy between mu-opiate and cannabinoid CB1 receptors and eliminates heroin-seeking behaviro in addicted rats" Proc Natl Acad Sci, May 2006, vol. 103, No. 20, pp. 7877-7882.*

(Continued)

*Primary Examiner* — Kendra D Carter
(74) *Attorney, Agent, or Firm* — Fitzpatrick, Cella, Harper & Scinto

(57) ABSTRACT

Provided are: an agent for suppressing an undesirable effect of an opioid-type analgesic (opioid), which comprises a compound having adenosine $A_{2A}$ receptor antagonistic activity or a pharmaceutically acceptable salt thereof as an active ingredient; the agent for suppressing an undesirable effect of an opioid-type analgesic (opioid), wherein the undesirable effect of the opioid-type analgesic (opioid) is analgesic tolerance or constipation; the agent for suppressing an undesirable effect of an opioid-type analgesic (opioid), wherein the undesirable effect of the opioid-type analgesic (opioid) is analgesic tolerance; and the like.

12 Claims, 1 Drawing Sheet

(56) References Cited

U.S. PATENT DOCUMENTS

| | | | |
|---|---|---|---|
| 7,230,102 | B2 | 6/2007 | Giorgio et al. |
| 7,384,949 | B2 | 6/2008 | Gillespie et al. |
| 7,718,808 | B2 | 5/2010 | Nakajima et al. |
| 2002/0099049 | A1 | 7/2002 | Burch et al. |
| 2002/0099061 | A1 | 7/2002 | Neustadt et al. |
| 2004/0097526 | A1 | 5/2004 | Gillespie et al. |
| 2004/0138235 | A1 | 7/2004 | Grzelak et al. |
| 2006/0106040 | A1 | 5/2006 | Grzelak et al. |
| 2006/0128694 | A1 | 6/2006 | Grzelak et al. |
| 2006/0128708 | A1 | 6/2006 | Diamond et al. |
| 2007/0105919 | A1 | 5/2007 | Nakajima et al. |
| 2007/0149555 | A1 | 6/2007 | Kase et al. |
| 2007/0249638 | A1 | 10/2007 | Giorgio et al. |
| 2008/0153820 | A1 | 6/2008 | Gillespie et al. |
| 2009/0137642 | A1 | 5/2009 | Larsen et al. |

FOREIGN PATENT DOCUMENTS

| | | |
|---|---|---|
| WO | 00/17201 | 3/2000 |
| WO | 01/80893 | 11/2001 |
| WO | 01/92264 | 12/2001 |
| WO | 02/055083 | 7/2002 |
| WO | 02/055524 | 7/2002 |
| WO | 03/011864 | 2/2003 |
| WO | 03/099289 | 12/2003 |
| WO | 2005/063743 | 7/2005 |
| WO | 2005/094885 | 10/2005 |
| WO | 2006/009698 | 1/2006 |
| WO | 2006/032273 | 3/2006 |
| WO | 2006/059713 | 6/2006 |
| WO | 2007/038212 | 4/2007 |
| WO | 2007/047293 | 4/2007 |
| WO | 2007/103776 | 9/2007 |
| WO | 2008/070529 | 6/2008 |

OTHER PUBLICATIONS

Hojsted et al. "Addiction to opioids in chronic pain patients: A literature review" European Journal of Pain, Jul. 2007, vol. 11, issue 5, pp. 490-518.*
Benyamine et al. "Opioid Complications and Side Effects" Pain Physician 2008: Opioid Special Issue, 2008, vol. 111, pp. S105-S120.*
Eddy et al. "Drug Dependence: its significance and characteristics" Bull. World Health Organ., 1965, vol. 32, No. 5, pp. 721-733.*
Glare et al. "Unrecognized constipation in patients with advanced cancer: A recipe for therapeutic disaster" Journal of Pain and Symptom Management, 1992, vol. 7, issue 6, pp. 369-371, abstract provided.*
Abdel-Zaher, et al, "Attenuation of morphine tolerance and dependence by aminoguanidine in mice", European Journal of Pharmacology, vol. 540 (2006) 60-6.
Ackley, et al., "Adenosine contributes to μ-opioid synaptic inhibition in rat substantia gelatinosa in vitro", Neuroscience Letters, vol. 376 (2005) 102-6.
Katz, et al., "Treatment of osteoarthritis pain with extended-release morphine sulfate plus sequestered naltrexone", Anesthesiology, vol. 107 (2007) A1370.
Bailey, et al., "Quantitative autoradiography of adenosine receptors and NBTI-sensitive adenosine transporters in the brains and spinal cords of mice deficient in the μ-opioid receptor gene", Brain Research, vol. 943 (2002) 68-79.
Bailey, et al., "Changes in Spinal δ and κ Opioid Systems in Mice Deficient in the A2A Receptor Gene", The Journal of Neuroscience, vol. 22, No. 21 (2002) 9210-20.
Chang, et al., "Opioid Tolerance and Hyperalgesia", Med Clin N Am, vol. 91 (2007) 199-211.
Chindalore, et al., "Adding Ultralow-Dose Naltrexone to Oxycodone Enhances and Prolongs Analgesia: A Randomized, Controlled Trial of Oxytrex", The Journal of Pain, vol. 6, No. 6 (2005) 392-99.
Ferré, et al., "Adenosine A2A receptors in ventral striatum, hypothalamus and nociceptive circuitry: Implications for drug addition, sleep and pain", Progress in Neurobiology, vol. 83 (2007) 332-347.
Hewitt, "The Use of NMDA-Receptor Antagonists in the Treatment of Chronic Pain", The Clinical Journal of Pain, vol. 16, No. 2 (2000) S73-79.
Jacobson, et al., "Structure-Activity Relationships of 8-Styrylxanthines as A2-Selective Adenosine Antagonists", J. Med. Chem., vol. 36, No. 10 (1993) 1333-42.
Jacobson, et al., "Adenosine receptors as therapeutic targets", Nature Reviews/Drug Discovery, vol. 5 (2006) 247-64.
Ledent, et al., "Aggressiveness, hypoalgesia and high blood pressure in mice lacking the adenosine A2a receptor", Nature, vol. 388 (1997) 674-78.
Neustadt, et al., "Potent, selective, and orally active adenosine A2A receptor antagonists: Arylpiperazine derivatives of pyrazolo[4,3-e]-1,2,4-triazolo[1,5-c]pyrimidines", Bioorganic & Medicinal Chemistry Letters, vol. 17 (2007) 1376-80.
Nonaka, et al., "KF17837 ((E)-8(3,4-dimethoxystyryl)-1,3-diporopyl-7-methylxanthine), a potent and selective adenosine A2 receptor antagonist", European Journal of Pharmacology, vol. 267 (1994) 335-41.
Popik, et al., "Clinically available NMDA receptor antagonists memantine and dextromethorphan reverse existing tolerance to the antinociceptive effects of morphine in mice", Naunyn-Schmiedeberg's Arch Pharmacol, vol. 361 (2000) 425-32.
Stella, et al., "Interactive role of adenosine and dopamine in the opiate withdrawal syndrome", Naunyn-Schmiedeberg's Arch Pharmacol, vol. 368 (2003) 113-18.
Stella, et al., "Role of A1 and A2A Adenosine Receptors in the Opiate Withdrawal Syndrome", Research Comm. in Alcohol and Substances of Abuse, vol. 18, Nos. 3 and 4 (1997) 141-8.
Sahraei, et al., "Adenosine A2 receptors inhibit morphine self-administration in rats", European Journal of Pharmacology, vol. 383 (1999) 107-13.
Snyder, "Adenosine Receptors: Knockouts anxious for new theraphy", Nature, vol. 388 (1997) 624.
Suzuki, et al., "Effects of the Adenosine A1-Receptor Antagonist on Defecation, Small Intestinal Propulsion and Gastric Emptying in Rats", Jpn. J. Pharmacol., vol. 68 (1995) 119-23.
Verdi, et al., "Finasteride, a 5α-reductase inhibitor, potentiates antinociceptive effects of morphine, prevents the development of morphine tolerance and attenuates abstinence behavior in the rat", Hormones and Behavior, vol. 51 (2007) 605-10.
Yao, et al., "Adenosine A2a blockade prevents synergy between μ-opiate and cannabinoid CB1 receptors and eliminates heroin-seeking behavior in addicted rats", PNAS, vol. 103, No. 20 (2006) 7877-82.
Yuan, "Methylnaltrexone Mechanisms of Action and Effects on Opioid Bowel Dysfunction and Other Opioid Adverse Effects", The Annals of Pharmacotheraphy, vol. 41 (2007) 984-93.
Hussey, et al., "Reduced response to the formalin test and lowered spinal NMDA glutamate receptor binding in adenosine A2A receptor knockout mice", Pain, vol. 129, No. 3 (2007) 287-94.
Matsubara, et al., "The treatment of Parkinson's disease—adenosine A2A receptor antagonists", Nippon Rinsho, vol. 60, No. 1 (2002) 112-16.
Misra, et al., "Potentiation of morphine analgesia by caffein", Br. J. Pharmac, vol. 84, No. 4 (1985) 789-91.
Nihon Yakurigaku Zasshi (J. Pharm. Sci), vol. 129, No. 5 (2007) 390-91.
Abo-Salem, et al., "Antinociceptice Effects of Novel A2B Adenosine Receptor Antagonists", J. Pharmacol. Exp. Ther., vol. 308, No. 1 (2004) 358-66.
Malec, et al., "The Effect of Methylxanthines on Morphine Analgesia in Mice and Rats", Pol. J. Pharmacol. Pharm., vol. 40 (1988) 223-32.
Matsuda, "Experimental Studies on the Effective Procedure to Inhibit the Development of Tolerance to and Dependence on Morphine", Arzneim.-Forsch (Drug Res.), vol. 20 (1970) 1596-604.
Batista, et al., "Blockade of adenosine and dopamine receptors inhibits the development of rapid tolerance to ethanol in mice", Psychopharmacology, vol. 181 (2005) 714-21.
Sahraei, et al., "Theophylline inhibits tolerance and sensitization induced by morphine: a conditioned place preference paradigm study in female mice", Behavioural Pharmacology, vol. 17 (2006) 621-28.

* cited by examiner

INHIBITOR OF ANALGESIC TOLERANCE

TECHNICAL FIELD

The present invention relates to an agent for suppressing an undesirable effect (for example, analgesic tolerance, hyperalgesia, dependence, constipation, drowsiness, etc.) of an opioid-type analgesic (opioid), which comprises a compound having adenosine $A_{2A}$ receptor antagonistic activity or a pharmaceutically acceptable salt thereof as an active ingredient, and the like.

BACKGROUND ART

An opioid is widely used for serious acute pain and chronic pain. It is known that an opioid shows a strong analgesic effect and also exhibits undesirable effect such as analgesic tolerance, hyperalgesia, constipation, dependence, and drowsiness (The Medical Clinics of North America, 2007, Vol. 91, p. 199). Conventionally, as a main method for treating and/or preventing analgesic tolerance or hyperalgesia caused by an opioid, increase in the dose of the opioid, opioid rotation, change of administration route, or the like has been performed. However, the increase in the dose of the opioid has a problem that the side effects of the opioid itself such as constipation, nausea, drowsiness, respiratory depression, confusion, and immunosuppression also become severe, and the critical effectiveness is decreased from the overall viewpoint. Further, as for the opioid rotation or change of administration route, there are not a few cases where the option to be taken is limited due to the site of pain or the past history of a patient (for example, nephropathy, hepatopathy, etc.).

As a method for reducing the undesirable effect of an opioid such as dependence, for example, there are reports as described below: (1) Oxytrex ("The Journal of Pain", 2005, Vol. 6, p. 392) or Embeda ("Annual Meeting of The American Society of Anesthesiologists", 2007, Abstract A1370), both of which are a mixed preparation of an opioid and an ultra-low dose of an opioid antagonist, reduces opioid physical dependence as compared with the single administration of an opioid; (2) methylnaltrexone improve constipation induced by the administration of an opioid ("The Annals of Pharmacotherapy", 2007, Vol. 41, p. 984); (3) aminoguanidine suppresses analgesic tolerance and physical dependence of morphine ("European Journal of Pharmacology", 2006, Vol. 540, pp. 60-66); (4) finasteride suppresses analgesic tolerance and physical dependence of morphine ("Hormones and Behavior", 2007, Vol. 51, p. 605); (5) an N-methyl-D-aspartic acid (NMDA) receptor antagonist suppresses analgesic tolerance and dependence of opioid ("Naunyn-Schmiedeberg's Archives of Pharmacology", 2000, Vol. 361, p. 425; "The Clinical Journal of Pain", 2000, Vol. 16, pp. S73-9); (6) a GM1 ganglioside inhibitor suppresses analgesic tolerance and physical dependence of morphine and the like (US 2004-0087607); (7) 3,7-dimethyl-1-propargylxanthine (DMPX), which is an adenosine receptor antagonist, suppresses psychological dependence of morphine (see Non-patent document 1); (8) DMPX suppresses psychological dependence of heroine (see Non-patent document 2 and Patent document 1); (9) 8-(3-chlorostyryl) caffeine (CSC) suppresses psychological dependence of morphine (see Non-patent document 3); (10) ZM241385, which is an adenosine receptor antagonist, affects an excitatory postsynaptic current induced by DAMGO, which is one of the opioid peptides (see Non-patent document 4); and (11) SCH59261 and CSC, both of which are an adenosine receptor antagonist, suppress physical dependence of morphine (see Non-patent document 8).

On the other hand, it is known that adenosine is widely distributed in the body and exhibits various physiological effects on the central nervous system, cardiac muscle, kidney, smooth muscle, and the like via its receptors (see Non-patent document 5).

For example, it is known that an adenosine $A_1$ antagonist has defecation promoting activity (see Non-patent document 6). It is also known that the adenosine $A_{2A}$ receptors are involved particularly in the central nervous system, and an adenosine $A_{2A}$ receptor antagonist is known to be useful as a therapeutic agent for, for example, Parkinson's disease and the like (see Non-patent document 7). Further, a composition comprising an adenosine $A_{2A}$ receptor antagonist and an opioid for treating restless legs syndrome (RLS) and the like are also known (see Patent documents 2 and 3). Further, a method for alleviating chronic consumption of abused drugs such as ethanol or an opioid using an adenosine $A_{2A}$ receptor antagonist (see Patent documents 1 and 4), a method for treating a disease with chronic musculoskeletal pain (see Patent document 5) and the like are known. Furthermore, it is also known that an adenosine $A_{2B}$ receptor antagonist is useful as a therapeutic agent for constipation (see Patent document 6).

As a compound having an adenosine $A_{2A}$ receptor antagonistic activity, for example, compounds represented by the following formulae (IA), (IB), (IC), (ID), (IIA), (IIIA), (IIIB), (IIIC), (IVA), (V), (VIA), (VII), (VIII), and the like are known (see Patent documents 7 to 13, and Non-patent documents 9 to 11).

[Chemical 1]

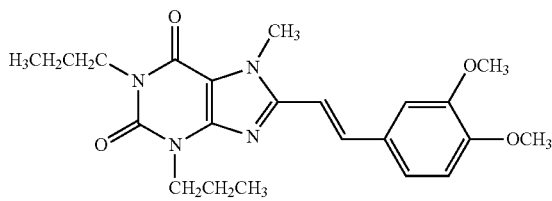

(IA)

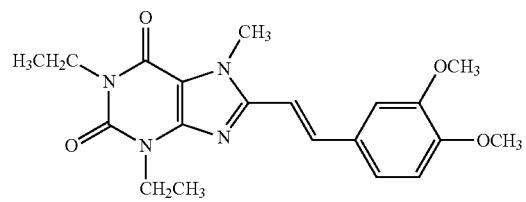

(IB)

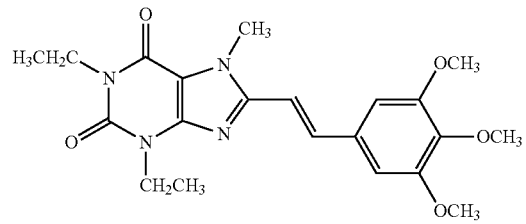

(IC)

-continued

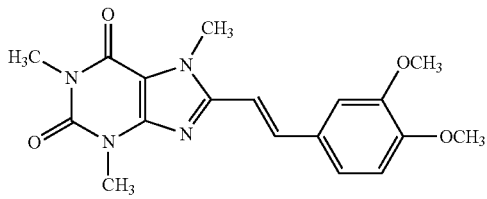
(ID)

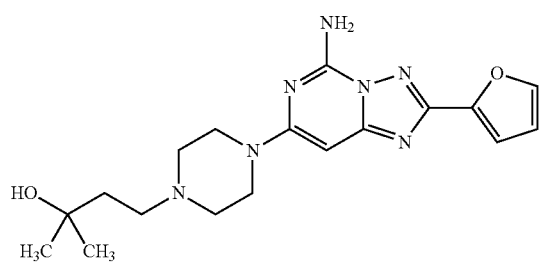
(IIA)

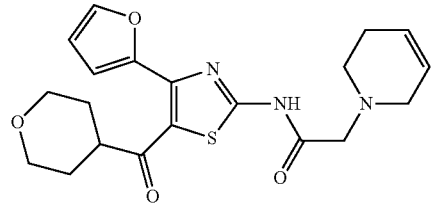
(IIIA)

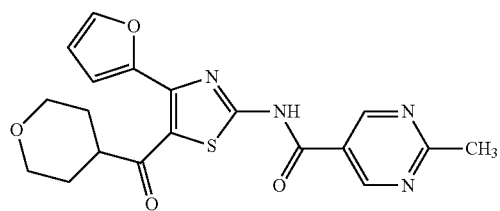
(IIIB)

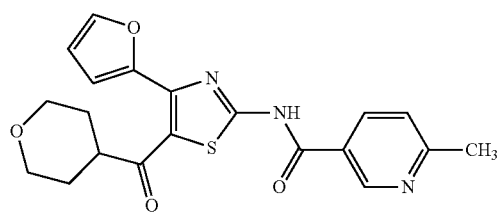
(IIIC)

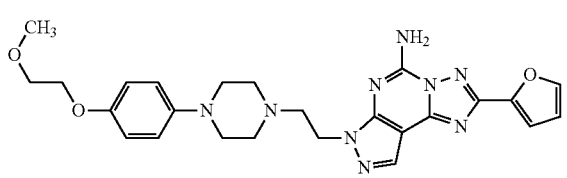
(IVA)

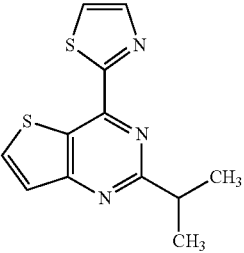
(V)

-continued

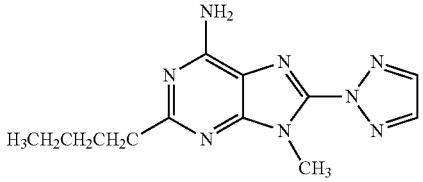
(VIA)

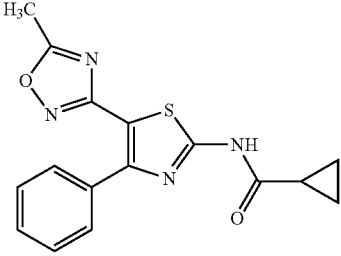
(VII)

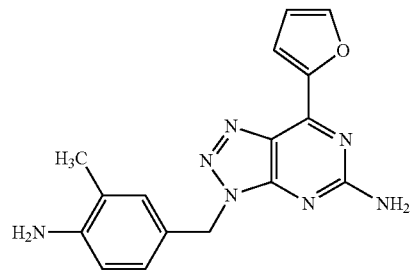
(VII)

PRIOR ART DOCUMENTS

Patent Documents

Patent document 1: WO 2006/009698
Patent document 2: WO 2007/047293
Patent document 3: WO 2007/038212
Patent document 4: WO 2006/059713
Patent document 5: WO 2005/094885
Patent document 6: WO 01/080893
Patent document 7: U.S. Pat. No. 5,587,378
Patent document 8: WO 00/17201
Patent document 9: WO 2005/063743
Patent document 10: WO 2002/055524
Patent document 11: WO 2003/011864
Patent document 12: WO 2006/032273
Patent document 13: WO 2002/055083

Non-Patent Documents

Non-patent document 1: "European Journal of Pharmacology", 1999, Vol. 383, p. 107
Non-patent document 2: "Proceedings of the National Academy of Sciences of the United States of America", 2006, Vol. 103, p. 7877
Non-patent document 3: "Research Communications in Alcohol and Substances of Abuse", 1997, Vol. 18, p. 141
Non-patent document 4: "Neuroscience Letters", 2005, Vol. 376, p. 102
Non-patent document 5: "Nature Reviews Drug Discovery", 2006, Vol. 5, p. 247
Non-patent document 6: "Jpn. J. Pharmacol.", 1995, Vol. 68, p. 119
Non-patent document 7: "Progress in Neurobiology", 2007, Vol. 83, p. 332

Non-patent document 8: "Naunyn-Schmiedeberg's Archives of Pharmacology", 2003, Vol. 368, p. 113

Non-patent document 9: "European Journal of Pharmacology", 1994, Vol. 267, p.

Non-patent document 10: "Bioorganic 85 Medicinal Chemistry Letters", 2007, Vol. 17, p. 1376

Non-patent document 11: "Journal of Medicinal Chemistry", 1993, Vol. 36, p.

SUMMARY OF THE PRESENT INVENTION

Problems that the Present Invention is to Solve

An object of the present invention is to provide an agent for suppressing an undesirable effect (for example, analgesic tolerance, hyperalgesia, constipation, dependence, drowsiness, etc.) of an opioid, which comprises a compound having adenosine $A_{2A}$ receptor antagonistic activity or a pharmaceutically acceptable salt thereof as an active ingredient, and the like.

Means for Solving the Problems

The present invention relates to the following (1) to (93).

(1) An agent for suppressing an undesirable effect of an opioid, which comprises a compound having adenosine $A_{2A}$ receptor antagonistic activity or a pharmaceutically acceptable salt thereof as an active ingredient.

(2) The agent according to (1), wherein the undesirable effect is analgesic tolerance, hyperalgesia, constipation, dependence, or drowsiness.

(3) The agent according to (1), wherein the undesirable effect is analgesic tolerance or constipation.

(4) The agent according to (1), wherein the undesirable effect is analgesic tolerance.

(5) The agent according to any one of (1) to (4), wherein the compound having adenosine $A_{2A}$ receptor antagonistic activity is a compound represented by any one of the following formulae (I) to (VIII).

[Chemical 2]

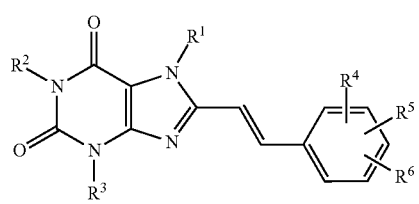
(I)

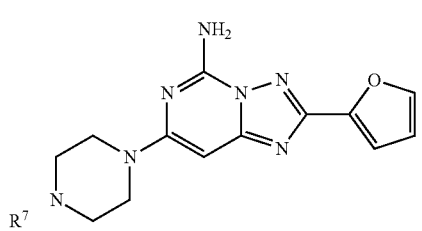
(II)

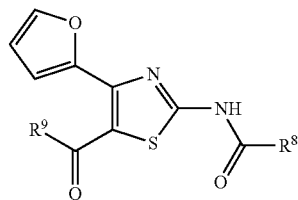
(III)

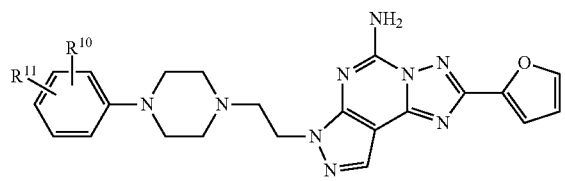
(IV)

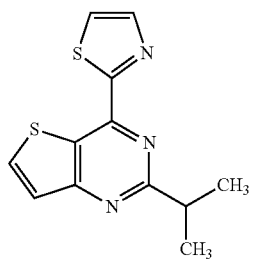
(V)

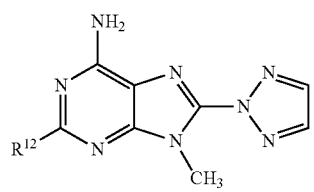
(VI)

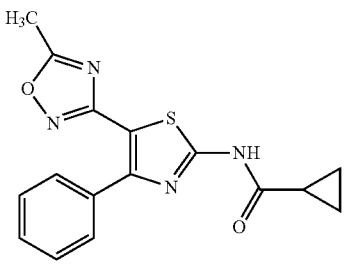
(VII)

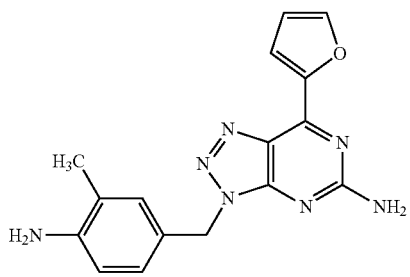
(VIII)

(Wherein, $R^1$ represents a hydrogen atom or methyl; $R^2$ and $R^3$ may be the same or different, and each represents methyl, ethyl, propyl, butyl, or isopropyl; $R^4$, $R^5$, and $R^6$ may be the same or different, and each represents a hydrogen atom, methyl, ethyl, methoxy, ethoxy, a fluorine atom, a chlorine atom, or a bromine atom; $R^7$ represents methyl, ethyl, propyl, butyl, or 3-methylbutyl, or any of these groups substituted by hydroxy; $R^8$ represents phenyl, pyridyl, pyrimidinyl, or 5,6-dihydro-2H-pyridylmethyl, or any of these groups substituted by 1 to 3 substituents selected from a chlorine atom, methyl, ethyl, methoxy, and ethoxy; $R^9$ represents pyridyl or tetrahydropyranyl; $R^{10}$ and $R^{11}$ may be the same or different, and each represents a hydrogen atom, a fluorine atom, or 2-methoxyethoxy; and $R^{12}$ represents methyl, ethyl, propyl, or butyl.)

(6) The agent according to any one of (1) to (4), wherein the compound having adenosine $A_{2A}$ receptor antagonistic activity is a compound represented by the following formula (I).

[Chemical 3]

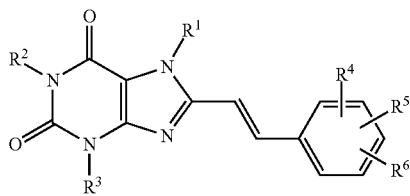

(I)

(Wherein, $R^1$, $R^2$, $R^3$, $R^4$, $R^5$, and $R^6$ have the same definitions as described above, respectively.)

(7) The agent according to any one of (1) to (4), wherein the compound having adenosine $A_{2A}$ receptor antagonistic activity is a compound represented by the following formula (II).

[Chemical 4]

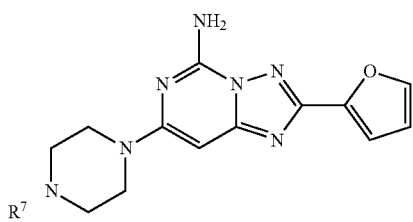

(II)

(Wherein, $R^7$ has the same definition as described above.)

(8) The agent according to any one of (1) to (4), wherein the compound having adenosine $A_{2A}$ receptor antagonistic activity is a compound represented by the following formula (III).

[Chemical 5]

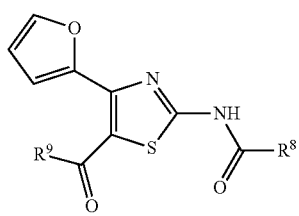

(III)

(Wherein, $R^8$ and $R^9$ have the same definitions as described above, respectively.)

(9) The agent according to any one of (1) to (4), wherein the compound having adenosine $A_{2A}$ receptor antagonistic activity is a compound represented by the following formula (IA), (IB), (IC), (ID), (IIA), (IIIA), (IIIB), (MC), (IVA), (V), (VIA), (VII), or (VIII).

[Chemical 6]

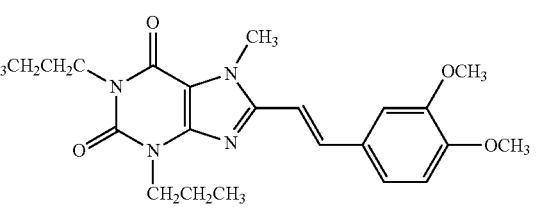

(IA)

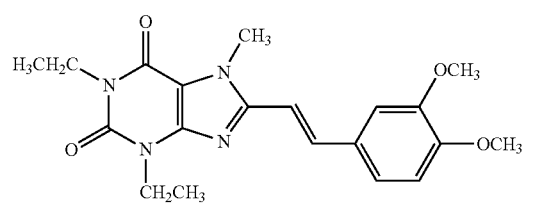

(IB)

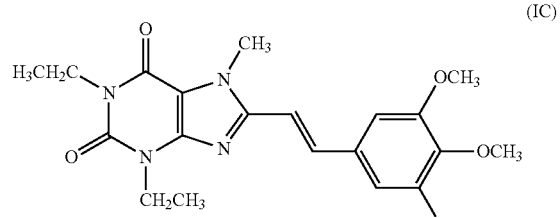

(IC)

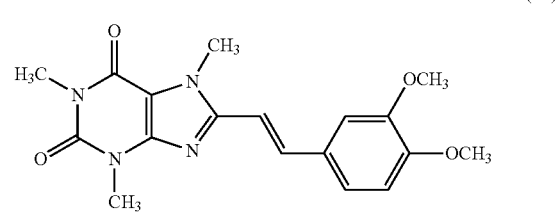

(ID)

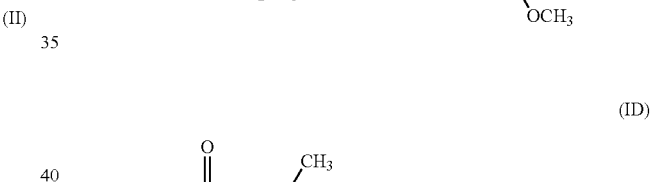

(IIA)

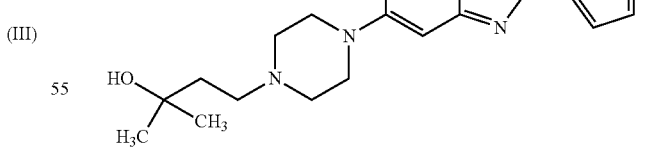

(IIIA)

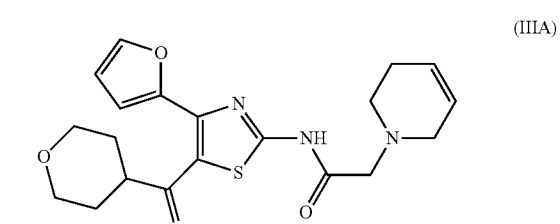

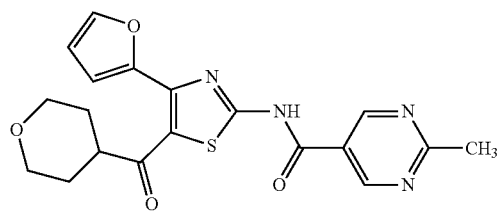
(IIIB)

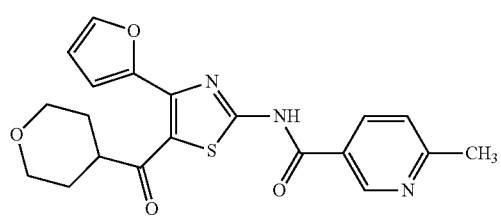
(IIIC)

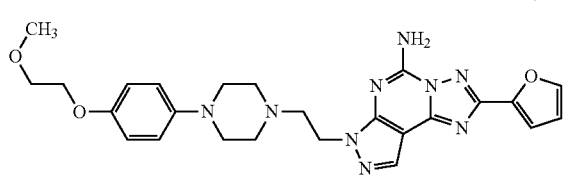
(IVA)

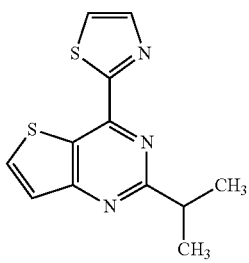
(V)

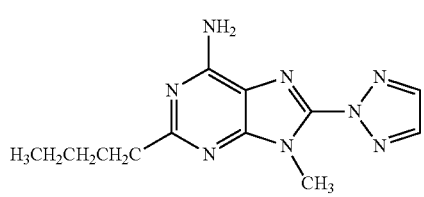
(VIA)

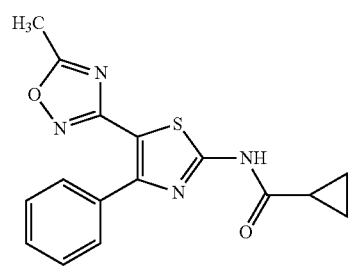
(VII)

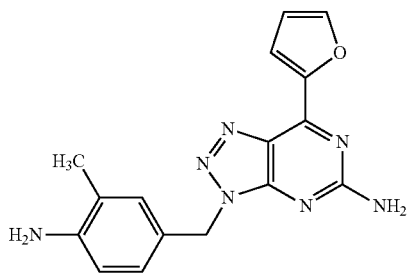
(VIII)

(10) The agent according to any one of (1) to (4), wherein the compound having adenosine $A_{2A}$ receptor antagonistic activity is a compound represented by the following formula (IA) or (IB).

[Chemical 7]

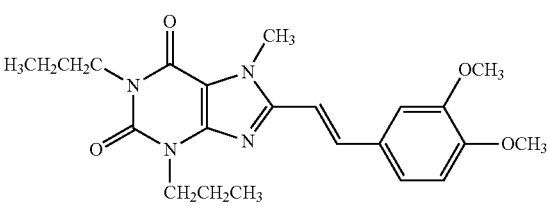
(IA)

(IB)

(11) The agent according to any one of (1) to (4), wherein the compound having adenosine $A_{2A}$ receptor antagonistic activity is a compound represented by the following formula (IIA), (IIIA), (MB), or (IIIC).

[Chemical 8]

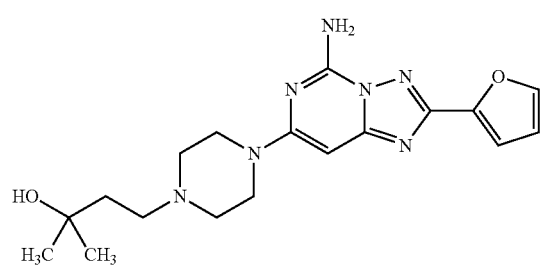
(IIA)

-continued

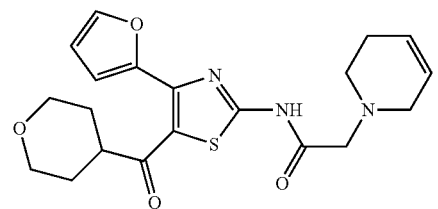
(IIIA)

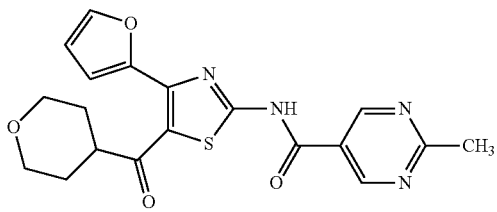
(IIIB)

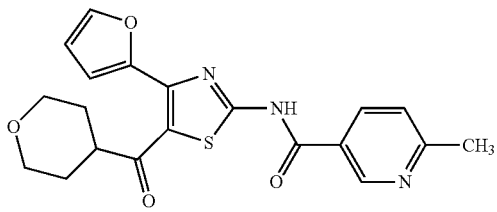
(IIIC)

(12) The agent according to any one of (1) to (11), wherein the opioid is selected from the group consisting of anileridine, opium, ampromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

(13) The agent according to any one of (1) to (11), wherein the opioid is morphine, fentanyl, or oxycodone.

(14) The agent according to any one of (1) to (11), wherein the opioid is morphine.

(15) A therapeutic and/or preventive agent for pain, which comprises (a) a compound having adenosine $A_{2A}$ receptor antagonistic activity or a pharmaceutically acceptable salt thereof and (b) an opioid in combination.

(16) A therapeutic and/or preventive agent for pain, which comprises the following (a) and (b) as active ingredients, both of which are to be administered simultaneously or separately at an interval: (a) a compound having adenosine $A_{2A}$ receptor antagonistic activity or a pharmaceutically acceptable salt thereof; and (b) an opioid.

(17) The agent according to (15) or (16), wherein the pain is selected from the group consisting of nociceptive pain, cancer pain, dorsolumbar pain, postoperative pain, herpes zoster pain, osteoarticular pain, dorsolumbar pain, rheumatic joint pain, pain accompanying osteoarthritis, fibromyalgia, myofascial pain, visceral pain, inflammatory pain, neuropathic pain, entrapment neuropathy, postherpetic neuralgia, diabetic pain, neurological low back pain, pain after infection with AIDS virus, post-spinal cord injury pain, and trigeminal neuralgia.

(18) The agent according to any one of (15) to (17), wherein the compound having adenosine $A_{2A}$ receptor antagonistic activity is a compound represented by any one of the following formulae (I) to (VIII).

[Chemical 9]

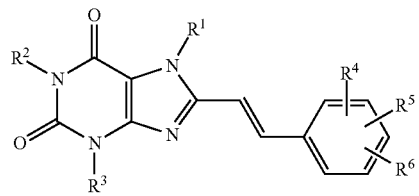
(I)

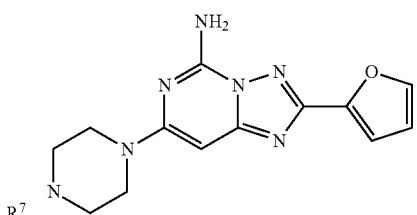
(II)

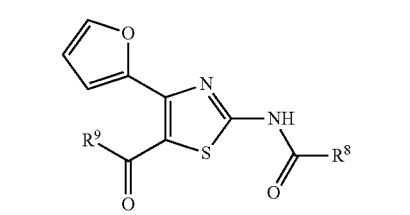
(III)

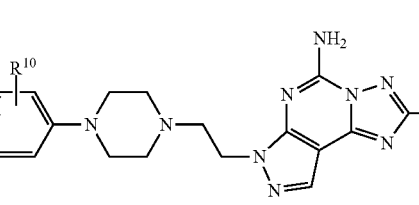
(IV)

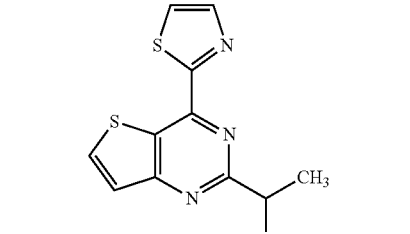
(V)

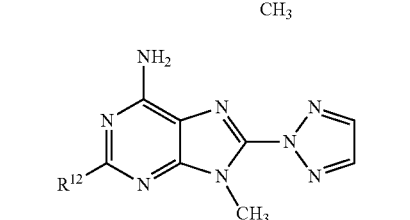
(VI)

-continued (VII)

(VIII)

(Wherein, R¹, R², R³, R⁴, R⁵, R⁶, R⁷, R⁸, R⁹, R¹⁰, R¹¹, and R¹² have the same definitions as described above, respectively.)

(19) The agent according to any one of (15) to (17), wherein the compound having adenosine $A_{2A}$ receptor antagonistic activity is a compound represented by the following formula (I).

[Chemical 10]

(I)

(Wherein, R¹, R², R³, R⁴, R⁵, and R⁶ have the same definitions as described above, respectively.)

(20) The agent according to any one of (15) to (17), wherein the compound having adenosine $A_{2A}$ receptor antagonistic activity is a compound represented by the following formula (II).

[Chemical 11]

(II)

(Wherein, R⁷ has the same definition as described above.)

(21) The agent according to any one of (15) to (17), wherein the compound having adenosine $A_{2A}$ receptor antagonistic activity is a compound represented by the following formula (III).

[Chemical 12]

(III)

(Wherein, R⁸ and R⁹ have the same definitions as described above, respectively.)

(22) The agent according to any one of (15) to (17), wherein the compound having adenosine $A_{2A}$ receptor antagonistic activity is a compound represented by the following formula (IA), (IB), (IC), (ID), (IIA), (IIIA), (IIIB), (IIIC), (IVA), (V), (VIA), (VII), or (VIII).

[Chemical 13]

(IA)

(IB)

(IC)

(ID)

-continued

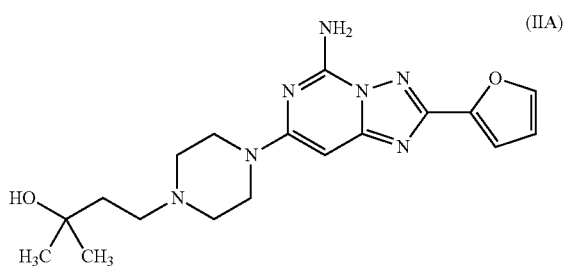
(IIA)

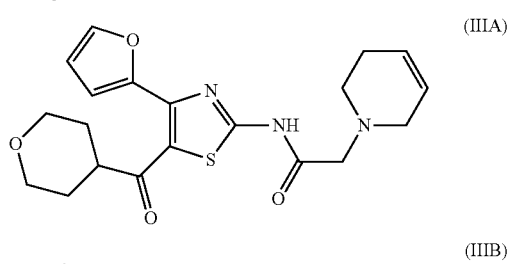
(IIIA)

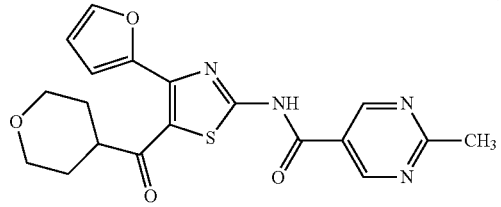
(IIIB)

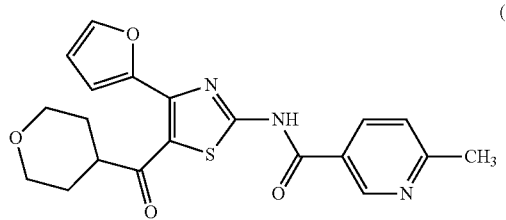
(IIIC)

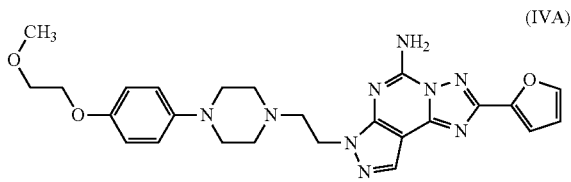
(IVA)

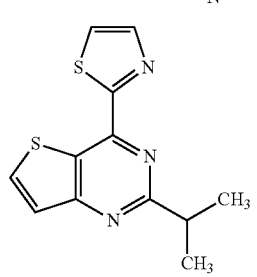
(V)

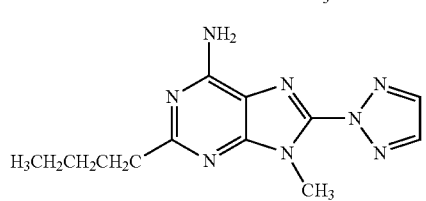
(VIA)

-continued

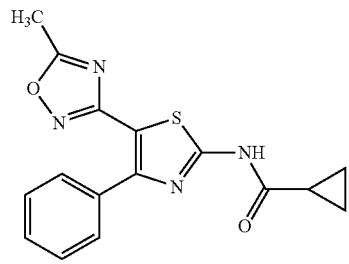
(VII)

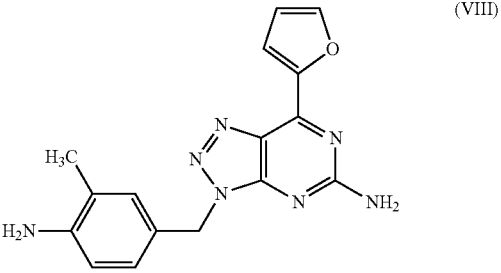
(VIII)

(23) The agent according to any one of (15) to (17), wherein the compound having adenosine $A_{2A}$ receptor antagonistic activity is a compound represented by the following formula (IA) or (IB).

[Chemical 14]

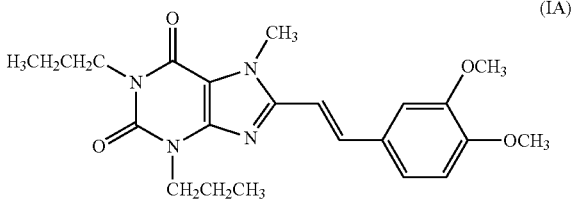
(IA)

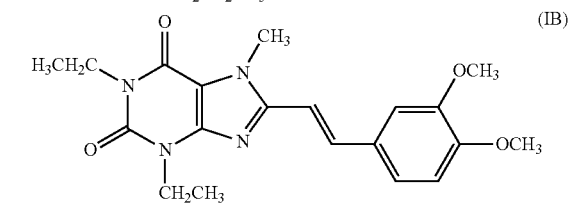
(IB)

(24) The agent according to any one of (15) to (17), wherein the compound having adenosine $A_{2A}$ receptor antagonistic activity is a compound represented by the following formula (IIA), (IIIA), (IIIB), or (IIIC).

[Chemical 15]

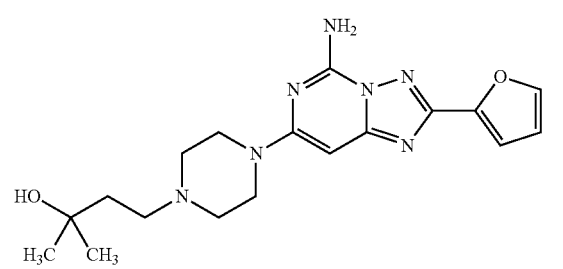
(IIA)

-continued

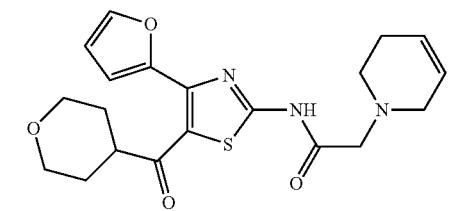
(IIIA)

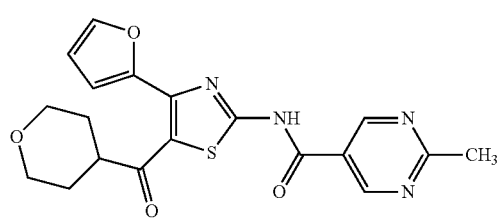
(IIIB)

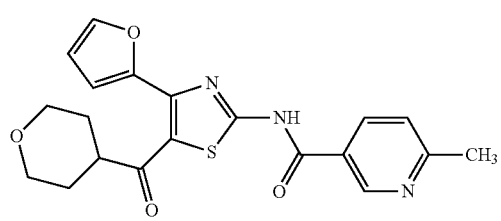
(IIIC)

(25) The agent according to any one of (15) to (24), wherein the opioid is selected from the group consisting of anileridine, opium, ampromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

(26) The agent according to any one of (15) to (24), wherein the opioid is morphine, fentanyl, or oxycodone.

(27) The agent according to any one of (15) to (24), wherein the opioid is morphine.

(28) A kit, which comprises (a) a first component containing a compound having adenosine $A_{2A}$ receptor antagonistic activity or a pharmaceutically acceptable salt thereof and (b) a second component containing an opioid.

(29) The kit according to (28), wherein the compound having adenosine $A_{2A}$ receptor antagonistic activity is a compound represented by any one of the following formulae (I) to (VIII).

[Chemical 16]

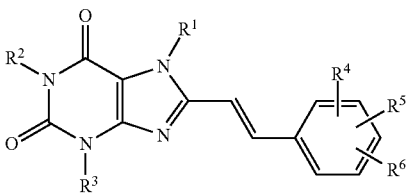
(I)

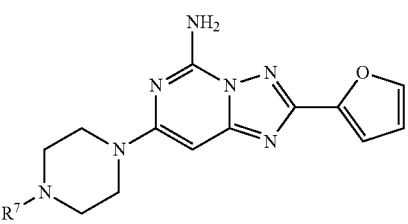
(II)

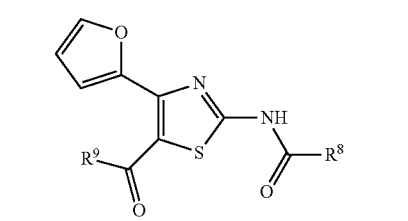
(III)

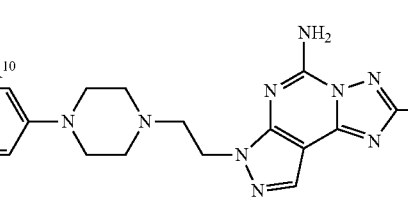
(IV)

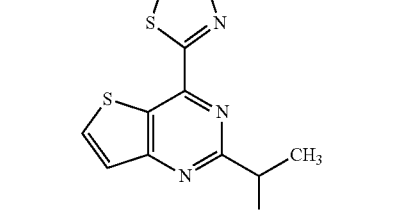
(V)

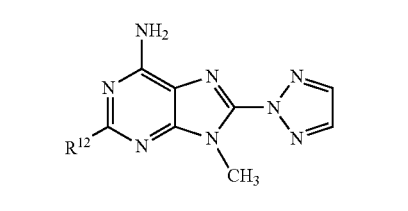
(VI)

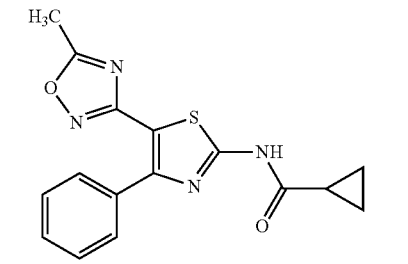
(VII)

-continued

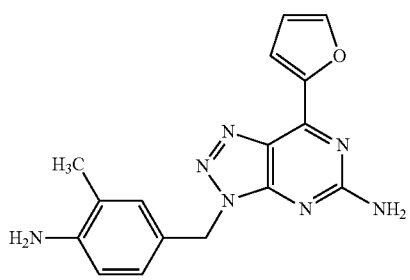
(VIII)

(Wherein, $R^1$, $R^2$, $R^3$, $R^4$, $R^5$, $R^6$, $R^7$, $R^8$, $R^9$, $R^{10}$, $R^{11}$, and $R^{12}$ have the same definitions as described above, respectively.)

(30) The kit according to (28), wherein the compound having adenosine $A_{2A}$ receptor antagonistic activity is a compound represented by the following formula (I).

[Chemical 17]

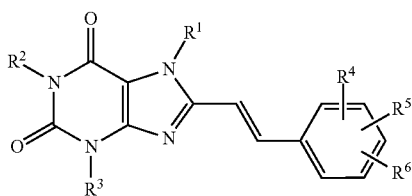
(I)

(Wherein, $R^1$, $R^2$, $R^3$, $R^4$, $R^5$, and $R^6$ have the same definitions as described above, respectively.)

(31) The kit according to (28), wherein the compound having adenosine $A_{2A}$ receptor antagonistic activity is a compound represented by the following formula (II).

[Chemical 18]

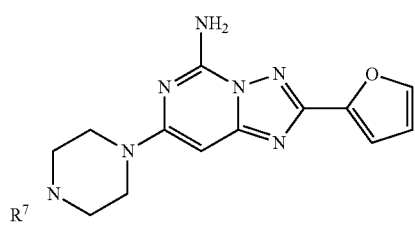
(II)

(Wherein, $R^7$ has the same definition as described above.)

(32) The kit according to (28), wherein the compound having adenosine $A_{2A}$ receptor antagonistic activity is a compound represented by the following formula (III).

[Chemical 19]

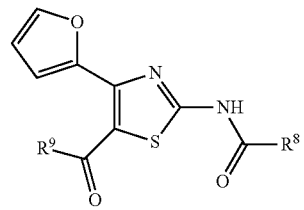
(III)

(Wherein, $R^8$ and $R^9$ have the same definitions as described above, respectively.)

(33) The kit according to (28), wherein the compound having adenosine $A_{2A}$ receptor antagonistic activity is a compound represented by the following formula (IA), (IB), (IC), (ID), (IIA), (IIIA), (IIIB), (IIIC), (IVA), (V), (VIA), (VII), or (VIII).

[Chemical 20]

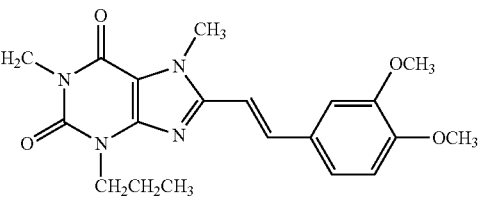
(IA)

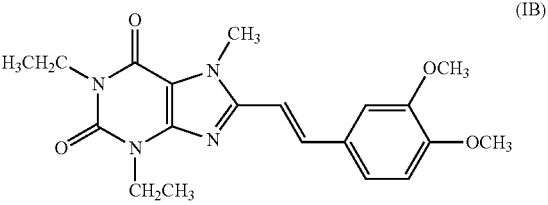
(IB)

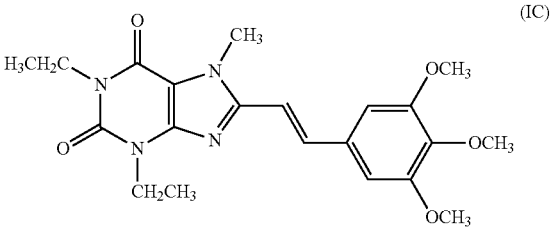
(IC)

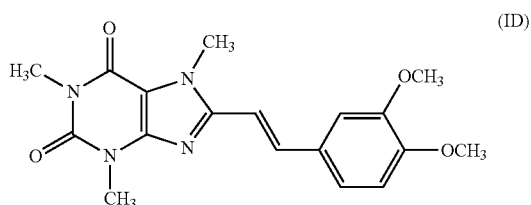
(ID)

-continued

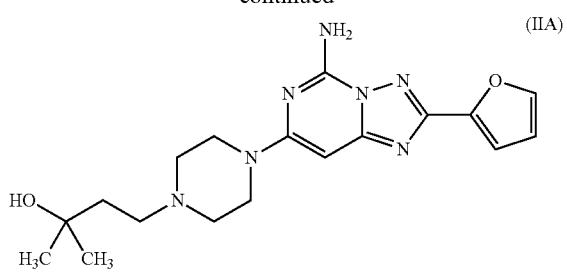
(IIA)

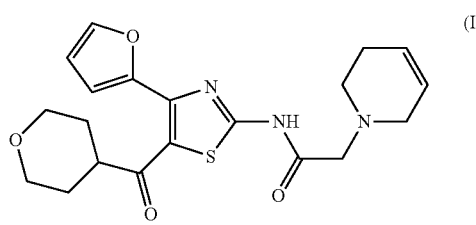
(IIIA)

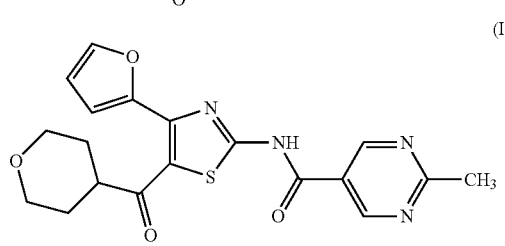
(IIIB)

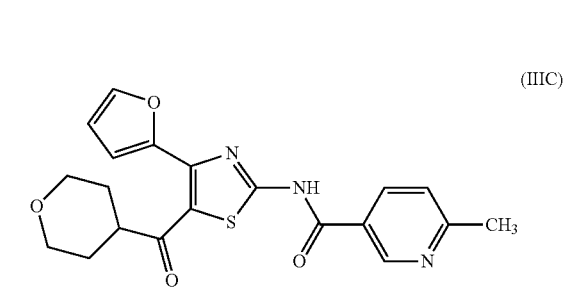
(IIIC)

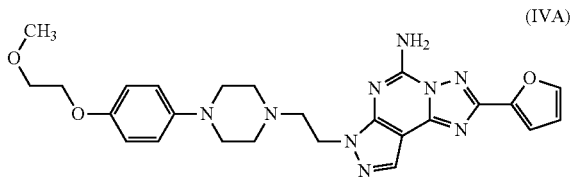
(IVA)

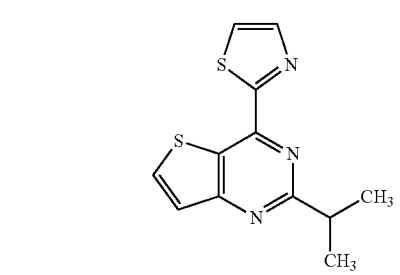
(V)

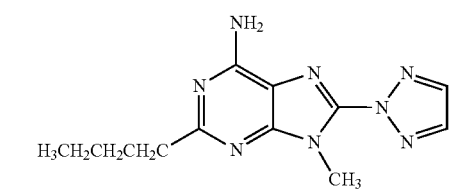
(VIA)

-continued

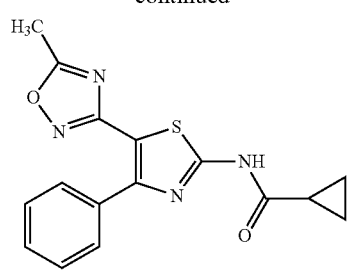
(VII)

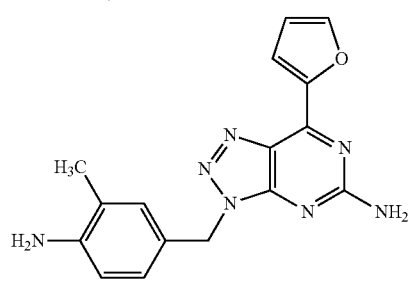
(VIII)

(34) The kit according to (28), wherein the compound having adenosine $A_{2A}$ receptor antagonistic activity is a compound represented by the following formula (IA) or (IB).

[Chemical 21]

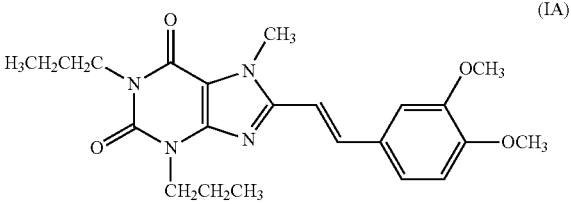
(IA)

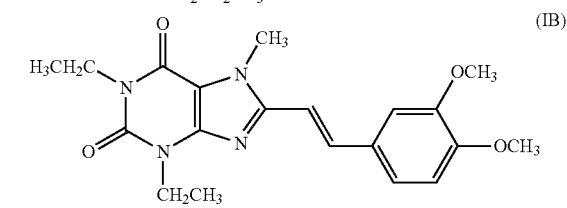
(IB)

(35) The kit according to (28), wherein the compound having adenosine $A_{2A}$ receptor antagonistic activity is a compound represented by the following formula (IIA), (IIIA), (IIIB), or (IIIC).

[Chemical 22]

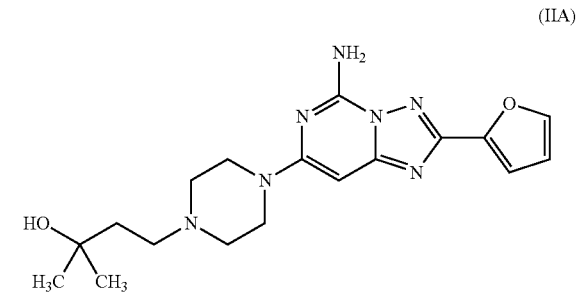
(IIA)

-continued

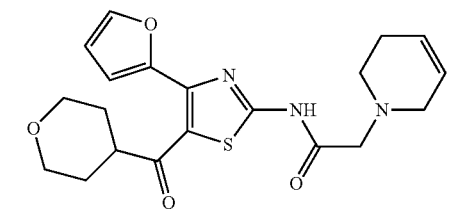
(IIIA)

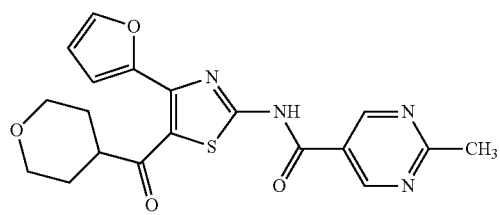
(IIIB)

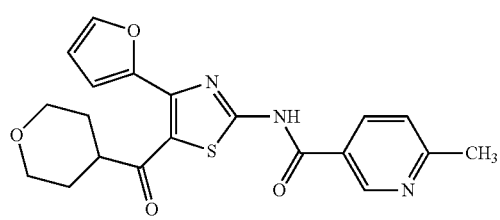
(IIIC)

(36) The kit according to any one of (28) to (35), wherein the opioid is selected from the group consisting of anileridine, opium, apromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

(37) The kit according to any one of (28) to (35), wherein the opioid is morphine, fentanyl, or oxycodone.

(38) The kit according to any one of (28) to (35), wherein the opioid is morphine.

(39) A pharmaceutical composition, which comprises (a) a compound represented by any one of the following formulae (I) to (VIII) or a pharmaceutically acceptable salt thereof and (b) an opioid.

[Chemical 23]

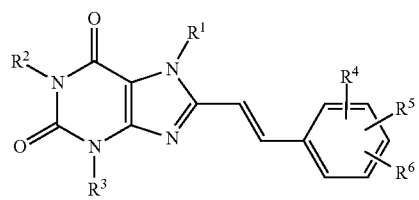
(I)

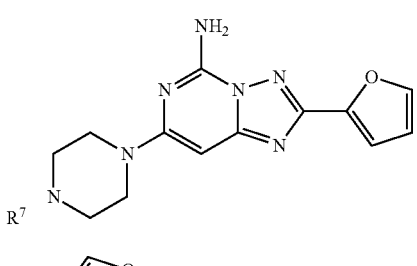
(II)

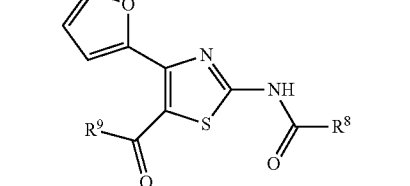
(III)

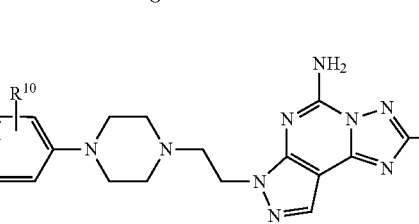
(IV)

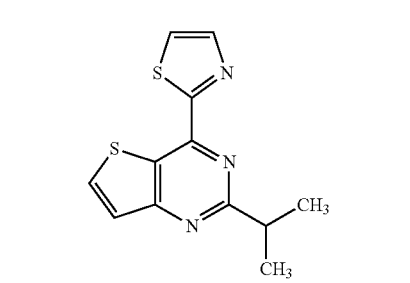
(V)

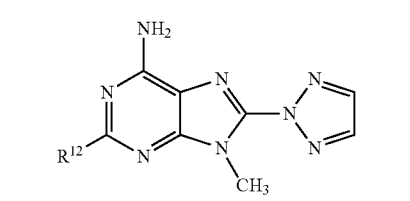
(VI)

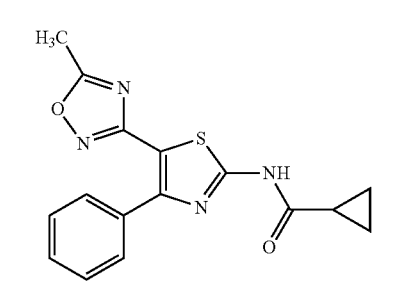
(VII)

-continued

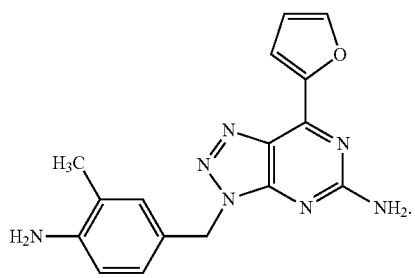
(VIII)

(Wherein, $R^1$, $R^2$, $R^3$, $R^4$, $R^5$, $R^6$, $R^7$, $R^8$, $R^9$, $R^{10}$, $R^{11}$, and $R^{12}$ have the same definitions as described above, respectively.)

(40) A pharmaceutical composition, which comprises (a) a compound represented by the following formula (I) or a pharmaceutically acceptable salt thereof and (b) an opioid.

[Chemical 24]

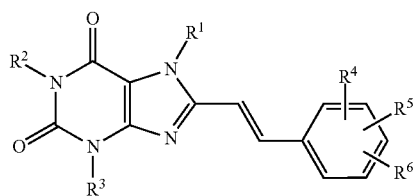
(I)

(Wherein, $R^1$, $R^2$, $R^3$, $R^4$, $R^5$, and $R^6$ have the same definitions as described above, respectively.)

(41) A pharmaceutical composition, which comprises (a) a compound represented by the following formula (II) or a pharmaceutically acceptable salt thereof and (b) an opioid.

[Chemical 25]

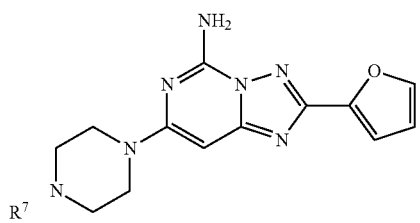
(II)

(Wherein, $R^7$ has the same definition as described above.)

(42) A pharmaceutical composition, which comprises (a) a compound represented by the following formula (III) or a pharmaceutically acceptable salt thereof and (b) an opioid.

[Chemical 26]

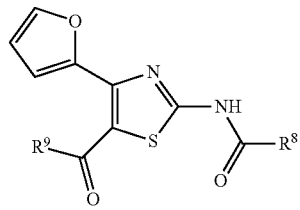
(III)

(Wherein, $R^8$ and $R^9$ have the same definitions as described above, respectively.)

(43) A pharmaceutical composition, which comprises (a) a compound represented by the following formula (IA), (IB), (IC), (ID), (IIA), (IIIA), (MB), (IIIC), (IVA), (V), (VIA), (VII), or (VIII) or a pharmaceutically acceptable salt thereof and (b) an opioid.

[Chemical 27]

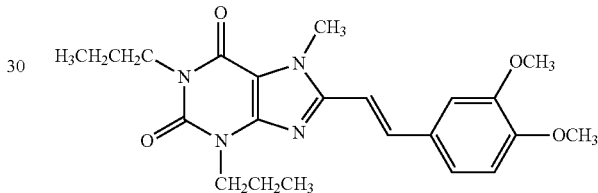
(IA)

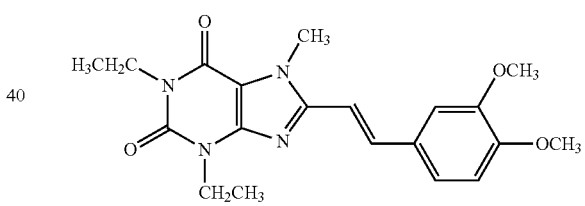
(IB)

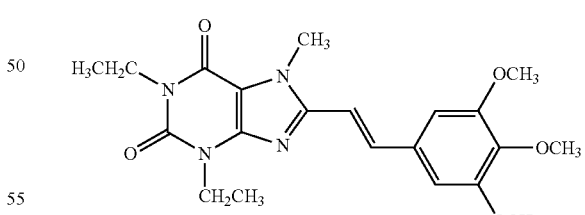
(IC)

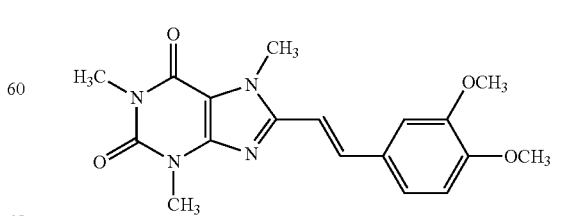
(ID)

(IIA)
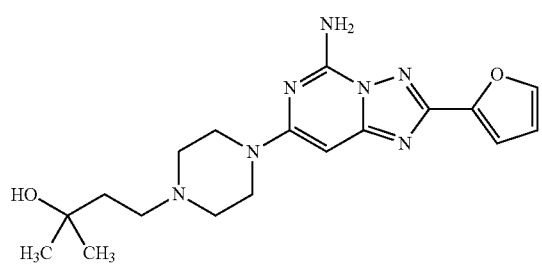

(IIIA)
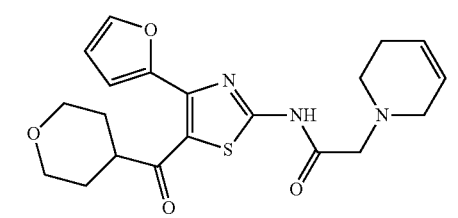

(IIIB)
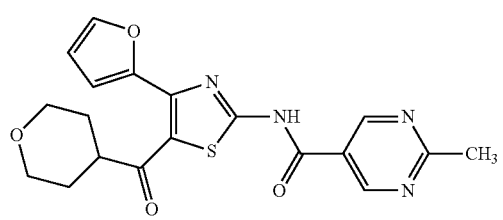

(IIIC)
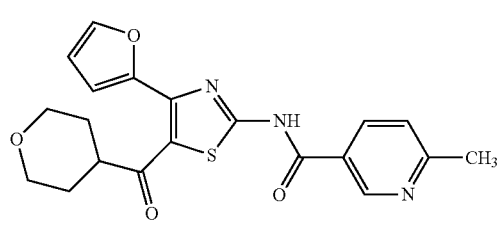

(IVA)
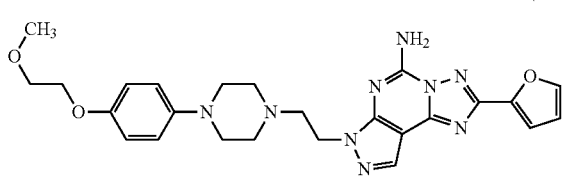

(V)
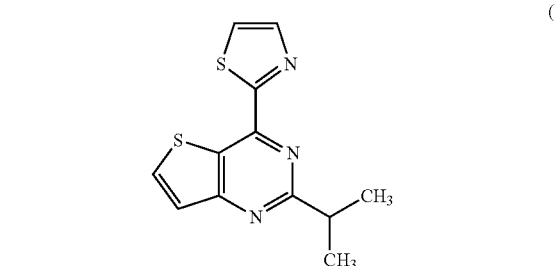

(VIA)
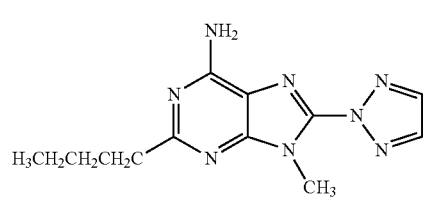

(VII)
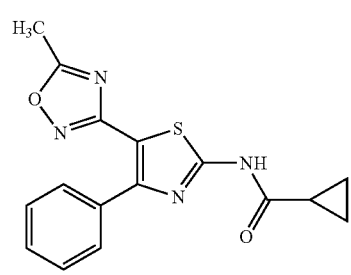

(VIII)
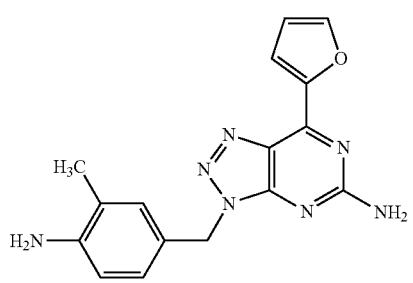

(44) A pharmaceutical composition, which comprises (a) a compound represented by the following formula (IA) or (IB) or a pharmaceutically acceptable salt thereof and (b) an opioid.

[Chemical 28]

(IA)
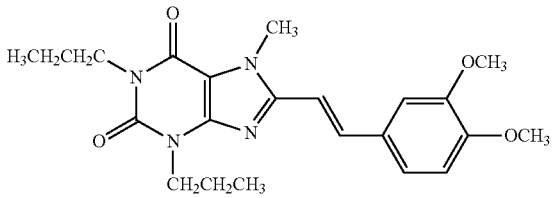

(IB)
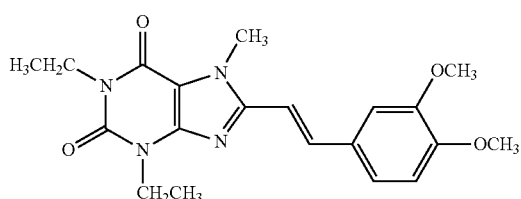

(45) A pharmaceutical composition, which comprises (a) a compound represented by the following formula (IIC), (IIIA), (IIIB), or (IIIC) or a pharmaceutically acceptable salt thereof and (b) an opioid.

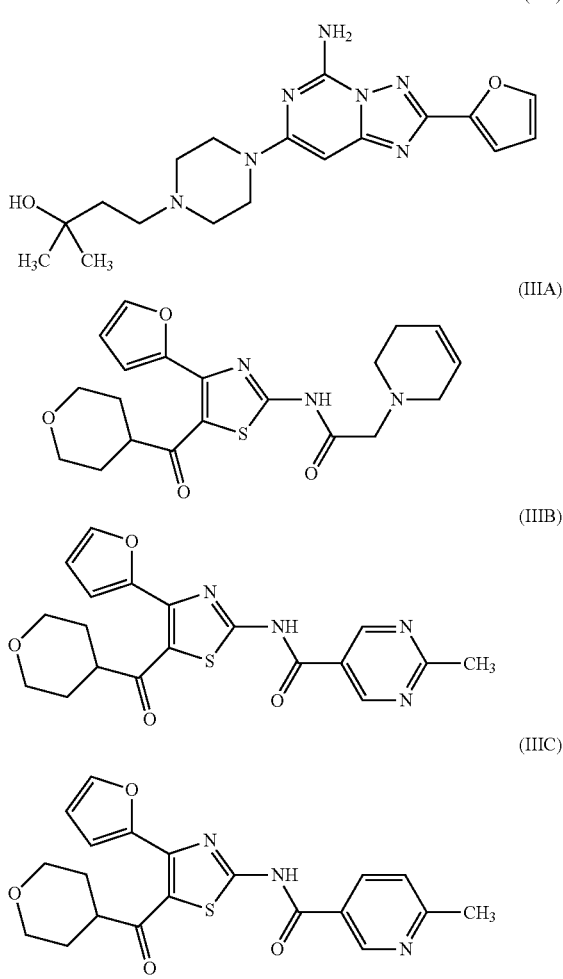

(46) The pharmaceutical composition according to any one of (39) to (45), wherein the opioid is selected from the group consisting of anileridine, opium, ampromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

(47) The pharmaceutical composition according to any one of (39) to (45), wherein the opioid is morphine, fentanyl, or oxycodone.

(48) The pharmaceutical composition according to any one of (39) to (45), wherein the opioid is morphine.

(49) A method for suppressing an undesirable effect of an opioid, which comprises administering an effective amount of a compound having adenosine $A_{2A}$ receptor antagonistic activity or a pharmaceutically acceptable salt thereof.

(50) The method according to (49), wherein the undesirable effect is analgesic tolerance or constipation.

(51) The method according to (49), wherein the undesirable effect is analgesic tolerance.

(52) The method according to any one of (49) to (51), wherein the compound having adenosine $A_{2A}$ receptor antagonistic activity is a compound represented by any one of the following formulae (I) to (VIII).

[Chemical 30]

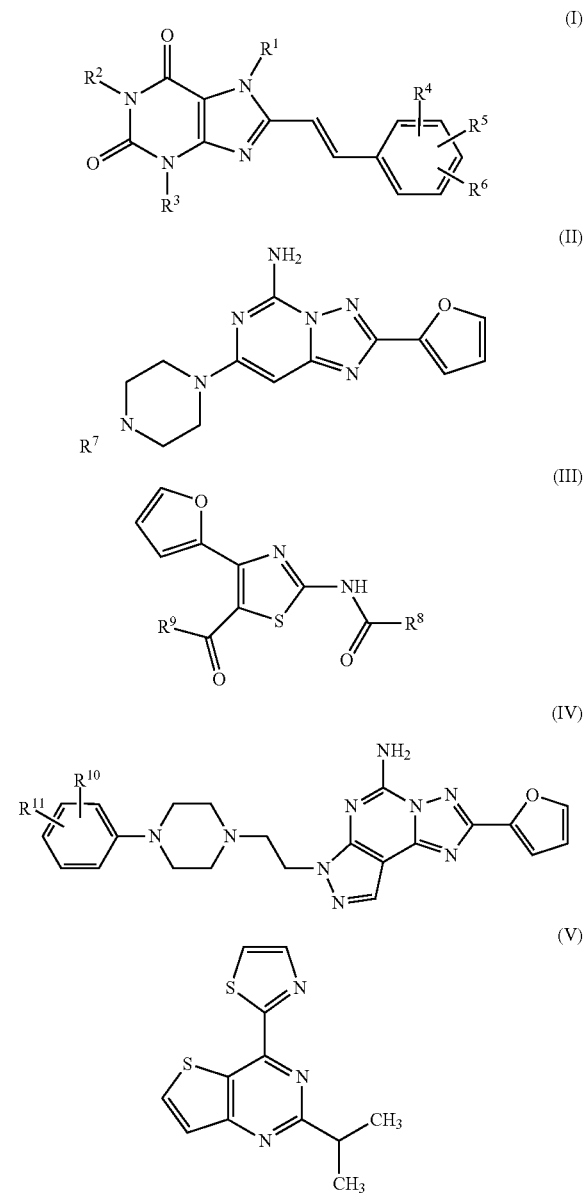

-continued (VI)
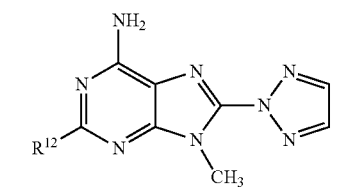

(VII)
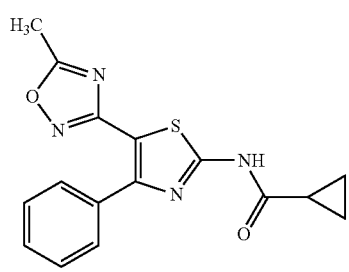

(VIII)
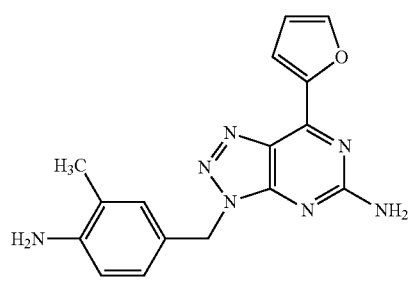

(Wherein, R¹, R², R³, R⁴, R⁵, R⁶, R⁷, R⁸, R⁹, R¹⁰, R¹¹, and R¹² have the same definitions as described above, respectively.)

(53) The method according to any one of (49) to (51), wherein the compound having adenosine $A_{2A}$ receptor antagonistic activity is a compound represented by the following formula (I), (II), or (III).

[Chemical 31]

(I)
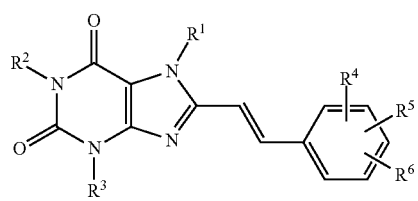

(II)
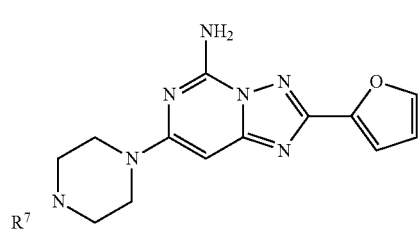

-continued (III)
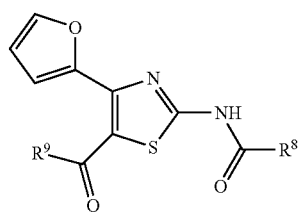

(Wherein, R¹, R², R³, R⁴, R⁵, R⁶, R⁷, R⁸, and R⁹ have the same definitions as described above, respectively.)

(54) The method according to any one of (49) to (51), wherein the compound having adenosine $A_{2A}$ receptor antagonistic activity is a compound represented by the following formula (IA), (IB), (IC), (ID), (IIA), (IIIA), (IIIB), (IIIC), (IVA), (V), (VIA), (VII), or (VIII).

[Chemical 32]

(IA)
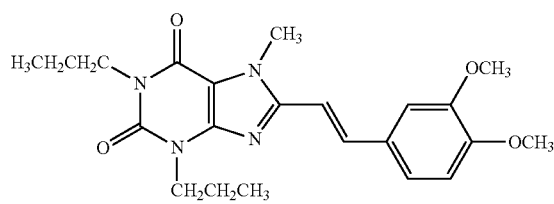

(IB)
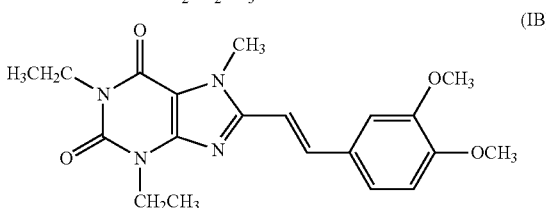

(IC)
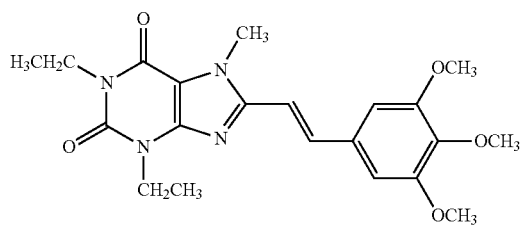

(ID)
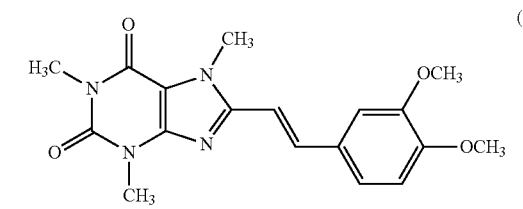

(IIA)
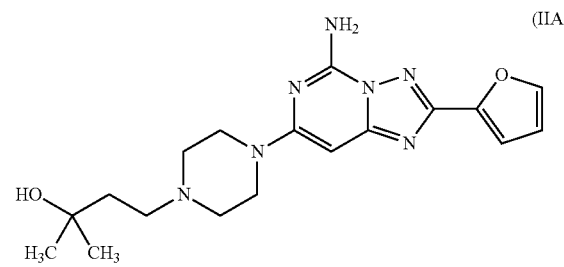

-continued

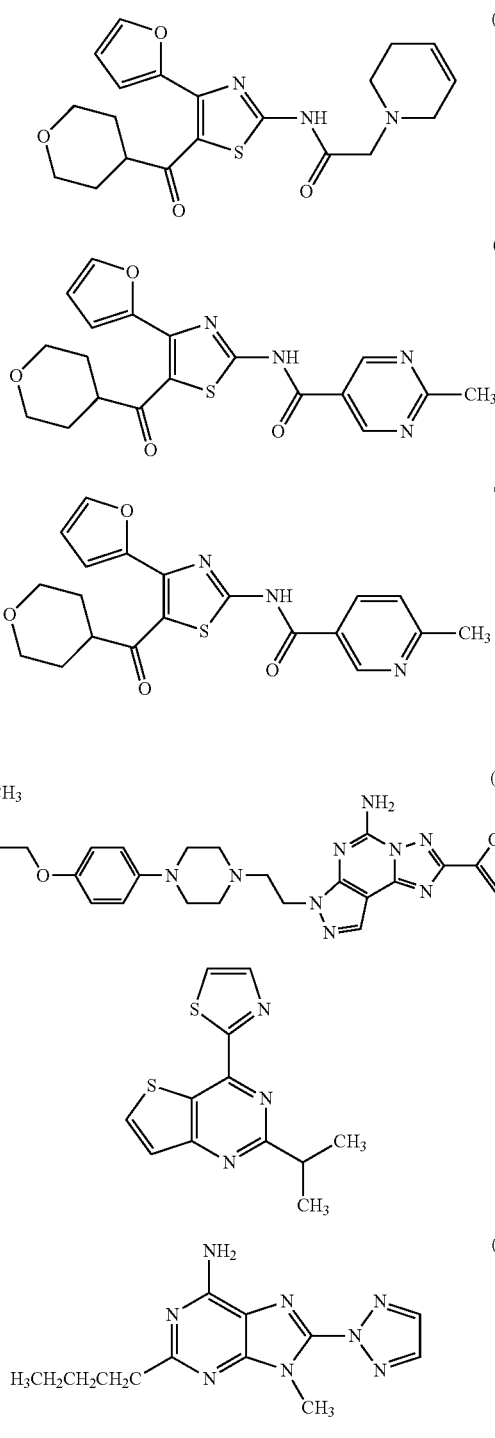

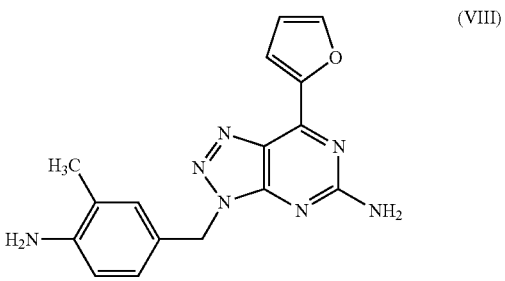

(55) The method according to any one of (49) to (54), wherein the opioid is selected from the group consisting of anileridine, opium, ampromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

(56) The method according to any one of (49) to (54), wherein the opioid is morphine.

(57) A method for treating and/or preventing pain, which comprises administering an effective amount of (a) a compound having adenosine $A_{2A}$ receptor antagonistic activity or a pharmaceutically acceptable salt thereof and (b) an effective amount of an opioid in combination.

(58) A method for treating and/or preventing pain, which comprises administering an effective amount of (a) a compound having adenosine $A_{2A}$ receptor antagonistic activity or a pharmaceutically acceptable salt thereof and (b) an effective amount of an opioid simultaneously or separately at an interval.

(59) The method according to (57) or (58), wherein the compound having adenosine $A_{2A}$ receptor antagonistic activity is a compound represented by any one of the following formulae (I) to (VIII).

[Chemical 33]

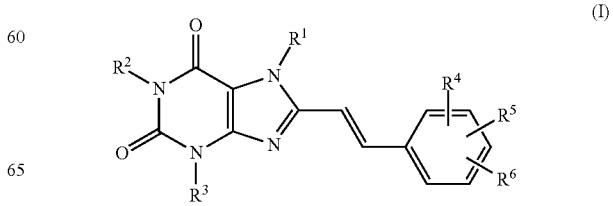

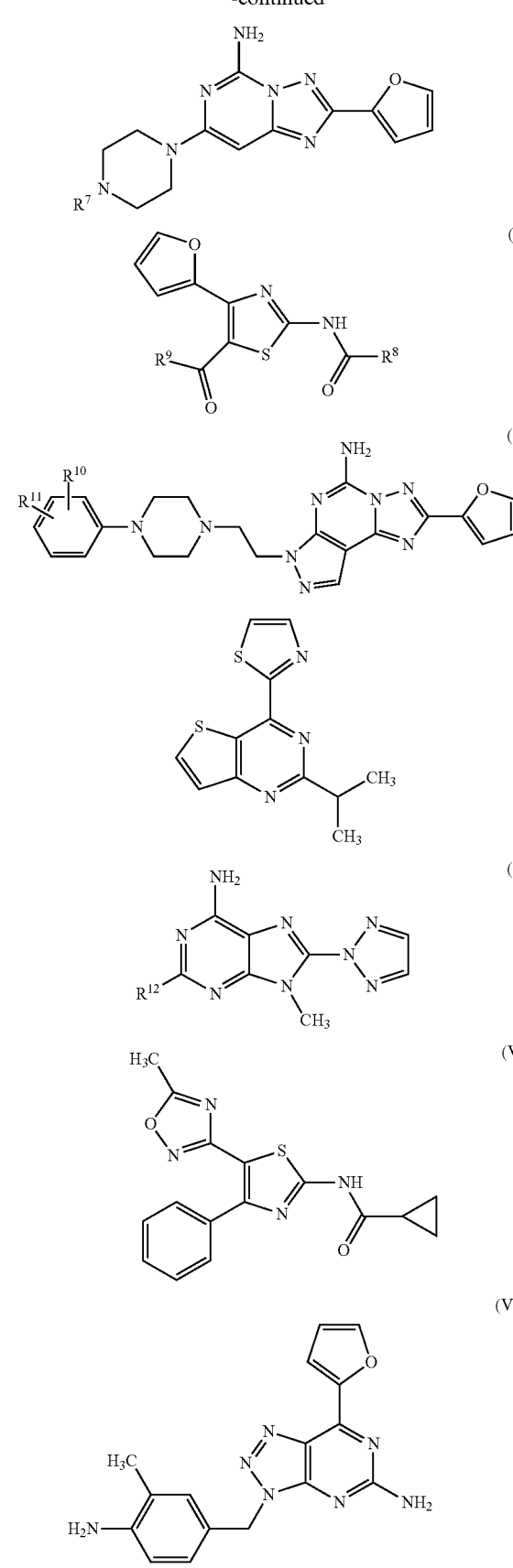

(Wherein, $R^1$, $R^2$, $R^3$, $R^4$, $R^5$, $R^6$, $R^7$, $R^8$, $R^9$, $R^{10}$, $R^{11}$, and $R^{12}$ have the same definitions as described above, respectively.)

(60) The method according to (57) or (58), wherein the compound having adenosine $A_{2A}$ receptor antagonistic activity is a compound represented by the following formula (I), (II), or (III).

[Chemical 34]

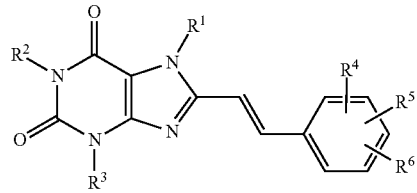

(I)

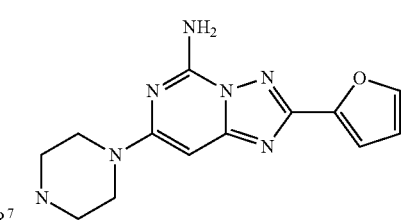

(II)

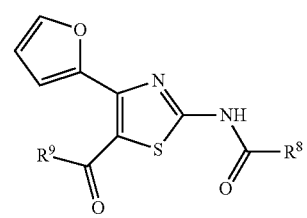

(III)

(Wherein, $R^1$, $R^2$, $R^3$, $R^4$, $R^5$, $R^6$, $R^7$, $R^8$, and $R^9$ have the same definitions as described above, respectively.)

(61) The method according to (57) or (58), wherein the compound having adenosine $A_{2A}$ receptor antagonistic activity is a compound represented by the following formula (IA), (IB), (IC), (ID), (IIA), (IIIB), (IIIC), (IVA), (V), (VIA), (VII), or (VIII).

[Chemical 35]

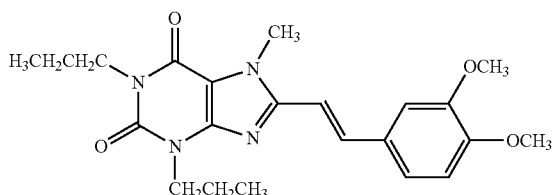

(IA)

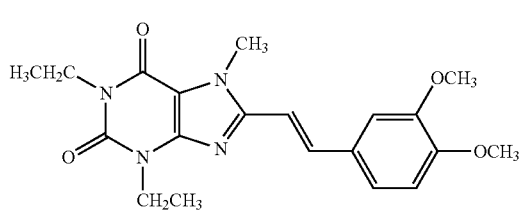

(IB)

-continued

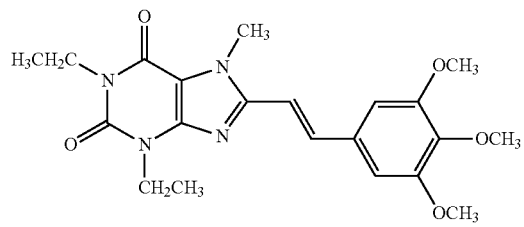
(IC)

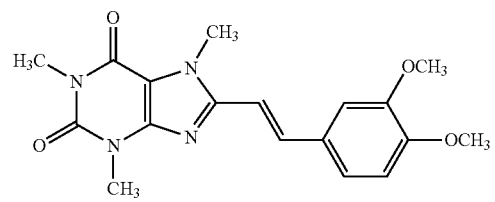
(ID)

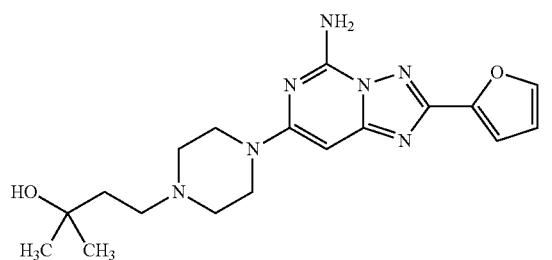
(IIA)

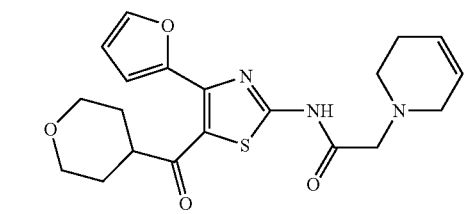
(IIIA)

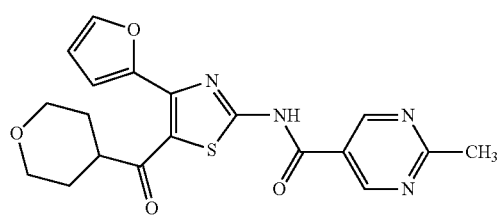
(IIIB)

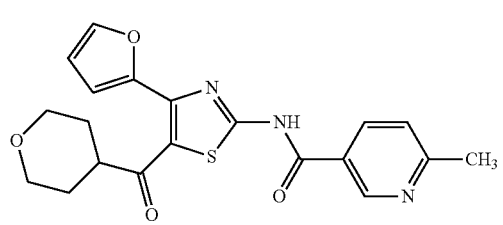
(IIIC)

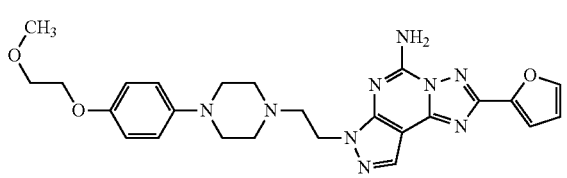
(IVA)

-continued

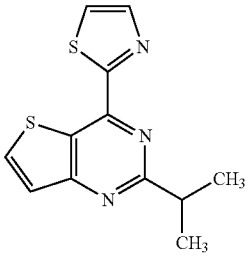
(V)

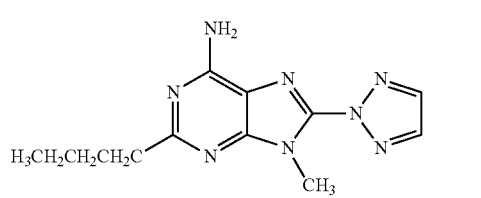
(VIA)

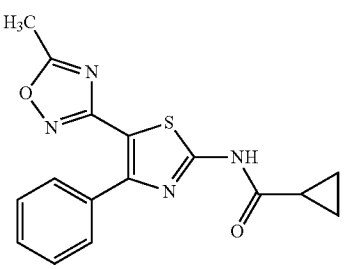
(VII)

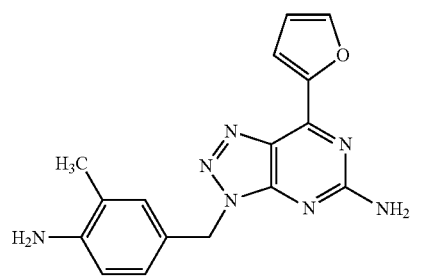
(VIII)

(62) The method according to any one of (57) to (61), wherein the opioid is selected from the group consisting of anileridine, opium, apromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

(63) The method according to any one of (57) to (61), wherein the opioid is morphine.

(64) Use of a compound having adenosine $A_{2A}$ receptor antagonistic activity or a pharmaceutically acceptable salt thereof for the manufacture of a suppressant of an undesirable effect of an opioid.

(65) The use according to (64), wherein the undesirable effect is analgesic tolerance or constipation.

(66) The use according to (64), wherein the undesirable effect is analgesic tolerance.

(67) The use according to any one of (64) to (66), wherein the compound having adenosine $A_{2A}$ receptor antagonistic activity is a compound represented by any one of the following formulae (I) to (VIII).

[Chemical 36]

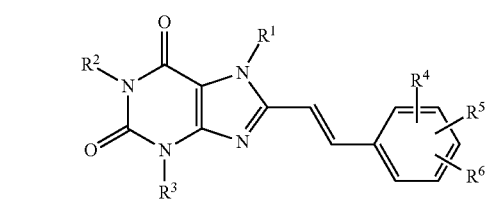
(I)

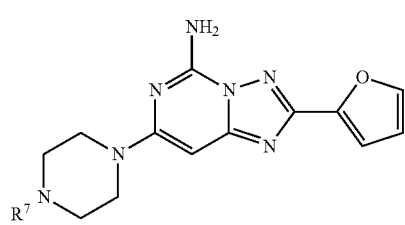
(II)

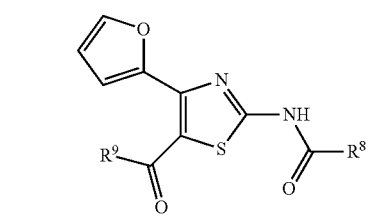
(III)

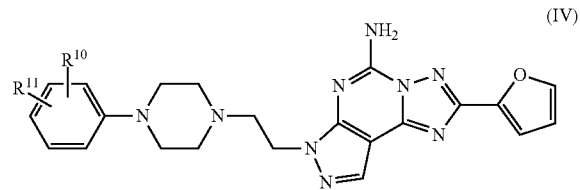
(IV)

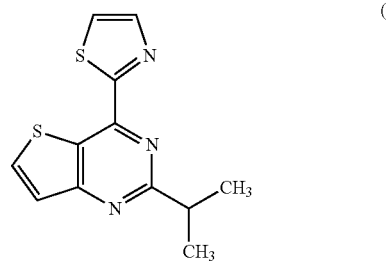
(V)

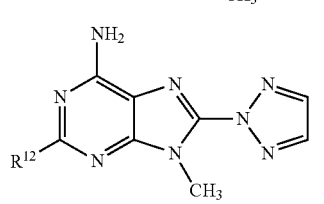
(VI)

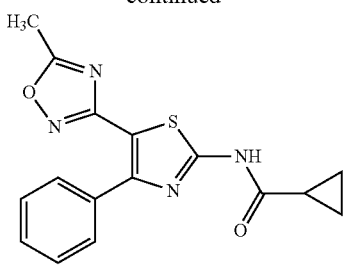
(VII)

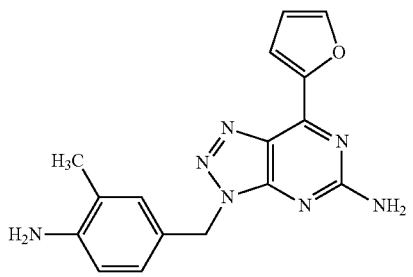
(VIII)

(Wherein, $R^1$, $R^2$, $R^3$, $R^4$, $R^5$, $R^6$, $R^7$, $R^8$, $R^9$, $R^{10}$, $R^{11}$, and $R^{12}$ have the same definitions as described above, respectively.)

(68) The use according to any one of (64) to (66), wherein the compound having adenosine $A_{2A}$ receptor antagonistic activity is a compound represented by the following formula (I), (II), or (III).

[Chemical 37]

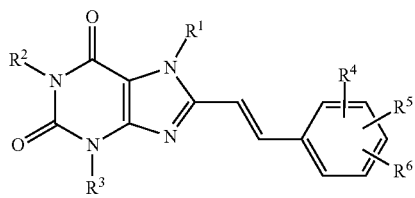
(I)

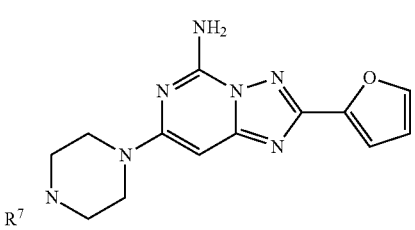
(II)

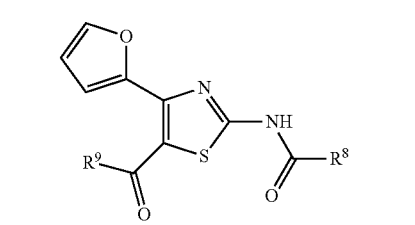
(III)

(Wherein, $R^1$, $R^2$, $R^3$, $R^4$, $R^5$, $R^6$, $R^7$, $R^8$, and $R^9$ have the same definitions as described above, respectively.)

(69) The use according to any one of (64) to (66), wherein the compound having adenosine $A_{2A}$ receptor antagonistic activity is a compound represented by the following formula (IA), (IB), (IC), (ID), (IIA), (IIIA), (IIIB), (IIIC), (IVA), (V), (VIA), (VII), or (VIII).
[Chemical 38]
(IA)
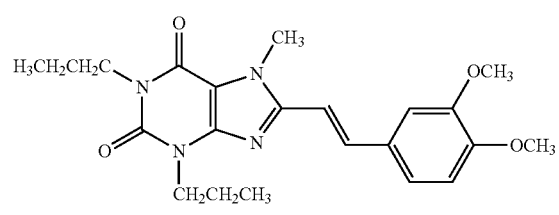
(IB)
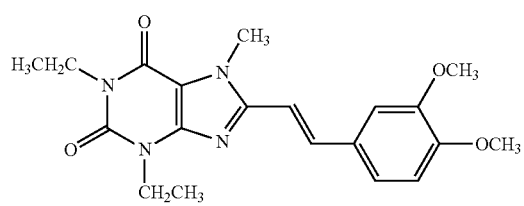
(IC)
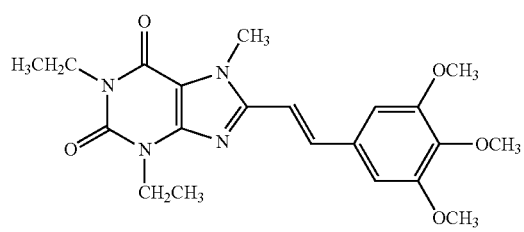
(ID)
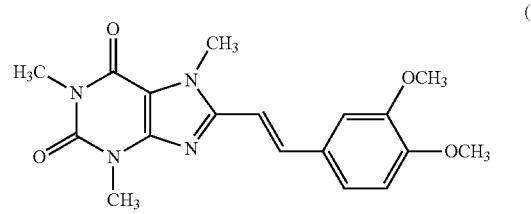
(IIA)
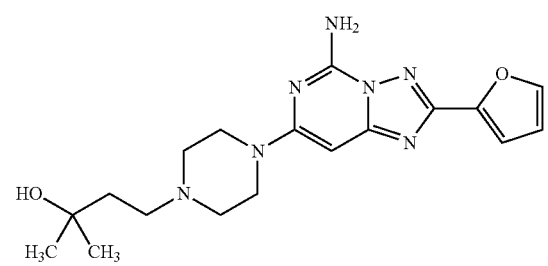
(IIIA)
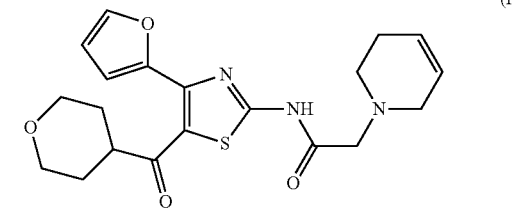
-continued
(IIIB)
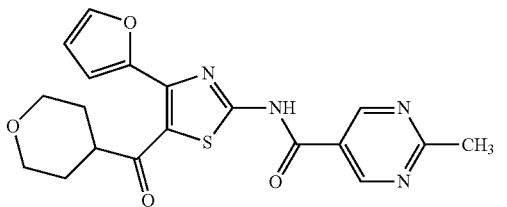
(IIIC)
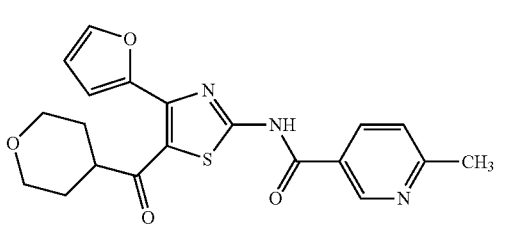
(IVA)
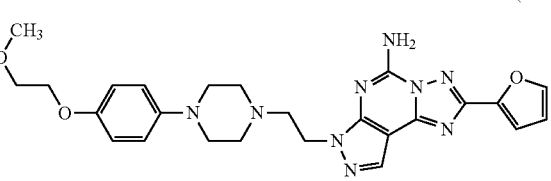
(V)
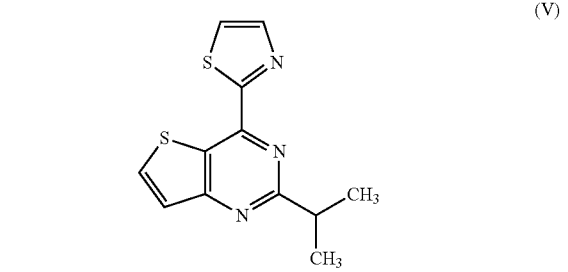
(VIA)
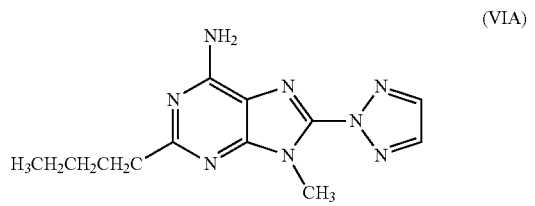
(VII)
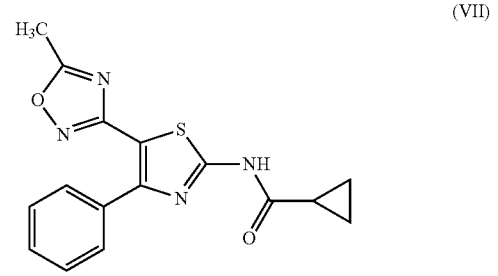

(VIII)

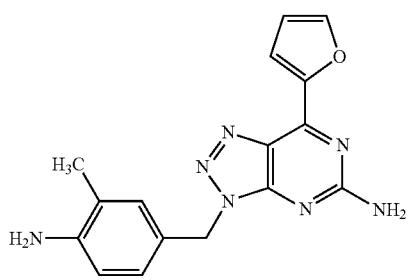

(70) The use according to any one of (64) to (69), wherein the opioid is selected from the group consisting of anileridine, opium, ampromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

(71) The use according to any one of (64) to (69), wherein the opioid is morphine.

(72) Use of (a) a compound having adenosine $A_{2A}$ receptor antagonistic activity or a pharmaceutically acceptable salt thereof and (b) an opioid in combination for the manufacture of a therapeutic and/or preventive agent for pain.

(73) Use of the following (a) and (b) for the manufacture of a therapeutic and/or preventive agent for pain: (a) a compound having adenosine $A_{2A}$ receptor antagonistic activity or a pharmaceutically acceptable salt thereof; and (b) an opioid, both of which are to be administered simultaneously or separately at an interval.

(74) The use according to (72) or (73), wherein the compound having adenosine $A_{2A}$ receptor antagonistic activity is a compound represented by any one of the following formulae (I) to (VIII).

[Chemical 39]

(I)

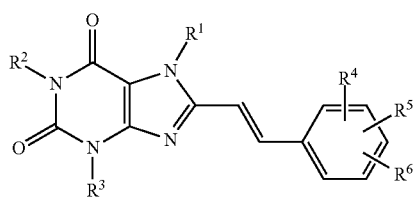

(II)

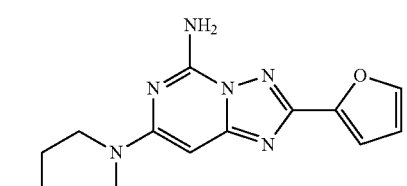

(III)

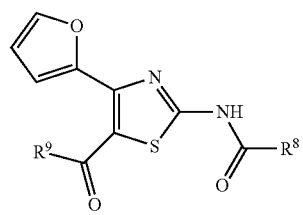

(IV)

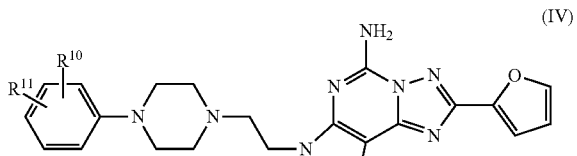

(V)

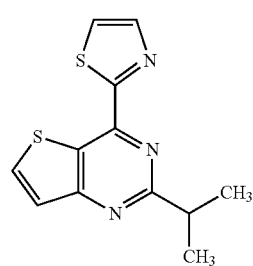

(VI)

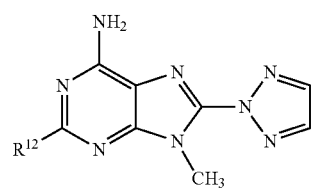

(VII)

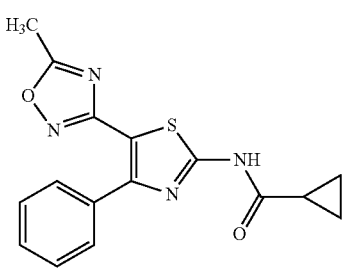

(VIII)

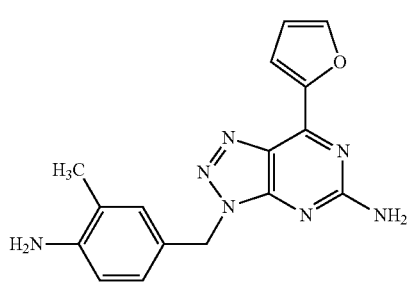

(Wherein, $R^1$, $R^2$, $R^3$, $R^4$, $R^5$, $R^6$, $R^7$, $R^8$, $R^9$, $R^{10}$, $R^{11}$, and $R^{12}$ have the same definitions as described above, respectively.)

(75) The use according to (72) or (73), wherein the compound having adenosine $A_{2A}$ receptor antagonistic activity is a compound represented by the following formula (I), (II), or (III) or a pharmaceutically acceptable salt thereof.

[Chemical 40]

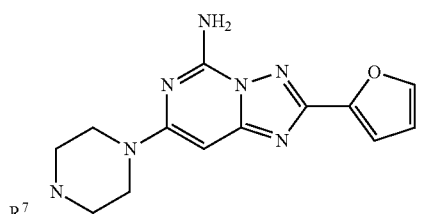
(I)

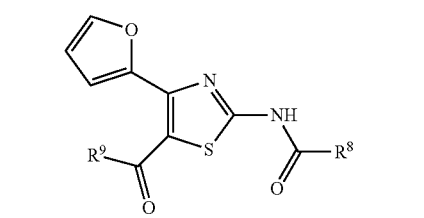
(II)

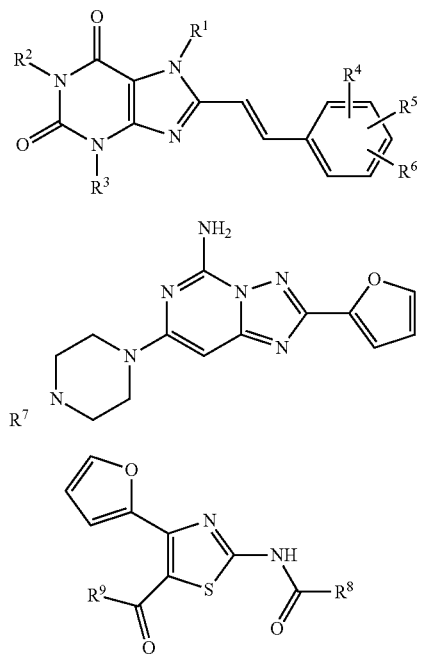
(III)

(Wherein, $R^1$, $R^2$, $R^3$, $R^4$, $R^5$, $R^6$, $R^7$, $R^8$, and $R^9$ have the same definitions as described above, respectively.)

(76) The use according to (72) or (73), wherein the compound having adenosine $A_{2A}$ receptor antagonistic activity is a compound represented by the following formula (IA), (IB), (IC), (ID), (IIA), (IIIA), (IIIB), (IIIC), (IVA), (V), (VIA), (VII), or (VIII).

[Chemical 41]

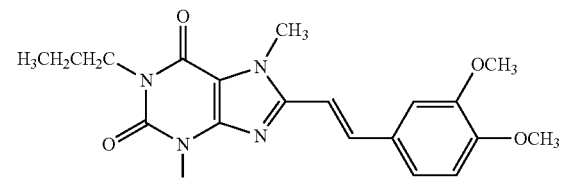
(IA)

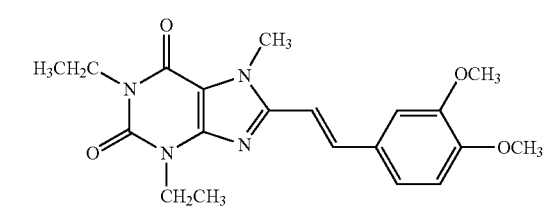
(IB)

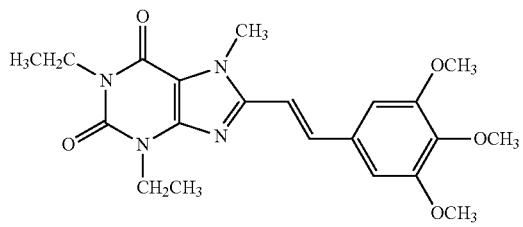
(IC)

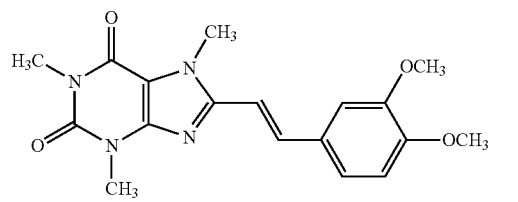
(ID)

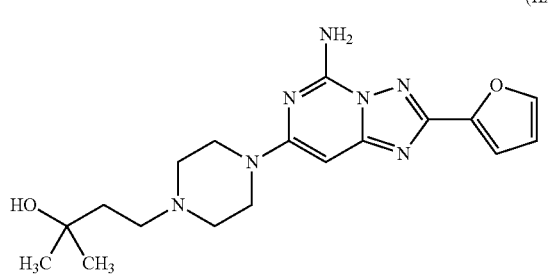
(IIA)

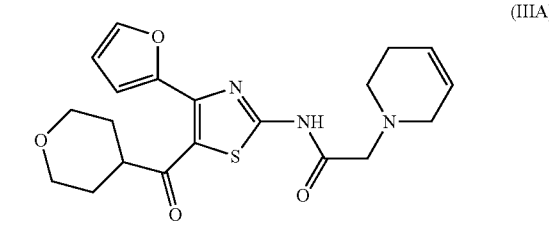
(IIIA)

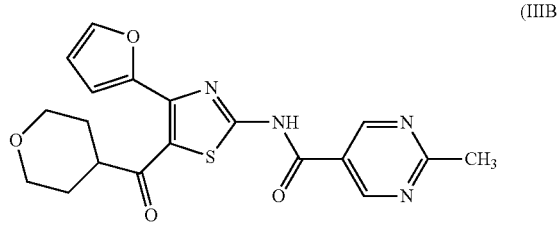
(IIIB)

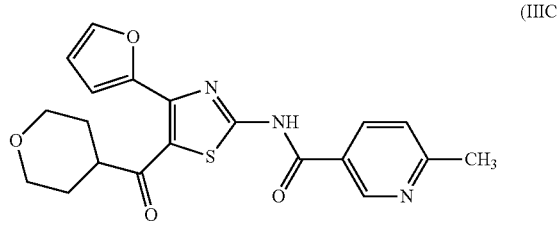
(IIIC)

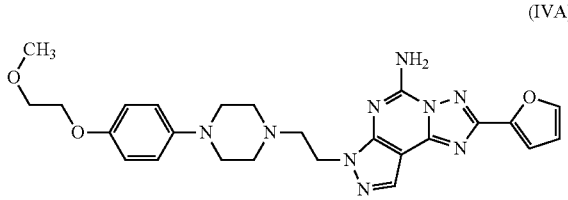
(IVA)

-continued

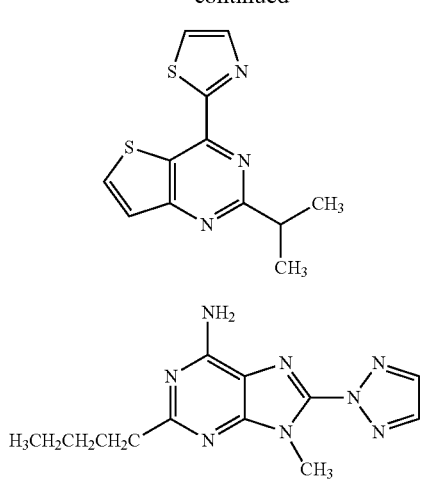

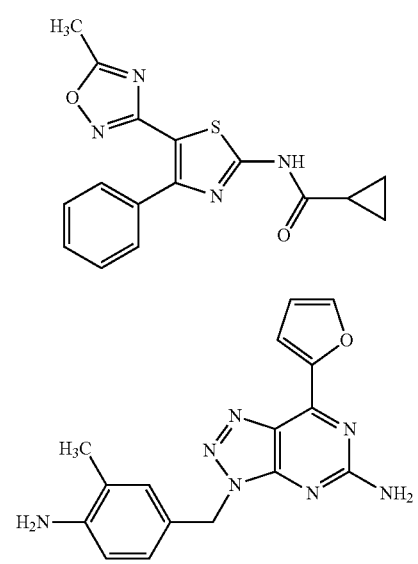

(Wherein, $R^1$, $R^2$, $R^3$, $R^4$, $R^5$, $R^6$, $R^7$, $R^8$, $R^9$, $R^{10}$, $R^{11}$, and $R^{12}$ have the same definitions as described above, respectively.)

(77) The use according to any one of (72) to (76), wherein the opioid is selected from the group consisting of anileridine, opium, ampromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

(78) The use according to any one of (72) to (76), wherein the opioid is morphine.

(79) A compound having adenosine $A_{2A}$ receptor antagonistic activity or a pharmaceutically acceptable salt thereof for use in suppressing an undesirable effect of an opioid.

(80) The compound or a pharmaceutically acceptable salt thereof according to (79), wherein the undesirable effect is analgesic tolerance or constipation.

(81) The compound or a pharmaceutically acceptable salt thereof according to (79), wherein the undesirable effect is analgesic tolerance.

(82) The compound or a pharmaceutically acceptable salt thereof according to any one of (79) to (81), wherein the compound having adenosine $A_{2A}$ receptor antagonistic activity is a compound represented by any one of the following formulae (I) to (VIII).

[Chemical 42]

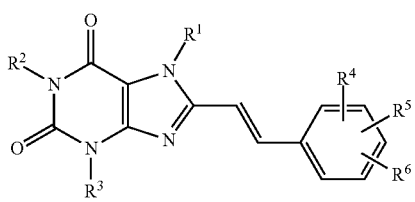

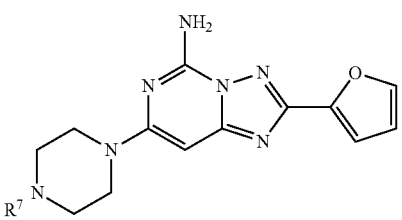

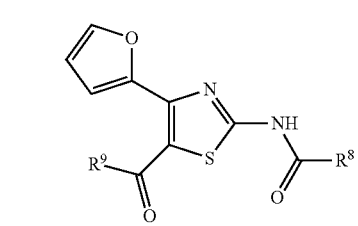

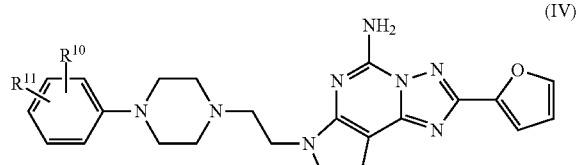

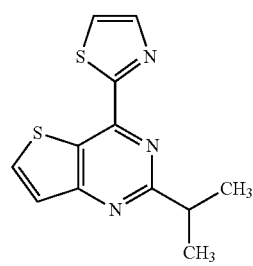

-continued

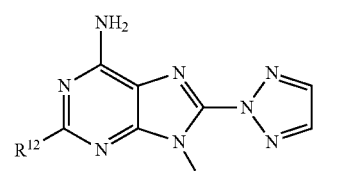
(VI)

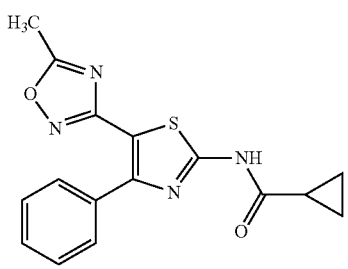
(VII)

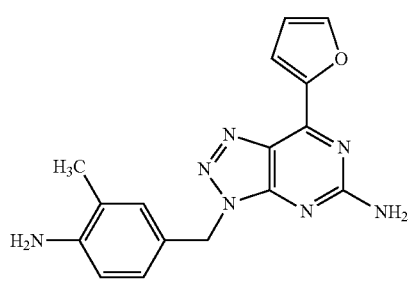
(VIII)

(Wherein, $R^1$, $R^2$, $R^3$, $R^4$, $R^5$, $R^6$, $R^7$, $R^8$, $R^9$, $R^{10}$, $R^{11}$, and $R^{12}$ have the same definitions as described above, respectively.)

(83) The compound or a pharmaceutically acceptable salt thereof according to any one of (79) to (81), wherein the compound having adenosine $A_{2A}$ receptor antagonistic activity is a compound represented by the following formula (I), (II), or (III).

[Chemical 43]

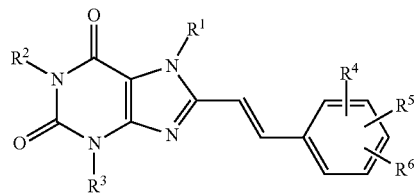
(I)

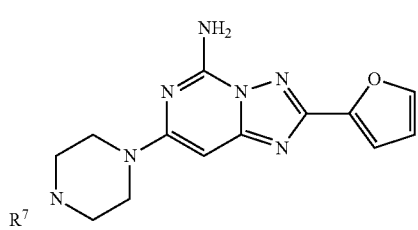
(II)

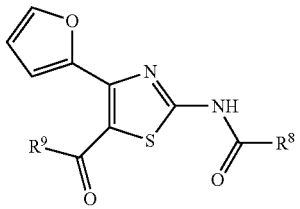
(III)

(Wherein, $R^1$, $R^2$, $R^3$, $R^4$, $R^5$, $R^6$, $R^7$, $R^8$, and $R^9$ have the same definitions as described above, respectively.)

(84) The compound or a pharmaceutically acceptable salt thereof according to any one of (79) to (81), wherein the compound having adenosine $A_{2A}$ receptor antagonistic activity is a compound represented by the following formula (IA), (IB), (IC), (ID), (IIA), (IIIA), (IIIB), (IIIC), (IVA), (V), (VIA), (VII), or (VIII).

[Chemical 44]

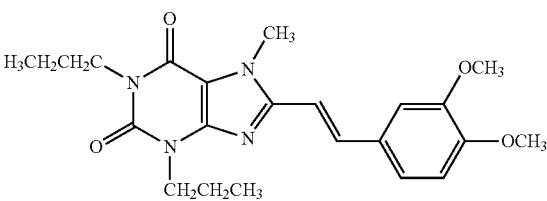
(IA)

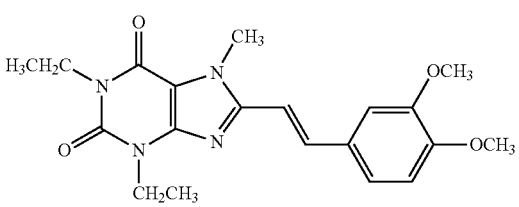
(IB)

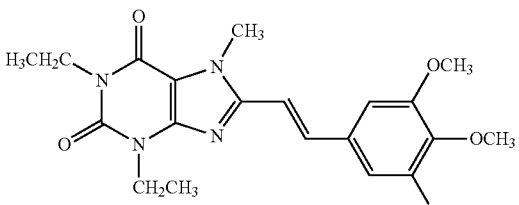
(IC)

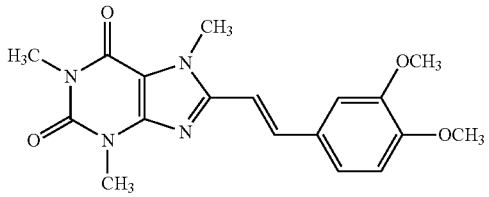
(ID)

-continued (IIA)
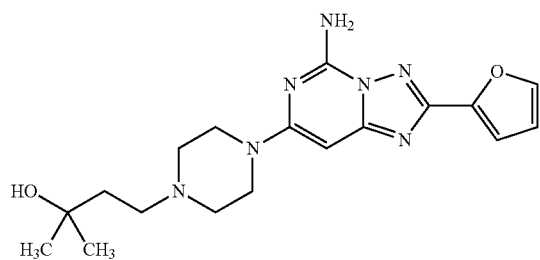

(IIIA)
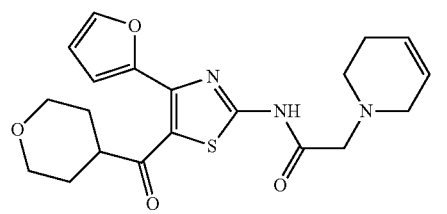

(IIIB)
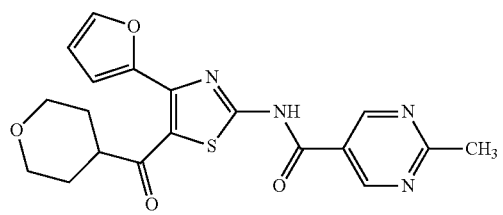

(IIIC)
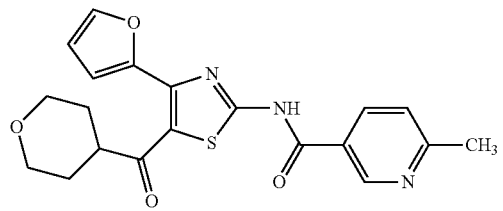

(IVA)
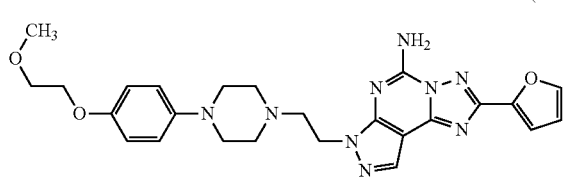

(V)
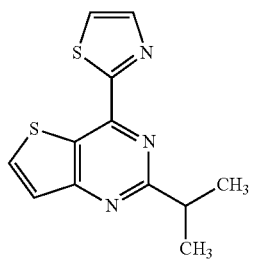

(VIA)
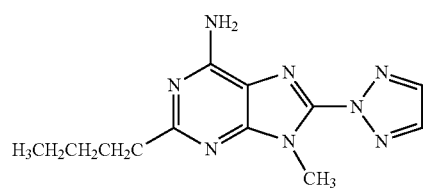

(VII)
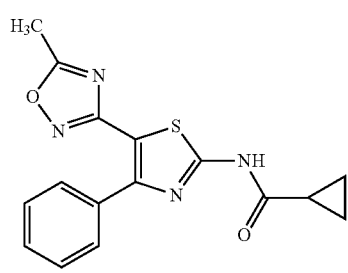

(VIII)
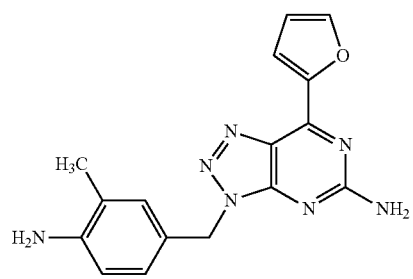

(85) The compound or a pharmaceutically acceptable salt thereof according to any one of (79) to (84), wherein the opioid is selected from the group consisting of anileridine, opium, ampromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

(86) The compound or a pharmaceutically acceptable salt thereof according to any one of (79) to (84), wherein the opioid is morphine.

(87) A combination of (a) a compound having adenosine $A_{2A}$ receptor antagonistic activity or a pharmaceutically acceptable salt thereof and (ID) an opioid for use in treating and/or preventing pain.

(88) A combination of (a) a compound having adenosine $A_{2A}$ receptor antagonistic activity or a pharmaceutically acceptable salt thereof and (b) an opioid for simultaneous or separate-at-an-interval use in treating and/or preventing pain.

(89) The combination according to (87) or (88), wherein the compound having adenosine $A_{2A}$ receptor antagonistic activity is a compound represented by any one of the following formulae (I) to (VIII).

[Chemical 45]

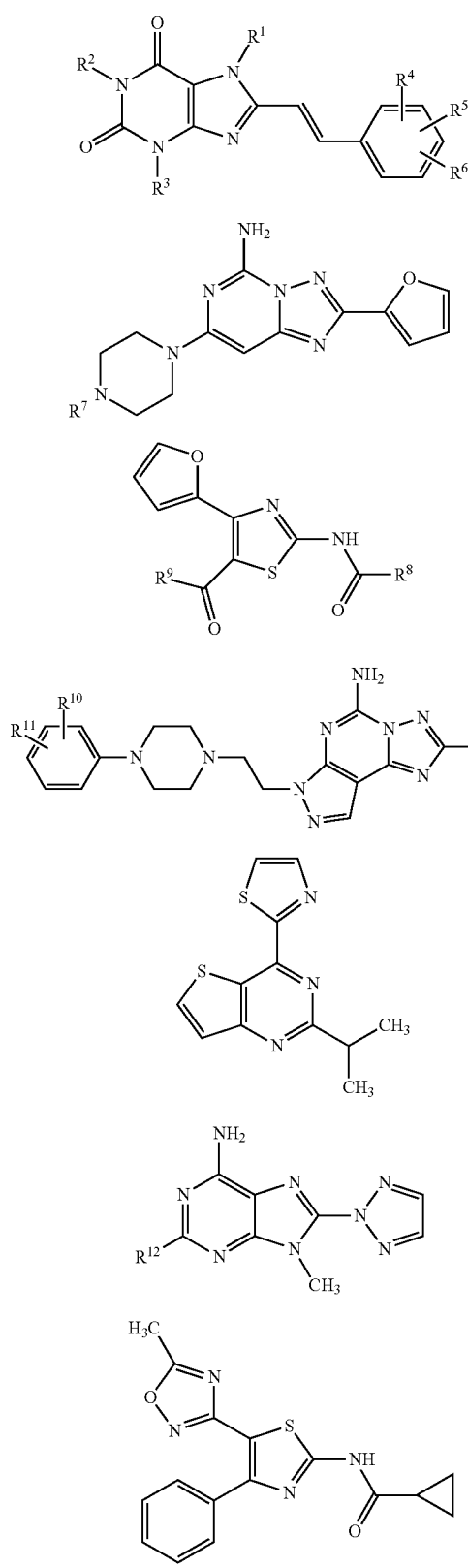

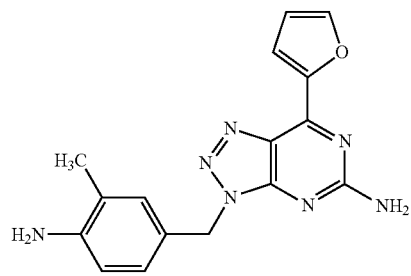

(Wherein, $R^1$, $R^2$, $R^3$, $R^4$, $R^5$, $R^6$, $R^7$, $R^8$, $R^9$, $R^{10}$, $R^{11}$, and $R^{12}$ have the same definitions as described above, respectively.)

(90) The combination according to (87) or (88), wherein the compound having adenosine $A_{2A}$ receptor antagonistic activity is a compound represented by the following formula (I), (II), or (III).

[Chemical 46]

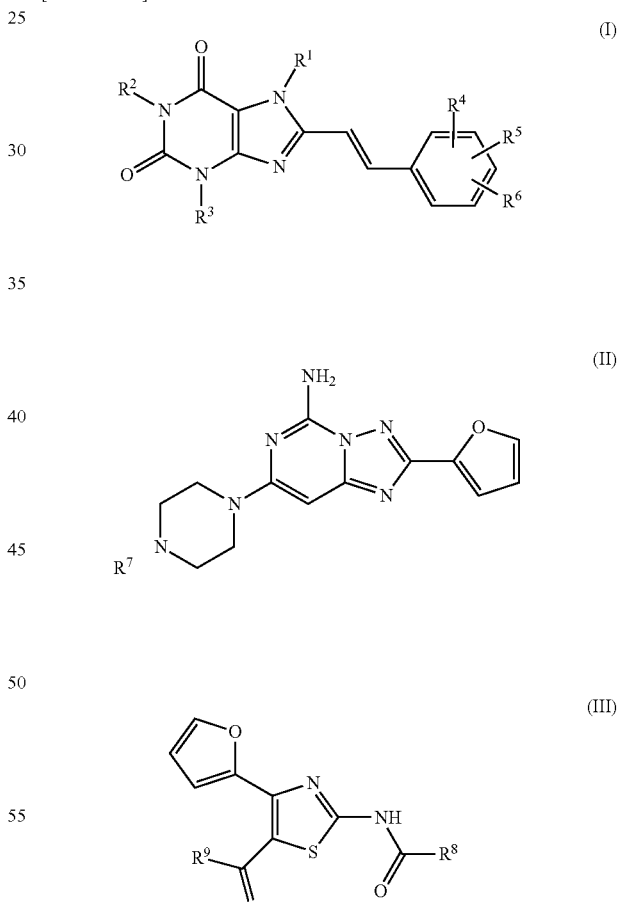

(Wherein, $R^1$, $R^2$, $R^3$, $R^4$, $R^5$, $R^6$, $R^7$, $R^8$, and $R^9$ have the same definitions as described above, respectively.)

(91) The combination according to (87) or (88), wherein the compound having adenosine $A_{2A}$ receptor antagonistic activity is a compound represented by the following formula (IA), (IB), (IC), (ID), (IIA), (IIIA), (IIIC), (IVA), (V), (VIA), (VII), or (VIII).

[Chemical 47]
(IA) 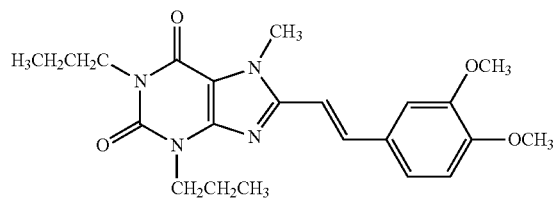
(IB) 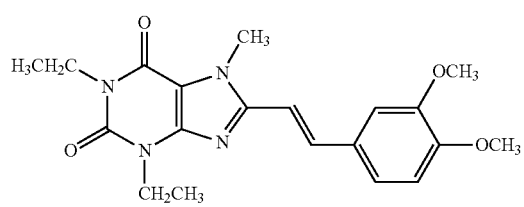
(IC) 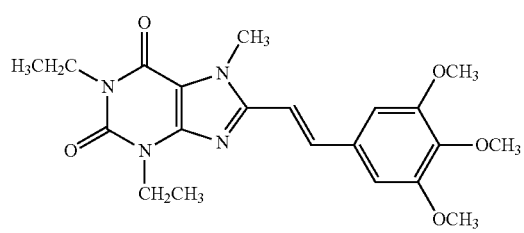
(ID) 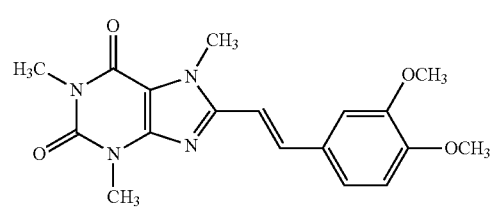
(IIA) 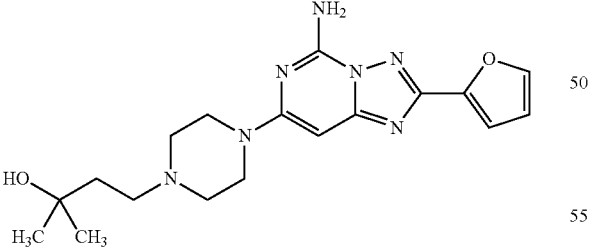
(IIIA) 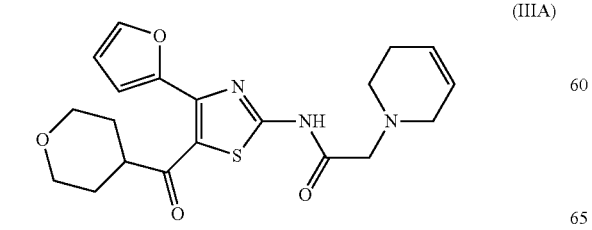
(IIIB) 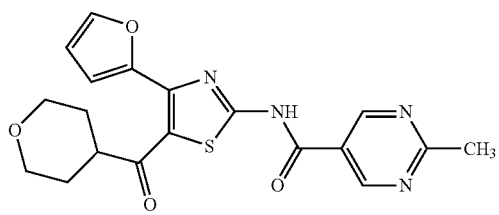
(IIIC) 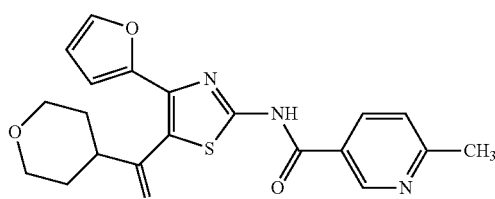
(IVA) 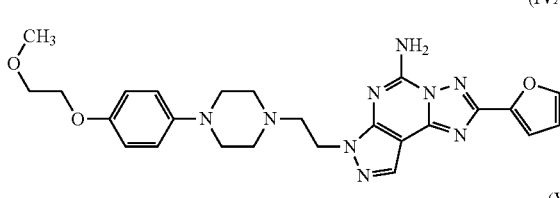
(V) 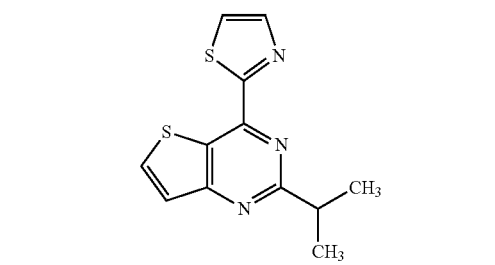
(VIA) 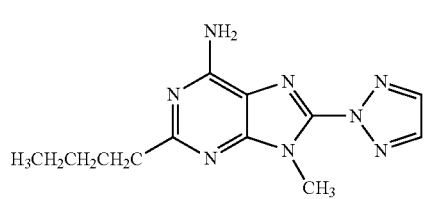
(VII) 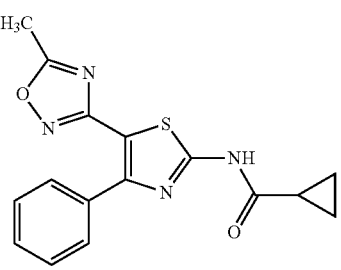
(VIII) 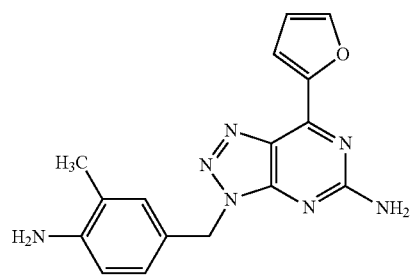

(92) The combination according to any one of (87) to (91), wherein the opioid is selected from the group consisting of anileridine, opium, ampromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

(93) The combination according to any one of (87) to (91), wherein the opioid is morphine.

The Effects of the Present Invention

According to the present invention, an agent for suppressing an undesirable effect (for example, analgesic tolerance, hyperalgesia, constipation, dependence, drowsiness, etc.) of an opioid, which comprises a compound having adenosine $A_{2A}$ receptor antagonistic activity or a pharmaceutically acceptable salt thereof as an active ingredient, and the like can be provided.

DESCRIPTION OF EMBODIMENTS

Figure 1:
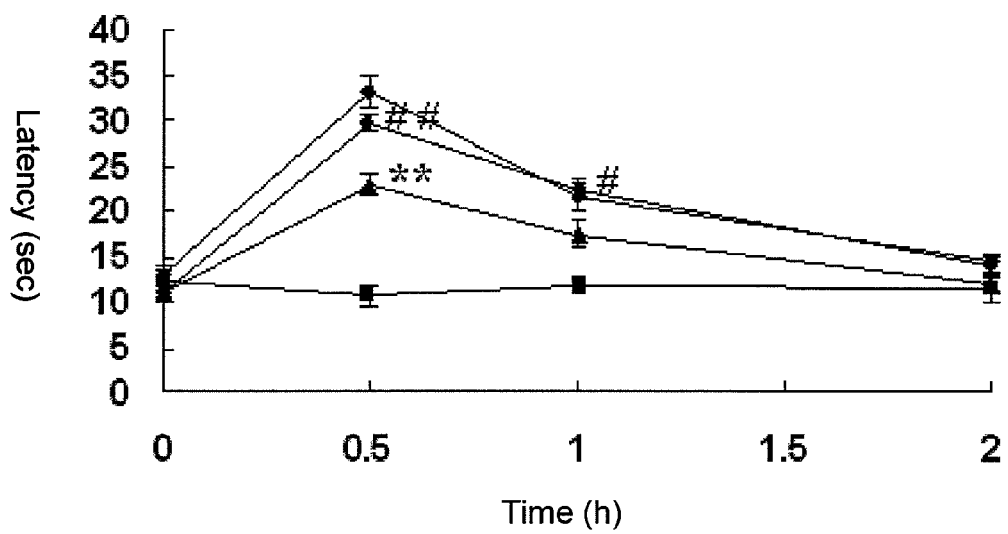
FIG. 1 is a graph showing the effect of Compound (IA) on analgesic tolerance of morphine according to Test Example 1 of the present invention. The vertical axis represents response latency (sec) and the horizontal axis represents time (h) after administration.

The compound having adenosine $A_{2A}$ receptor antagonistic activity of the present invention or to be used in the present invention is not particularly limited as long as it is a compound having adenosine $A_{2A}$ receptor antagonistic activity, however, preferred examples include compounds having selective antagonistic activity against adenosine $A_{2A}$ receptors.

Specifically, for example, a compound represented by any one of the following formulae (I) to (VIII) or a pharmaceutically acceptable salt thereof is preferred:

[Chemical 48]

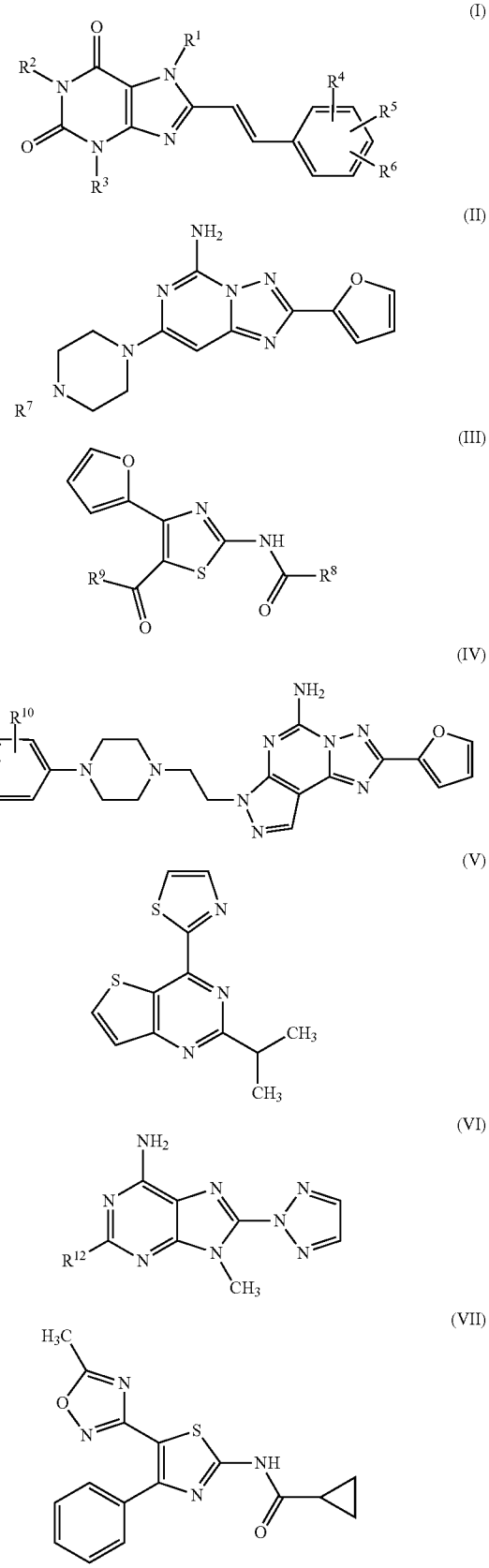

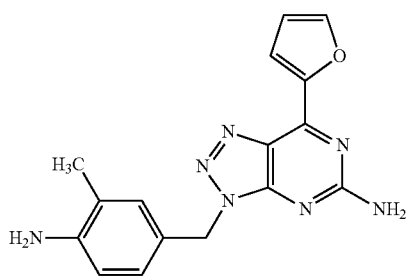

(VIII)

wherein, $R^1$, $R^2$, $R^3$, $R^4$, $R^5$, $R^6$, $R^7$, $R^8$, $R^9$, $R^{10}$, $R^{11}$, and $R^{12}$ have the same definitions as described above, respectively.

More specifically, for example, a compound represented by the following formula (IA), (IB), (IIA), (IIIA), (IIIB), (IIIC), (IVA), (V), (VIA), (VII), or (VIII); or a pharmaceutically acceptable salt thereof is preferred.

[Chemical 49]

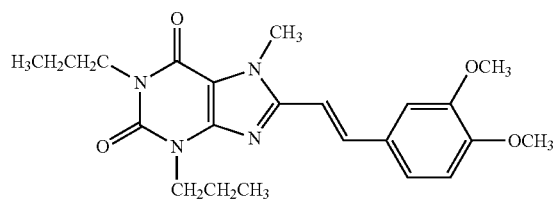

(IA)

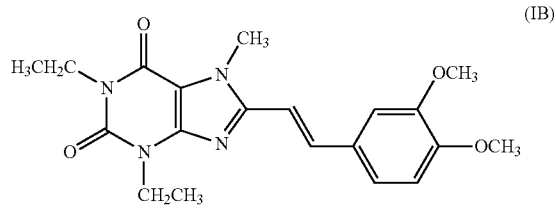

(IB)

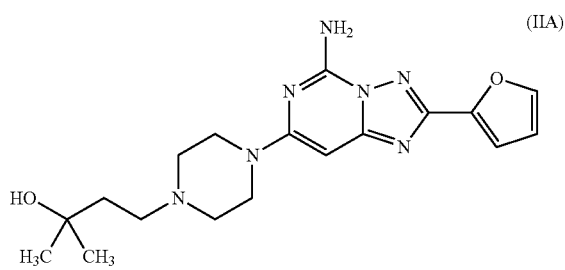

(IIA)

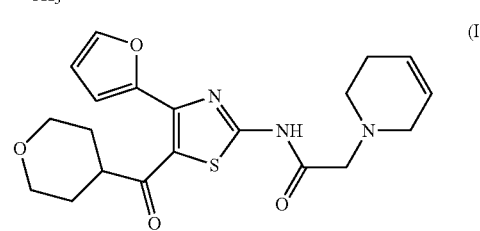

(IIIA)

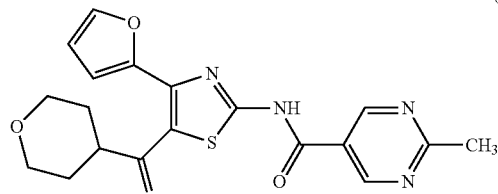

(IIIB)

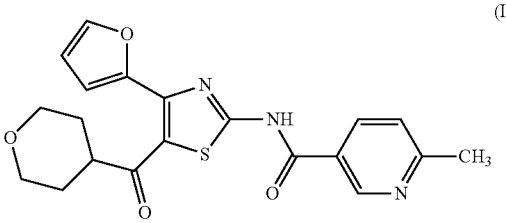

(IIIC)

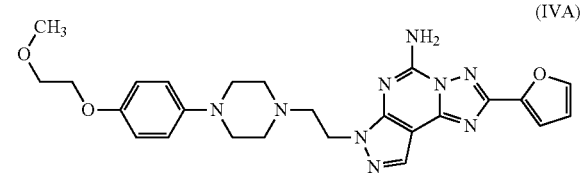

(IVA)

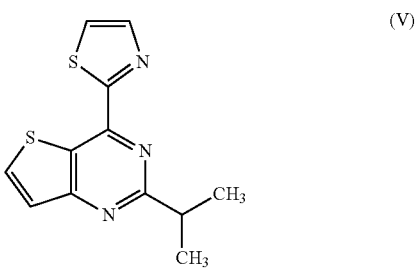

(V)

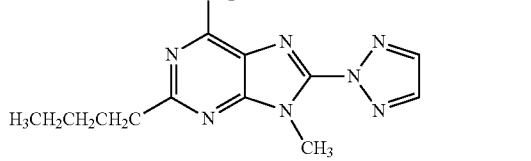

(VIA)

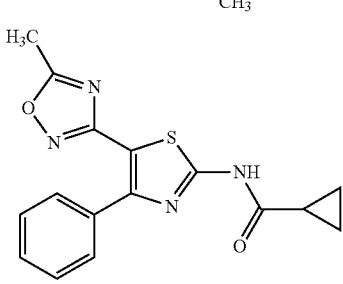

(VII)

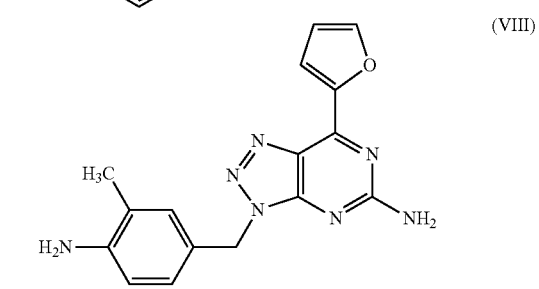

(VIII)

Further more preferably, for example, a compound represented by the following formula (IA) or (IB), or a pharmaceutically acceptable salt thereof is illustrated.

[Chemical 50]

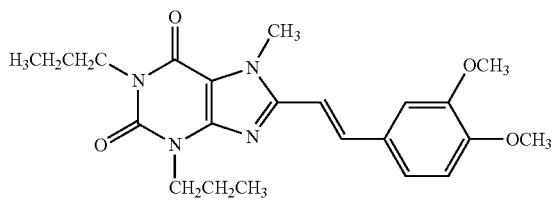

(IA)

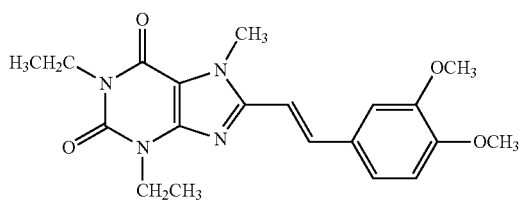

(IB)

Further, for example, a compound represented by the following formula (IIA) or a pharmaceutically acceptable salt thereof is also preferred.

[Chemical 51]

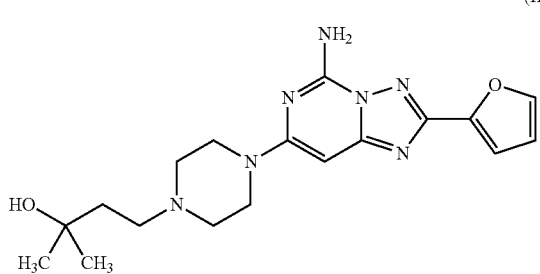

(IIA)

Still further, for example, a compound represented by the following formula (IIIA), (IIIB), or (IIIC) or a pharmaceutically acceptable salt thereof is also preferred.

[Chemical 52]

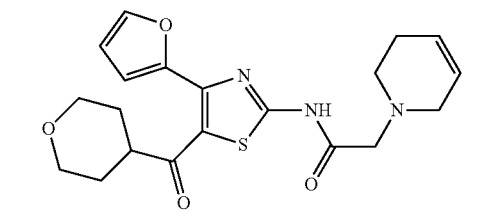

(IIIA)

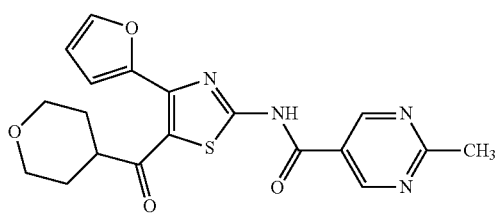

(IIIB)

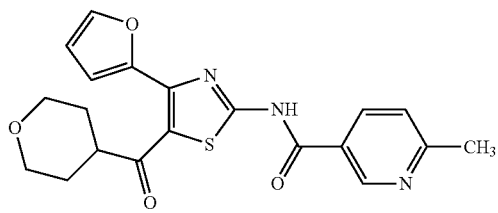

(IIIC)

The compound having adenosine $A_{2A}$ receptor antagonistic activity or a pharmaceutically acceptable salt thereof of the present invention or to be used in the present invention include pharmaceutically acceptable acid addition salts, metal salts, ammonium salts, organic amine addition salts, amino acid addition salts, and the like.

The acid addition salts of the compound having adenosine $A_{2A}$ receptor antagonistic activity of the present invention or to be used in the present invention include, for example, inorganic acid salts such as hydrochloride, sulfate, hydrobromide, nitrate, and phosphate; and organic acid salts such as acetate, mesilate, succinate, maleate, fumarate, citrate, and tartrate. The pharmaceutically acceptable metal salts thereof include, for example, alkali metal salts such as sodium salts and potassium salts; alkaline earth metal salts such as magnesium salts and calcium salts; aluminum salts, zinc salts, and the like. The pharmaceutically acceptable ammonium salts thereof include, for example, salts of ammonium, tetramethylammonium, and the like. The pharmaceutically acceptable organic amine addition salts thereof include, for example, addition salts of morpholine, piperidine, and the like. The pharmaceutically acceptable amino acid addition salts thereof include, for example, addition salts of glycine, phenylalanine, lysine, aspartic acid, glutamic acid, and the like.

The compounds having adenosine $A_{2A}$ receptor antagonistic activity or pharmaceutically acceptable salts thereof of the present invention or to be used in the present invention can be produced according to conventionally known methods, respectively. For example, Compound (I) can be produced by the method described in WO 94/01114, U.S. Pat. No. 5,587,378, J. Med. Chem. 1993, 36, 1333-1342, or the like. Compound (II) can be produced by the method described in WO 00/17201 or the like. Compound (III) can be produced by the method described in WO 2005/063743 or the like. Compound (IV) can be produced by the method described in WO 2001/092264 or the like. Compound (V) can be produced by the method described in WO 2002/055524 or the like. Compound (VI) can be produced by the method described in WO 2003011864 or the like. Compound (VII) can be produced by the method described in WO 2006/032273 or the like. Compound (VIII) can be produced by the method described in WO 2002/055083 or the like.

Some compounds having adenosine $A_{2A}$ receptor antagonistic activity of the present invention or to be used in the present invention may exist in the form of stereoisomers such as geometric isomers and optical isomers, tautomers, or the like. In the agent for suppressing an undesirable effect of an opioid, therapeutic and/or preventive agent for pain, the kit, the pharmaceutical composition, the method for suppressing an undesirable effect of an opioid, the method for treating and/or preventing pain, the use for the manufacture of an agent for suppressing an undesirable effect of an opioid, the use for the manufacture of a therapeutic and/or preventive agent for pain, and the combination of the present invention, any of all possible isomers including the above-mentioned isomers and mixtures thereof can be used, and the compounds having adenosine $A_{2A}$ receptor antagonistic activity of the present invention include all possible isomers including the above-mentioned isomers and mixtures thereof.

In the case where the salt of the compound having adenosine $A_{2A}$ receptor antagonistic activity of the present invention or to be used in the present invention is desired to be obtained, when the respective compounds are obtained in the form of a salt, the compounds may be purified as it is, and when the respective compounds are obtained in the free form, the salt may be obtained by dissolving or suspending each compound in an appropriate solvent and adding an acid or a base thereto, followed by isolation and purification.

Further, some compounds having adenosine $A_{2A}$ receptor antagonistic activity or pharmaceutically acceptable salts thereof of the present invention or to be used in the present invention may exist in the form of an adduct with water or any of various solvents. Any of these adducts can also be used in the agent for suppressing an undesirable effect of an opioid, the therapeutic and/or preventive agent for pain, the kit, the pharmaceutical composition, the method for suppressing an undesirable effect of an opioid, the method for treating and/or preventing pain, the use for the manufacture of an agent for suppressing an undesirable effect of an opioid, the use for the manufacture of a therapeutic and/or preventive agent for pain, and the combination of the present invention.

Examples of the opioid to be used in the present invention include drugs which act on the opioid receptor to exhibit analgesic activity, and specific examples thereof include anileridine, opium, ampromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, remifentanil, and the like. Preferred examples thereof include morphine, fentanyl, oxycodone, and the like, and more preferred examples thereof include morphine and the like. These may be used alone or in combination.

Some of these opioids may exist in the form of a pharmaceutically acceptable salt (the pharmaceutically acceptable salt includes pharmaceutically acceptable acid addition salts, metal salts, ammonium salts, organic amine addition salts, amino acid addition salts, and the like, and examples thereof include inorganic acid salts such as hydrochloride, sulfate, hydrobromide, nitrate, and phosphate; organic acid salts such as acetate, mesilate, succinate, maleate, fumarate, citrate, and tartrate; alkali metal salts such as sodium salts and potassium salts; alkaline earth metal salts such as magnesium salts and calcium salts; metal salts such as aluminum salts and zinc salts; ammonium salts such as ammonium salts and tetramethylammonium salts; organic amine addition salts of morpholine, piperidine, and the like; amino acid addition salts of glycine, phenylalanine, lysine, aspartic acid, glutamic acid, and the like; and the like), a hydrate thereof, or the like. Any of these can also be used in the therapeutic and/or preventive agent for pain, the kit, the pharmaceutical composition, the method for treating and/or preventing pain, the use for the manufacture of a therapeutic and/or preventive agent for pain, and the combination of the present invention.

Further, the opioids illustrated above can be obtained as commercially available products or by producing them according to conventionally known methods.

The agent for suppressing an undesirable effect of an opioid and a compound having adenosine $A_{2A}$ receptor antagonistic activity of the present invention can be used, for example, in combination with any of the above-mentioned opioids, and also, the agent for suppressing an undesirable effect of an opioid, the kit, the pharmaceutical composition, the method for suppressing an undesirable effect of an opioid, and the combination of the present invention can be used for, for example, the treatment and/or prevention of pain. The pain for which the agent for suppressing an undesirable effect of an opioid, the therapeutic and/or preventive agent for pain, the kit, the pharmaceutical composition, the method for suppressing an undesirable effect of an opioid, the method for treating and/or preventing pain, the compound having adenosine $A_{2A}$ receptor antagonistic activity, and the combination of the present invention can be used is not particularly limited, however, examples thereof include pain for which an opioid has been conventionally used for the treatment and/or prevention (for example, chronic pain, etc.), and specific examples thereof include nociceptive pain, neuropathic pain, and the like. More specific examples thereof include nociceptive pain, cancer pain, dorsolumbar pain, pain accompanying traumatic cervical syndrome, traumatic pain, postoperative pain, burn pain, delivery pain, herpes zoster pain, headache, migraine, osteoarticular pain, dorsolumbar pain, rheumatic joint pain, pain accompanying osteoarthritis, fibromyalgia, myofascial pain, visceral pain, inflammatory pain, neuropathic pain, entrapment neuropathy, phantom limb pain, persistent postoperative pain, persistent post-traumatic pain, postherpetic neuralgia, diabetic pain, neurological low back pain, pain after infection with AIDS virus, post-stroke thalamic pain, post-spinal cord injury pain, trigeminal neuralgia, glossopharyngeal neuralgia, and the like, and preferred examples thereof include nociceptive pain, cancer pain, dorsolumbar pain, postoperative pain, herpes zoster pain, osteoarticular pain, dorsolumbar pain, rheumatic joint pain, pain accompanying osteoarthritis, fibromyalgia, myofascial pain, visceral pain, inflammatory pain, neuropathic pain, entrapment neuropathy, postherpetic neuralgia, diabetic pain, neurological low back pain, pain after infection with AIDS virus, post-spinal cord injury pain, trigeminal neuralgia, and the like.

The undesirable effect of an opioid of the present invention refers to symptoms, side effects, and the like, which are problematic when an opioid such as morphine, fentanyl, or oxycodone is administered, and examples thereof include symptoms caused by administering an opioid such as analgesic tolerance, hyperalgesia, dependence, constipation, vomiting, anorexia, drowsiness, wobble, respiratory depression, anxiety, pruritus, paralytic ileus, yawning, sneezing, lacrimation, perspiration, nausea, stomachache, mydriasis, headache, insomnia, delirium, tremor, general myalgia, general joint pain, respiratory distress, withdrawal syndrome, shortness of breath, slow respiration, irregular respiration, abnormal respiration, confusion, pulmonary atelectasis, bronchial spasm, laryngeal edema, toxic megacolon, arrhythmia, change in blood pressure, facial flushing, dizziness, restlessness, excitement, visual accommodation disorder, dry mouth, rash, urination disorder, and intracranial hypertension. By the agent for suppressing an undesirable effect of an opioid or the method for suppressing an undesirable effect of an opioid of the present invention, for example, the above-mentioned symptoms or the like caused by administrating an opioid can be treated and/or prevented. Among them, analgesic tolerance, hyperalgesia, dependence, constipation, vomiting, anorexia, drowsiness, wobble, respiratory depression, anxiety, pruritus, paralytic ileus, and the like, preferably analgesic tolerance, hyperalgesia, dependence, constipation, vomiting, anorexia, drowsiness, and the like, more preferably analgesic tolerance, hyperalgesia, dependence, constipation, and the like, further more preferably analgesic tolerance, hyperalgesia, constipation, and the like, still further more preferably analgesic tolerance, constipation, and the like can be treated and/or prevented.

As for the compound having adenosine $A_{2A}$ receptor antagonistic activity or a pharmaceutically acceptable salt thereof to be used in the agent for suppressing an undesirable effect of an opioid and the method for suppressing an undesirable effect of an opioid of the present invention, the above-mentioned compound having adenosine $A_{2A}$ receptor antagonistic activity or a pharmaceutically acceptable salt thereof can be administered alone as it is, however, in general, it is preferably provided as any of various pharmaceutical preparations. Further, such a pharmaceutical preparation is used for animals or humans.

The pharmaceutical preparations related to the agent for suppressing an undesirable effect of an opioid and the method for suppressing an undesirable effect of an opioid of the present invention can contain a compound having adenosine $A_{2A}$ receptor antagonistic activity or a pharmaceutically acceptable salt thereof as an active ingredient alone or as a mixture with any other active ingredients for any other treatments. Further, these pharmaceutical preparations are produced by mixing the active ingredient with one or more pharmaceutically acceptable carriers (for example, a diluent, a solvent, an excipient, etc.) and then subjecting the mixture to any method well known in the technical field of pharmaceutics.

As for the administration route, it is preferred to use the most effective administration route for the treatment, and examples thereof include oral administration and parenteral administration such as intravenous administration and transdermal administration.

Examples of the dosage form include tablets, injections, suppositories, patches, and the like.

Suitable dosage form for oral administration, for example, a tablet and the like can be produced by using an excipient such as lactose, a disintegrator such as starch, a lubricant such as magnesium stearate, a binder such as hydroxypropyl cellulose, or the like.

Suitable dosage form for parenteral administration, for example, an injection and the like can be produced by using a diluent, a solvent, etc. such as a salt solution, a glucose solution, or a mixed solution of brine and a glucose solution. Also, a suppository, a patch, and the like can be produced by conventionally known methods.

The doses and the frequencies of administration of the compound having adenosine $A_{2A}$ receptor antagonistic activity or a pharmaceutically acceptable salt thereof may vary depending on its dosage form; type; potency; dose and/or dosage form of an opioid used; age and body weight of a patient; nature or seriousness of the symptom to be treated; and the like. However, in the oral administration, in general, a dose of 0.01 to 1000 mg, preferably 0.05 to 100 mg is administered to an adult patient once or several times a day. In the parenteral administration such as intravenous administration, in general, a dose of 0.001 to 1000 mg, preferably 0.01 to 100 mg is administered to an adult patient once or several times a day. However, these doses and frequencies of administration vary depending on the various conditions described above.

The (a) compound having adenosine $A_{2A}$ receptor antagonistic activity or a pharmaceutically acceptable salt thereof and the (b) opioid to be used in the pharmaceutical composition, the therapeutic and/or preventive agent for pain, the method for treating and/or preventing pain, the use for the manufacture of a therapeutic and/or preventive agent for pain, or the combination of the present invention can be used or administered as a single preparation (combination preparation) or as a combination of a plurality of preparations as long as, for example, the formulation is performed along with a pharmaceutically acceptable carrier so that these respective active ingredients are incorporated therein. In particular, a combination of two or more preparations is preferred. When these active ingredients are used or administered as a combination of a plurality of preparations, these active ingredients can be used or administered simultaneously or separately at an interval. Incidentally, these preparations are preferably used in the form of, for example, a tablet, an injection, a suppository, a patch, or the like.

The ratio of the doses (weight/weight) of the (a) compound having adenosine $A_{2A}$ receptor antagonistic activity or a pharmaceutically acceptable salt thereof and the (b) opioid may be appropriately adjusted according to the combination of the (a) compound having adenosine $A_{2A}$ receptor antagonistic activity or a pharmaceutically acceptable salt thereof and the (b) opioid used, the respective potencies of the (a) compound having adenosine A receptor antagonistic activity or a pharmaceutically acceptable salt thereof and the (b) opioid, or the like, however, specifically, the ratio is between 1/100000 ((a) compound having adenosine $A_{2A}$, receptor antagonistic activity or a pharmaceutically acceptable salt thereof/(b) opioid) and 1000/1, preferably between 1/50000 and 500/1, more preferably between 1/6000 and 100/1, further more preferably between 1/4000 and 15/1, still further more preferably between 1/1000 and 10/1, and most preferably between 1/100 and 10/1.

When these active ingredients are administered as a combination of a plurality of preparations, for example, (a) a first component containing a compound having adenosine $A_{2A}$ receptor antagonistic activity or a pharmaceutically acceptable salt thereof and (b) a second component containing an opioid are separately formulated into preparations and prepared as a kit, and the respective components can be administered simultaneously or separately at an interval to the same subject through the same administration route or different administration routes using this kit.

As the kit, for example, a kit comprising contents and two or more containers (for example, vials, bags, etc.) whose material, shape, and so on are not particularly limited as long as the containers do not cause degeneration of the components which are the contents due to external temperature or light nor cause elution of chemical components from the containers during storage, and having a form which enables the administration of the above first and second components which are the contents through separate routes (for example, tubes, etc.) or the same route is used. Specific examples thereof include tablet kits, injection kits, and the like.

As described above, the pharmaceutical composition, the therapeutic and/or preventive agent for pain, or the combination of the present invention can be used, administered, or produced as a single preparation or a combination of a plurality of preparations as long as it is obtained by formulating the (a) compound having adenosine $A_{2A}$ receptor antagonistic activity or a pharmaceutically acceptable salt thereof and the (b) opioid into a preparation so that the respective active ingredients are incorporated therein. The therapeutic and/or preventive agent for pain and the like are preferably in a unit dosage form suitable for oral administration such as a tablet or parenteral administration such as an injection, a suppository, or a patch.

These preparations are produced by mixing the respective active ingredients with one or more pharmaceutically acceptable carriers (for example, a diluent, a solvent, an excipient, etc.) other than these active ingredients, and then subjecting the mixture to any method well known in the technical field of pharmaceutics.

Suitable for oral administration, for example, tablets and the like can be produced by using an excipient such as lactose, a disintegrator such as starch, a lubricant such as magnesium stearate, a binder such as hydroxypropyl cellulose, and the like.

Suitable for parenteral administration, for example, an injection and the like can be produced by using a diluent, a solvent, etc. such as a salt solution, a glucose solution, or a mixed liquid of brine and a glucose solution. Also, a suppository, a patch, and the like can be produced by conventionally known methods.

In the case where the (a) compound having adenosine $A_{2A}$ receptor antagonistic activity or a pharmaceutically acceptable salt thereof and the (b) opioid are used or administered as a combination of a plurality of preparations for the above-mentioned purpose, the doses and the frequencies of administration of the respective active ingredients may vary depending on potencies of the respective active ingredients, dosage form, age, body weight, and symptom of a patient, and the like. However, in general, the (a) compound having adenosine $A_{2A}$ receptor antagonistic activity or a pharmaceutically acceptable salt thereof and the (b) opioid are preferably administered at the following doses per day, respectively.

In the case of oral administration in the form of, for example, tablets, the (a) compound having adenosine $A_{2A}$ receptor antagonistic activity or a pharmaceutically acceptable salt thereof and the (b) opioid are administered at doses of 0.1 to 1000 mg and 0.1 to 10000 mg, preferably 0.1 to 500 mg and 0.1 to 5000 mg, more preferably 0.5 to 500 mg and 1 to 3000 mg, further more preferably 0.5 to 300 mg and 1 to 2000 mg, respectively, to an adult patient generally once or several times a day simultaneously or separately at an interval.

In the case of parenteral administration in the form of, for example, an injection and the like, the (a) compound having adenosine $A_{2A}$ receptor antagonistic activity or a pharmaceutically acceptable salt thereof and the (b) opioid are administered at doses of 0.1 to 1000 mg and 0.1 to 10000 mg, preferably 0.1 to 500 mg and 0.1 to 5000 mg, more preferably 0.5 to 500 mg and 1 to 3000 mg, further more preferably 0.5 to 300 mg and 1 to 2000 mg, respectively, to an adult patient generally once or several times a day simultaneously or separately at an interval.

Further, in the case where the (a) compound having adenosine $A_{2A}$ receptor antagonistic activity or a pharmaceutically acceptable salt thereof and the (b) opioid are used or administered as a single preparation for the above-mentioned purpose, the doses and the frequencies of administration may vary depending on potencies of the respective active ingredients; dosage form; age, body weight, and symptom of a patient; and the like. However, it is preferred that the respective active ingredients is formulated into a single preparation at the same doses as in the above-mentioned case where the respective active ingredients are used and administered as a combination of a plurality of preparations and the resulting single preparation is used or administered.

However, these doses and frequencies of administration vary depending on the above-mentioned various conditions.

Next, the suppressing effect of the compound having adenosine $A_{2A}$ receptor antagonistic activity or a pharmaceutically acceptable salt thereof on an undesirable effect of an opioid, and the effect of the administration of the (a) compound having adenosine $A_{2A}$ receptor antagonistic activity or a pharmaceutically acceptable salt thereof and the (b) opioid in combination will be specifically described in the Test Examples.

TEST EXAMPLE 1

Suppressing Activity of Compound (I) on Morphine Analgesic Tolerance

Experimental Materials and Methods
1. Used Animals

Male ddY mice (3 to 4 weeks old, Japan SW, Inc.) having a body weight of 19 to 25 g were used, and the animals were maintained under the following conditions: 19 to 25° C. room temperature, 30 to 70% humidity, and 12-h light and dark cycle (light period: from 7 a.m. to 7 p.m., dark period: from 7 p.m. to 7 a.m.) until they were subjected to the experiment. Food and water were provided ad libitum.

2. Used Agents and Preparation Methods

Hereinafter, the test was performed under the instructions of narcotics researchers in accordance with the narcotic handling rule each time morphine was used. Morphine was dissolved in physiological saline at a concentration of 0.6 mg/mL and subcutaneously administered at a dose of 6 mg/kg. Compound (IA) was suspended in 0.5% methyl cellulose (0.5% MC) at a concentration of 1 mg/mL and orally administered at a dose of 10 mg/kg.

3. Determination of Analgesic Activity

Nociceptive pain was determined by a hot plate method. Each mouse was placed on a hot plate apparatus (35100, Ugo Basile, Comerio, VA, Italy) set to 53° C., and the time (latency) until an escape response (paw-licking, -biting, -shaking, or jumping) was evoked was determined to be a pain threshold. In the experiment, animals having a response latency of 6 to 16 seconds before the first drug administration were used. Further, in order to minimize the damage to the site of stimulation, the cut-off time was set to 45 seconds. The analgesic activity was evaluated by determining the response latency at 30, 60, and 120 minutes after drug administration on the last day of repeated drug administration (on day 7).

4. Statistical Processing

The experimental results were expressed as mean±standard error. The statistical analysis was performed using a statistical analysis software SAS (SAS Institute Inc., Cary, N.C., USA). Comparison between two groups was performed using a Wilcoxn rank sum test. A p-value of less than 0.05 was considered to be a significant difference.

5. Experimental Results

The results are shown in FIG. 1. In the group in which morphine was repeatedly administered for 7 days (repeated morphine administration group: twice a day, one-time administration only on day 7), the response latency was significantly and markedly decreased as compared with that of the single morphine administration group (physiological saline was repeatedly administered twice a day for 6 days, and morphine was administered only on day 7), and the development of analgesic tolerance was observed. In the repeated combination administration group in which Compound (IA) was orally administered at 30 minutes before administration of morphine, a decrease in analgesic activity was not observed as compared with the single morphine administration group, and the development of analgesic tolerance was prevented. Incidentally, in the group in which Compound (IA) was repeatedly administered alone (repeated Compound (IA) administration group), the effect on the response latency was not observed.

From the above test, it was confirmed that Compound (IA) has a suppressing effect on morphine analgesic tolerance. From this, it was considered that the development of analgesic tolerance following chronic opioid administration can be prevented by using Compound (I) and an opioid in combination.

TEST EXAMPLE 2

Suppressing Activity of Compound (I) on Morphine-Induced Constipation

Experimental Materials and Methods
1. Used Animals

Figure 2:
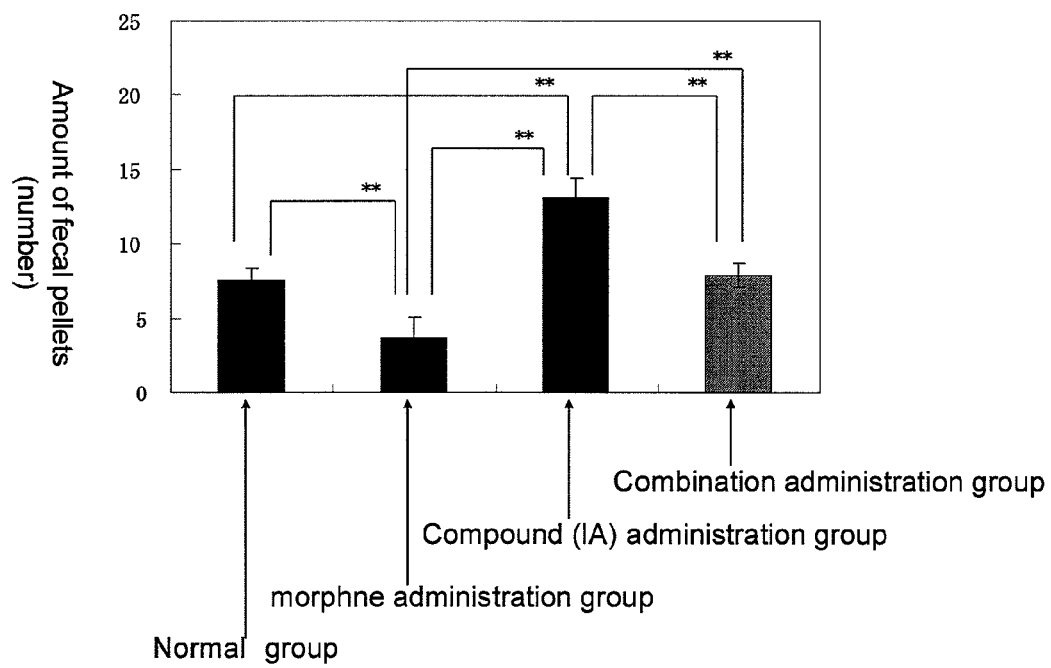
FIG. 2 is a graph showing the effect of Compound (IA) on morphine-induced constipation according to Test Example 2 of the present invention. The vertical axis represents the amount (number) of stools. The bars from left to right represent the results of normal group, morphine administration group, Compound (IA) administration group, and combination administration group, respectively.

Male ddY mice (5 weeks old, Japan SLC, Inc.) having a body weight of 23 to 27 g were used, and the animals were maintained under the following conditions: 19 to 25° C. room temperature, 30 to 70% humidity, and 12-h light and dark cycle (light period: from 7 a.m. to 7 p.m., dark period: from 7 p.m. to 7 a.m.) until they were subjected to the experiment. Food and water were provided ad libitum. At the time of collection of fecal pellets, food and water were not provided.
2. Used Agents and Preparation Methods Morphine was dissolved in physiological saline at a concentration of 0.3 mg/mL and subcutaneously administered at a dose of 3 mg/kg. Compound (IA) was suspended in 0.5% MC at a concentration of 1 mg/mL and orally administered at a dose of 10 mg/kg.
3. Determination of Suppressing Activity on Constipation On the day of the test, the tails of the mice were numbered for identification, and the body weight of each mouse was measured. On the basis of the measured body weight, 0.5% MC or Compound (IA) was orally administered. At 30 minutes after administration of 0.5% MC or Compound (IA), physiological saline or morphine was subcutaneously administered, and collection of fecal pellets was started. The fecal pellets were collected at 3 hours after administration of morphine. The amount of feces was evaluated by counting the number of the fecal pellets.
4. Statistical Processing The experimental results were expressed as mean±standard error. The statistical analysis was performed using a statistical analysis software SAS (SAS Institute Inc., Cary, N.C., USA). Comparison between two groups was performed using a Wilcoxn rank sum test. A p-value of less than 0.05 was considered to be a significant difference.
5. Experimental Results The results are shown in FIG. 2. In the morphine administration group, the number of fecal pellets was significantly decreased as compared with the normal group, and constipation was observed. In the combination administration group in which Compound (IA) was orally administered at 30 minutes before administration of morphine, the number of fecal pellets was significantly increased as compared with the morphine administration group, and a suppressing activity on constipation was observed. Further, in the Compound (IA) administration group in which only Compound (IA) was administered and the combination administration group in which morphine and Compound (IA) were administered, diarrhea was not induced.

From the above test, it was confirmed that Compound (IA) has a suppressing effect on morphine-induced constipation. That is, it was considered that Compound (I) improves morphine-induced constipation and that constipation caused by administration of an opioid can be improved by using Compound (I) and an opioid in combination.

TEST EXAMPLE 3

Suppressing Activity of Compound (III) on Morphine Analgesic Tolerance

Experimental Materials and Methods
1. Used Animals

Male ddY mice (3 to 4 weeks old, Japan SLC, Inc.) having a body weight of 19 to 25 g were used, and the animals were maintained under the following conditions: 19 to 25° C. room temperature, 30 to 70% humidity, and 12-h light and dark cycle (light period: from 7 a.m. to 7 p.m., dark period: from 7 p.m. to 7 a.m.) until they were subjected to the experiment. Food and water were provided ad libitum.
2. Used Agents and Preparation Methods Hereinafter, the test was performed under the instructions of narcotics researchers in accordance with the narcotic handling rule each time morphine was used. Morphine was dissolved in physiological saline at a concentration of 0.6 mg/mL and subcutaneously administered at a dose of 6 mg/kg. Compound (IIIB) was suspended in 0.5% MC at a concentration of 0.3 mg/mL and orally administered at a dose of 3 mg/kg. Compound (IIIC) was suspended in 0.5% MC at a concentration of 0.1 mg/mL and orally administered at a dose of 1 mg/kg.
3. Determination of Analgesic Activity Nociceptive pain was determined by a hot plate method. Each mouse was placed on a hot plate apparatus (35100, Ugo Basile, Comerio, VA, Italy) set to 53° C., and the time (latency) until an escape response (paw-licking, -biting, -shaking, or jumping) was evoked was determined to be a pain threshold. In the experiment, animals having a response latency of 6 to 16 seconds before the first drug administration were used. Further, in order to minimize the damage to the site of stimulation, the cut-off time was set to 45 seconds. The analgesic activity was evaluated by determining the response latency before drug administration, and at 30, 60, and 120 minutes after drug administration, on the last day of repeated drug administration (on day 7).
4. Statistical Processing The experimental results were expressed as mean±standard error. The statistical analysis was performed using a statistical analysis software SAS (SAS Institute Inc., Cary, N.C., USA). Comparison between two groups was performed using a Wilcoxn rank sum test. A p-value of less than 0.05 was considered to be a significant difference.

5. Experimental Results

The results are shown in Tables 1 and 2.

TABLE 1

Effect of Compound (IIIB) on Morphine Analgesic Tolerance (Response Latency (sec))

| Latency (sec) | Pre value (before drug administration) on last day | ΔChange (Latency at each time point − Pre value) | | |
|---|---|---|---|---|
| | | 0.5 h | 1 h | 2 h |
| Single morphine administration group | 11.4 ± 0.8 | 21.9 ± 1.9 | 11.8 ± 1.1 | 2.9 ± 0.9 |
| Repeated morphine administration group | 9.3 ± 0.6 | 11.4 ± 1.3 ** | 8.5 ± 0.8 * | 3.4 ± 0.7 |
| Repeated combination administration group | 9.6 ± 0.3 | 18.2 ± 1.2 ## | 13.5 ± 0.8 ## | 4.8 ± 0.7 |
| Repeated Compound (IIIB) administration group | 10.7 ± 0.7 | 0.1 ± 0.5 | −0.1 ± 0.4 | 0.4 ± 1.2 |

** $P < 0.01$,
* $P < 0.05$ [Single morphine administration group vs. Repeated morphine administration group]
$P < 0.01$ [Repeated morphine administration group vs. Repeated combination administration group]

TABLE 2

Effect of Compound (IIIC) on Morphine Analgesic Tolerance (Response Latency (sec))

| Latency (sec) | Pre value (before drug administration) on last day | ΔChange (Latency at each time point − Pre value) | | |
|---|---|---|---|---|
| | | 0.5 h | 1 h | 2 h |
| Single morphine administration group | 10.7 ± 0.7 | 20.2 ± 1.9 | 6.3 ± 1.7 | 2.3 ± 0.5 |
| Repeated morphine administration group | 10.8 ± 0.7 | 7.7 ± 1.3 ** | 3.7 ± 1.0 | 1.7 ± 0.7 |
| Repeated combination administration group | 10.9 ± 0.7 | 16.1 ± 2.4 # | 9.3 ± 1.6 # | 1.9 ± 0.9 |
| Repeated Compound (IIIC) administration group | 12.4 ± 1.0 | −2.2 ± 1.3 | −1.0 ± 0.7 | −1.0 ± 0.9 |

** $P < 0.01$ [Single morphine administration group vs. Repeated morphine administration group]
$P < 0.05$ [Repeated morphine administration group vs. Repeated combination administration group]

In the group in which morphine was repeatedly administered for 7 days (repeated morphine administration group: twice a day, one-time administration only on day 7), the response latency was significantly and markedly decreased as compared with that of the single morphine administration group (physiological saline was repeatedly administered twice a day for 6 days, and morphine was administered only on day 7), and the development of analgesic tolerance was observed. In the repeated combination administration group in which Compound (IIIB) or (IIIC) was orally administered at 30 minutes before administration of morphine (repeated combination administration group: Compound (IIIB) or (IIIC) was administered at 30 minutes before each administration of morphine in repeated morphine administration group), a decrease in analgesic activity was not observed as compared with the single morphine administration group, and the development of analgesic tolerance was prevented. Incidentally, in the group in which Compound (IIIB) or (IIIC) was repeatedly administered alone (repeated Compound (IIIB) administration group, repeated Compound (IIIC) administration group), the effect on the response latency was not observed.

From the above test, it was confirmed that Compounds (MB) and (IIIC) have a suppressing effect on morphine analgesic tolerance. From this, it was considered that the development of analgesic tolerance following chronic opioid administration can be prevented by using Compound (III) such as Compound (IIIB) or (IIIC) and an opioid in combination.

TEST EXAMPLE 4

Suppressing Activity of Compounds (IC) and (ID) on Morphine Analgesic Tolerance

The effect of Compounds (IC) and (ID) on morphine analgesic tolerance was studied. The experiment was performed in the same manner as in Test Example 3. Compounds (IC) and (ID) were used at a dose of 10 mg/kg, respectively. The results are shown in Table 3. In the statistical analysis, comparison between two groups was performed using a Wilcoxn rank sum test, and comparison among multi-groups was performed using a Kruskal-Wallis test.

From the above test, it was confirmed that Compounds (IC) and (ID) have a suppressing effect on morphine analgesic tolerance. From the results of this test and Test Example 1, it was considered that the development of analgesic tolerance following chronic opioid administration can be prevented by using Compound (I) such as Compound (IA), (IB), (IC), or (ID) and an opioid in combination.

TABLE 3

Effect of Compounds (IC) and (ID) on Morphine Analgesic Tolerance (Response Latency (sec))

| Latency (sec) | Pre value (before drug administration on last day) | ΔChange (Latency at each time point − Pre value) | | |
|---|---|---|---|---|
| | | 0.5 h | 1 h | 2 h |
| Single morphine administration group | 12.8 ± 1.5 | 19.5 ± 2.0 | 6.4 ± 1.5 | −0.8 ± 1.5 |
| Repeated morphine administration group | 10.5 ± 1.4 | 7.5 ± 1.3 ** | 1.7 ± 1.5 ** | 1.2 ± 1.4 |
| Repeated combination administration group (Compound (IC) and morphine) | 11.4 ± 1.2 | 16.0 ± 1.8 ## | 5.1 ± 1.7 | 0.9 ± 1.3 |
| Repeated combination administration group (Compound (ID) and morphine) | 12.2 ± 1.4 | 14.3 ± 1.7 ## | 5.1 ± 1.3 # | −0.1 ± 1.4 |
| Repeated Compound (IC) administration group | 9.8 ± 0.8 | 1.0 ± 0.7 | 3.3 ± 1.2 | 1.7 ± 0.7 |
| Repeated Compound (ID) administration group | 9.5 ± 0.7 | 2.1 ± 0.8 | 2.3 ± 1.3 | 2.5 ± 0.9 |

** $P < 0.01$ [Single morphine administration group vs. Repeated morphine administration group]
$P < 0.01$, # $P < 0.05$ [Repeated morphine administration group vs. Repeated combination administration group]

In the group in which morphine was repeatedly administered for 7 days (repeated morphine administration group: twice a day, one-time administration only on day 7), the response latency was significantly and markedly decreased as compared with the single morphine administration group (physiological saline was repeatedly administered twice a day for 6 days, and morphine was administered only on day 7), and the development of analgesic tolerance was observed. In the repeated combination administration group in which Compound (IC) or (ID) was orally administered at 30 minutes before administration of morphine (repeated combination administration group: Compound (IC) or (ID) was administered at 30 minutes before each administration of morphine in repeated morphine administration group), the degree of the decrease in response latency was smaller as compared with that of the repeated morphine administration group, and the development of analgesic tolerance was prevented. Incidentally, in the group in which Compound (IC) or (ID) was repeatedly administered alone (repeated Compound (IC) administration group, repeated Compound (ID) administration group), the effect on the response latency was not observed.

TEST EXAMPLE 5

Suppressing Activity of Compounds (IIA), (VIA), and (VII) on Morphine Analgesic Tolerance The effect of Compounds (IIA), (VIA), and (VII) on morphine analgesic tolerance was studied. The experiment was performed in the same manner as in Test Example 3. Compounds (IIA), (VIA), and (VII) were used at doses of 100 mg/kg, 30 mg/kg, and 60 mg/kg, respectively. The results are shown in Table 4. In the statistical analysis, comparison between two groups was performed using a Wilcoxn rank sum test, and comparison among multi-groups was performed using a Kruskal-Wallis test.

TABLE 4

Effect of Compounds (IIA), (VIA), and (VII) on Morphine Analgesic Tolerance (Response Latency (sec))

| Latency (sec) | Pre value (before drug administration on last day) | ΔChange (Latency at each time point − Pre value) | | |
|---|---|---|---|---|
| | | 0.5 h | 1 h | 2 h |
| Single morphine administration group | 8.8 ± 0.6 | 16.8 ± 2.7 | 10.4 ± 2.2 | 8.8 ± 0.6 |
| Repeated morphine administration group | 9.1 ± 0.9 | 7.3 ± 1.2 * | 5.4 ± 1.3 | 2.7 ± 0.8 |
| Repeated combination administration group (Compound (IIA) and morphine) | 8.2 ± 0.5 | 12.8 ± 1.9 | 6.4 ± 1.7 | 2.4 ± 1.2 |
| Repeated combination administration group (Compound (VIA) and morphine) | 8.6 ± 1.1 | 13.0 ± 2.4 | 7.6 ± 1.7 | 1.9 ± 1.3 |
| Repeated combination administration group (Compound (VII) and morphine) | 8.2 ± 0.5 | 12.8 ± 2.1 | 7.8 ± 1.3 | 1.8 ± 0.8 |
| Repeated Compound (VII) administration group | 9.9 ± 0.6 | −0.8 ± 1.0 | −0.7 ± 1.0 | 0.0 ± 0.6 |
| Repeated Compound (VIA) administration group | 9.7 ± 1.1 | −0.8 ± 1.3 | 0.2 ± 2.1 | −0.2 ± 1.1 |
| Repeated Compound (IIA) administration group | 9.0 ± 0.7 | 1.2 ± 1.5 | 1.7 ± 1.4 | 0.9 ± 1.1 |

* $P < 0.05$ [Single morphine administration group vs. Repeated morphine administration group]

In the group in which morphine was repeatedly administered for 7 days (repeated morphine administration group: twice a day, one-time administration only on day 7), the response latency was significantly and markedly decreased as compared with that of the single morphine administration group (physiological saline was repeatedly administered twice a day for 6 days, and morphine was administered only on day 7), and the development of analgesic tolerance was observed. In the repeated combination administration group in which Compound (IIA), (VIA), or (VII) was orally administered at 30 minutes before administration of morphine (repeated combination administration group: Compound (IIA), (VIA), or (VII) was administered at 30 minutes before each administration of morphine in repeated morphine administration group), the degree of the decrease in response latency was smaller as compared with that of the repeated morphine administration group, and the development of analgesic tolerance was prevented. Incidentally, in the group in which Compound (IIA), (VIA), or (VII) was repeatedly administered alone (repeated Compound (IIA) administration group, or repeated Compound (VIA) administration group, repeated Compound (VII) administration group), the effect on the response latency was not observed.

From the above test, it was confirmed that Compounds (IIA), (VIA), and (VII) have a suppressing effect on morphine analgesic tolerance. From the results of this test, it was considered that the development of analgesic tolerance following chronic opioid administration can be prevented by using Compound (II) such as Compound (IIA), Compound (VI) such as Compound (VIA), or Compound (VII) and an opioid in combination.

TEST EXAMPLE 6

Suppressing Activity of Compounds (IVA) and (VIII) on Morphine Analgesic Tolerance The effect of Compounds (IVA) and (VIII) on morphine analgesic tolerance was studied. The experiment was performed in the same manner as in Test Example 3. Compounds (IVA) and (VIII) were used at a dose of 30 mg/kg, respectively. The results are shown in Table 5. In the statistical analysis, comparison between two groups was performed using a Wilcoxn rank sum test, and comparison among multi-groups was performed using a Kruskal-Wallis test.

TABLE 5

Effect of Compounds (IVA) and (VIII) on Morphine Analgesic Tolerance (Response Latency (sec))

| Latency (sec) | Pre value (before drug administration on last day) | ΔChange (Latency at each time point − Pre value) | | |
|---|---|---|---|---|
| | | 0.5 h | 1 h | 2 h |
| Single morphine administration group | 12.4 ± 1.0 | 18.0 ± 2.2 | 6.8 ± 1.3 | 1.9 ± 1.0 |
| Repeated morphine administration group | 12.0 ± 1.1 | 6.8 ± 1.3 ** | 3.1 ± 1.0 ** | 0.4 ± 0.9 |
| Repeated combination administration group (Compound (IVA) and morphine) | 11.7 ± 0.9 | 14.9 ± 1.6 ## | 8.3 ± 0.4 ## | 0.7 ± 1.1 |
| Repeated combination administration group (Compound (VIII) and morphine) | 12.3 ± 0.8 | 13.6 ± 1.6 ## | 7.8 ± 0.8 ## | 1.1 ± 0.8 |
| Repeated Compound (IVA) administration group | 12.6 ± 1.2 | 0.5 ± 0.6 | −0.4 ± 1.0 | −0.5 ± 1.4 |
| Repeated Compound (VIII) administration group | 12.1 ± 1.1 | −0.5 ± 0.9 | 0.1 ± 0.9 | −1.1 ± 1.1 |

** $P < 0.01$, * $P < 0.05$ [Single morphine administration group vs. Repeated morphine administration group]
$P < 0.01$, # $P < 0.05$ [Repeated morphine administration group vs. Repeated combination administration group]

In the group in which morphine was repeatedly administered for 7 days (repeated morphine administration group: twice a day, one-time administration only on day 7), the response latency was significantly and markedly decreased as compared with that of the single morphine administration group (physiological saline was repeatedly administered twice a day for 6 days, and morphine was administered only on day 7), and the development of analgesic tolerance was observed. In the repeated combination administration group in which Compound (IVA) or (VIII) was orally administered at 30 minutes before administration of morphine (repeated combination administration group: Compound (IVA) or (VIII) was administered at 30 minutes before each administration of morphine in repeated morphine administration group), the degree of the decrease in response latency was smaller as compared with that of the repeated morphine administration group, and the development of analgesic tolerance was prevented. Incidentally, in the group in which Compound (IVA) or (VIII) was repeatedly administered alone (repeated Compound (IVA) administration group, or repeated Compound (VIII) administration group), the effect on the response latency was not observed.

From the above test, it was confirmed that Compounds (IVA) and (VIII) have a suppressing effect on morphine analgesic tolerance. From the results of this test, it was considered that the development of analgesic tolerance following chronic opioid administration can be prevented by using Compound (IV) such as Compound (IVA) or Compound (VIII) and an opioid in combination.

TEST EXAMPLE 7

Suppressing Activity of Compound (IA) on Oxycodone Analgesic Tolerance

Experimental Materials and Methods
1. Used Animals

Male ddY mice (3 to 4 weeks old, Japan SLC, Inc.) having a body weight of 18 to 23 g were used, and the animals were maintained under the following conditions: 19 to 25° C. room temperature, 30 to 70% humidity, and 12-h light and dark cycle (light period: from 7 a.m. to 7 p.m., dark period: from 7 p.m. to 7 a.m.) until they were subjected to the experiment. Food and water were provided ad libitum.

2. Used Agents and Preparation Methods

Hereinafter, the test was performed under the instructions of narcotics researchers in accordance with the narcotic handling rule each time oxycodone was used. Oxycodone was prepared at a concentration of 2 mg/mL using distilled water for injection and orally administered at a dose of 20 mg/kg. Compound (IA) was suspended in 0.5% MC at a concentration of 1 mg/mL and orally administered at a dose of 10 mg/kg.

3. Determination of Analgesic Activity

Nociceptive pain was determined by a hot plate method. Each mouse was placed on a hot plate apparatus (MK-350B, MUROMACHI KIKAI CO., LTD.) set to 53° C., and the time (latency) until an escape response (paw-licking, -biting, -shaking, or jumping) was evoked was determined to be a pain threshold. In the experiment, animals having a response latency of 6 to 16 seconds before the first drug administration were used. Further, in order to minimize the damage to the site of stimulation, the cut-off time was set to 45 seconds. The analgesic activity was evaluated by determining the response latency at 30, 60, and 120 minutes after drug administration on the last day of repeated drug administration (on day 4).

4. Statistical Processing

The experimental results were expressed as mean±standard error. The statistical analysis was performed using a statistical analysis software SAS. Comparison between two groups was performed using a Wilcoxn rank sum test. A p-value of less than 0.05 was considered to be a significant difference.

5. Experimental Results

The results are shown in Table 6.

TABLE 6

Effect of Compound (IA) on Oxycodone Analgesic Tolerance (Response Latency (sec))

| Latency (sec) | Pre value (before drug administration on last day) | ΔChange (Latency at each time point − Pre value) | | |
|---|---|---|---|---|
| | | 0.5 h | 1 h | 2 h |
| Single oxycodone administration group | 11.7 ± 1.0 | 17.5 ± 4.2 | 11.8 ± 2.0 | 6.9 ± 2.4 |
| Repeated oxycodone administration group | 12.4 ± 1.1 | 5.9 ± 3.4 * | 2.7 ± 2.3 ** | 0.1 ± 1.3 ** |
| Repeated combination administration group | 11.9 ± 0.7 | 13.5 ± 2.6 | 6.0 ± 1.6 | 2.2 ± 1.6 |
| Repeated Compound administration group | 11.9 ± 1.2 | −0.2 ± 1.7 | −0.4 ± 2.2 | −0.1 ± 2.2 |

** P < 0.01, * P < 0.05 [Single oxycodone administration group vs. Repeated oxycodone administration group]

In the group in which oxycodone was repeatedly administered for 4 days (repeated oxycodone administration group: twice a day, one-time administration only on day 4), the response latency was significantly and markedly decreased as compared with that of the single oxycodone administration group (distilled water for injection was repeatedly administered twice a day for 3 days, and oxycodone was administered only on day 4), and the development of analgesic tolerance was observed. In the repeated combination administration group in which Compound (IA) was orally administered at 30 minutes before administration of oxycodone, the degree of the decrease in response latency was smaller as compared with that of the repeated oxycodone administration group, and the development of analgesic tolerance was prevented. Incidentally, in the group in which Compound (IA) was repeatedly administered alone (repeated Compound (IA) administration group), the effect on the response latency was not observed.

From the above test, it was confirmed that Compound (IA) has a suppressing effect on oxycodone analgesic tolerance.

It is known that Compound (IA) has potent and selective adenosine $A_{2A}$ receptor antagonistic activity (Eur. J. Pharmacol., 1994, 267(3), 335). Also, it is well known that Compounds (I) to (VIII) each have adenosine $A_{2A}$ receptor antagonistic activity (for example, Nature Reviews 2006, 5, 247, J. Med. Chem., 1993, 36, 1333, U.S. Pat. No. 5,587,378, WO 00/17201, WO 2005/063743, Bioorg. Med. Chem. Lett. 2007, 17, 1376, WO 2002/055524, WO 2003/011864, WO 2006/032273, WO 2002/055083, etc.).

Accordingly, from Test Examples 1 and 3 to 7, it was considered that a compound having adenosine $A_{2A}$ receptor antagonistic activity (for example, Compounds (I) to (VIII)) or a pharmaceutically acceptable salt thereof has a suppressing effect on opioid analgesic tolerance.

Further, from the above Test Example 2, it was considered that a compound having adenosine $A_{2A}$ receptor antagonistic activity (for example, Compounds (I) to (VIII)) or a pharmaceutically acceptable salt thereof improves constipation induced by an opioid such as morphine, and that constipation caused by administration of an opioid can be improved by using a compound having adenosine $A_{2A}$ receptor antagonistic activity (for example, Compounds (I) to (VIII)) or a pharmaceutically acceptable salt thereof and an opioid in combination.

That is, from the above Test Examples 1 to 7, it is considered that the undesirable effect (for example, analgesic tolerance, constipation, etc.) of an opioid can be suppressed by using a compound having adenosine $A_{2A}$ receptor antagonistic activity (for example, Compounds (I) to (VIII)) or a pharmaceutically acceptable salt thereof and an opioid in combination. Further, it is expected that an increase in the dose of an opioid can be prevented by using a compound having adenosine $A_{2A}$ receptor antagonistic activity (for example, Compounds (I) to (VIII)) or a pharmaceutically acceptable salt thereof and an opioid in combination, and as a result, it is considered that the undesirable effect (for example, drowsiness, wobble, respiratory depression, hallucination, anxiety, pruritus, etc.) of an opioid due to an increase in the dose of the opioid can be suppressed. That is, it is considered that use of a compound having adenosine $A_{2A}$ receptor antagonistic activity or a pharmaceutically acceptable salt thereof and an opioid in combination is useful for the treatment and/or prevention of pain in which an undesirable effect of an opioid is reduced. Accordingly, the therapeutic and/or preventive agent for pain and the method for treating and/or preventing pain of the present invention are effective particularly in patients in which the useful effect of an opioid itself cannot be sufficiently achieved due to the undesirable effect (for example, analgesic tolerance, constipation, etc.) of an opioid such as morphine.

Hereinafter, the aspects of the present invention will be more specifically described with Examples, however, the scope of the present invention is not limited to these Examples.

EXAMPLE 1

Tablets having the following composition are prepared according to the conventional manner. Compound (IA) (40 g), lactose (286.8 g), and potato starch (60 g) are mixed, and then a 10% aqueous solution of hydroxypropyl cellulose (120 g) is added thereto. The resulting mixture is kneaded, granulated, dried, and sized according to the conventional manner, whereby granules for tableting are prepared. Magnesium stearate (1.2 g) is added thereto and mixed therewith, and the resulting mixture is tableted using a tableting machine (RT-15, manufactured by Kikusui Seisakusho Ltd.) with a punch having a diameter of 8 mm, whereby tablets (containing 20 mg of the active ingredient per tablet) are obtained.

TABLE 7

| Formulation | |
|---|---|
| Compound (IA) | 20 mg |
| Lactose | 143.4 mg |
| Potato starch | 30 mg |
| Hydroxypropyl cellulose | 6 mg |
| Magnesium stearate | 0.6 mg |
| | 200 mg |

EXAMPLE 2

Tablets having the following composition are prepared in the same manner as in Example 1.

TABLE 8

| Formulation | |
|---|---|
| Compound (IB) | 20 mg |
| Lactose | 143.4 mg |
| Potato starch | 30 mg |
| Hydroxypropyl cellulose | 6 mg |
| Magnesium stearate | 0.6 mg |
| | 200 mg |

EXAMPLE 3

Tablets having the following composition are prepared in the same manner as in Example 1.

TABLE 9

| Formulation | |
|---|---|
| Compound (IIA) | 20 mg |
| Lactose | 143.4 mg |
| Potato starch | 30 mg |
| Hydroxypropyl cellulose | 6 mg |
| Magnesium stearate | 0.6 mg |
| | 200 mg |

EXAMPLE 4

Tablets having the following composition are prepared in the same manner as in Example 1.

TABLE 10

| Formulation | |
|---|---|
| Compound (IIIA) | 20 mg |
| Lactose | 143.4 mg |
| Potato starch | 30 mg |
| Hydroxypropyl cellulose | 6 mg |
| Magnesium stearate | 0.6 mg |
| | 200 mg |

EXAMPLE 5

Tablets having the following composition are prepared in the same manner as in Example 1.

TABLE 11

| Formulation | |
|---|---|
| Compound (IIIB) | 20 mg |
| Lactose | 143.4 mg |
| Potato starch | 30 mg |
| Hydroxypropyl cellulose | 6 mg |
| Magnesium stearate | 0.6 mg |
| | 200 mg |

EXAMPLE 6

Tablets having the following composition are prepared in the same manner as in Example 1.

TABLE 12

| Formulation | |
|---|---|
| Compound (IIIC) | 20 mg |
| Lactose | 143.4 mg |
| Potato starch | 30 mg |
| Hydroxypropyl cellulose | 6 mg |
| Magnesium stearate | 0.6 mg |
| | 200 mg |

EXAMPLE 7

Tablets having the following composition are prepared in the same manner as in Example 1.

TABLE 13

| Formulation | |
|---|---|
| Compound (IVA) | 20 mg |
| Lactose | 143.4 mg |
| Potato starch | 30 mg |
| Hydroxypropyl cellulose | 6 mg |
| Magnesium stearate | 0.6 mg |
| | 200 mg |

EXAMPLE 8

Tablets having the following composition are prepared in the same manner as in Example 1.

TABLE 14

| Formulation | |
|---|---|
| Compound (V) | 20 mg |
| Lactose | 143.4 mg |
| Potato starch | 30 mg |
| Hydroxypropyl cellulose | 6 mg |
| Magnesium stearate | 0.6 mg |
| | 200 mg |

EXAMPLE 9

Tablets having the following composition are prepared in the same manner as in Example 1.

TABLE 15

| Formulation | |
|---|---|
| Compound (VIA) | 20 mg |
| Lactose | 143.4 mg |
| Potato starch | 30 mg |
| Hydroxypropyl cellulose | 6 mg |
| Magnesium stearate | 0.6 mg |
| | 200 mg |

EXAMPLE 10

Tablets having the following composition are prepared in the same manner as in Example 1.

TABLE 16

| Formulation | |
|---|---|
| Compound (VII) | 20 mg |
| Lactose | 143.4 mg |
| Potato starch | 30 mg |
| Hydroxypropyl cellulose | 6 mg |
| Magnesium stearate | 0.6 mg |
| | 200 mg |

EXAMPLE 11

Tablets having the following composition are prepared in the same manner as in Example 1.

TABLE 17

| Formulation | |
|---|---|
| Morphine | 20 mg |
| Lactose | 143.4 mg |
| Potato starch | 30 mg |
| Hydroxypropyl cellulose | 6 mg |
| Magnesium stearate | 0.6 mg |
| | 200 mg |

EXAMPLE 12

Tablets having the following composition are prepared according to the conventional manner. Compound (IA) (40 g), morphine (40 g), lactose (246.8 g), and potato starch (60 g) are mixed, and then a 10% aqueous solution of hydroxypropyl cellulose (120 g) is added thereto. The resulting mixture is kneaded, granulated, dried, and sized according to the conventional manner, whereby granules for tableting are prepared. Magnesium stearate (1.2 g) is added thereto and mixed therewith, and the resulting mixture is tableted using a tableting machine (RT-15, manufactured by Kikusui Seisakusho Ltd.) with a punch having a diameter of 8 mm, whereby tablets (containing 20 mg of Compound (IA) and 20 mg of morphine per tablet) are obtained.

TABLE 18

| Formulation | |
|---|---|
| Compound (IA) | 20 mg |
| Morphine | 20 mg |
| Lactose | 123.4 mg |

TABLE 18-continued

| Formulation | |
|---|---|
| Potato starch | 30 mg |
| Hydroxypropyl cellulose | 6 mg |
| Magnesium stearate | 0.6 mg |
| | 200 mg |

EXAMPLE 13

Tablets having the following composition are prepared in the same manner as in Example 12.

TABLE 19

| Formulation | |
|---|---|
| Compound (IB) | 20 mg |
| Morphine | 20 mg |
| Lactose | 123.4 mg |
| Potato starch | 30 mg |
| Hydroxypropyl cellulose | 6 mg |
| Magnesium stearate | 0.6 mg |
| | 200 mg |

EXAMPLE 14

Tablets having the following composition are prepared in the same manner as in Example 12.

TABLE 20

| Formulation | |
|---|---|
| Compound (IIA) | 20 mg |
| Morphine | 20 mg |
| Lactose | 123.4 mg |
| Potato starch | 30 mg |
| Hydroxypropyl cellulose | 6 mg |
| Magnesium stearate | 0.6 mg |
| | 200 mg |

EXAMPLE 15

Tablets having the following composition are prepared in the same manner as in Example 12.

TABLE 21

| Formulation | |
|---|---|
| Compound (IIIA) | 20 mg |
| Morphine | 20 mg |
| Lactose | 123.4 mg |
| Potato starch | 30 mg |
| Hydroxypropyl cellulose | 6 mg |
| Magnesium stearate | 0.6 mg |
| | 200 mg |

EXAMPLE 16

An injection having the following composition is prepared according to the conventional manner. Compound (IB) (1 g) is added to distilled water for injection and mixed therewith. Hydrochloric acid and an aqueous solution of sodium hydroxide are further added thereto to adjust the pH of the mixture to 7, and distilled water for injection is added thereto to make the total amount 1000 mL. The obtained mixed liquid is aseptically filled in glass vials in an amount of 2 mL per vial, whereby injections (containing 2 mg of the active ingredient per vial) are obtained.

TABLE 22

| Formulation | |
| --- | --- |
| Compound (IB) | 2 mg |
| Hydrochloric acid | appropriate amount |
| Aqueous solution of sodium hydroxide | appropriate amount |
| Distilled water for injection | appropriate amount |
| | 2.00 mL |

EXAMPLE 17

An injection having the following composition is prepared in the same manner as in Example 16.

TABLE 23

| Formulation | |
| --- | --- |
| Compound (IVA) | 2 mg |
| Hydrochloric acid | appropriate amount |
| Aqueous solution of sodium hydroxide | appropriate amount |
| Distilled water for injection | appropriate amount |
| | 2.00 mL |

EXAMPLE 18

An Injection having the following composition is prepared in the same manner as in Example 16.

TABLE 24

| Formulation | |
| --- | --- |
| Morphine | 2 mg |
| Hydrochloric acid | appropriate amount |
| Aqueous solution of sodium hydroxide | appropriate amount |
| Distilled water for injection | appropriate amount |
| | 2.00 mL |

EXAMPLE 19

An injection having the following composition is prepared according to the conventional manner. Compound (IB) (1 g) and morphine (1 g) are added to distilled water for injection and mixed therewith. Hydrochloric acid and an aqueous solution of sodium hydroxide are further added thereto to adjust the pH of the mixture to 7, and distilled water for injection is added thereto to make the total amount 1000 mL. The obtained mixed liquid is aseptically filled in glass vials in an amount of 2 mL per vial, whereby injections (containing 2 mg of Compound (IB) and 2 mg of morphine per vial) are obtained.

TABLE 25

| Formulation | |
| --- | --- |
| Compound (IB) | 2 mg |
| Morphine | 2 mg |
| Hydrochloric acid | appropriate amount |
| Aqueous solution of sodium hydroxide | appropriate amount |
| Distilled water for injection | appropriate amount |
| | 2.00 mL |

EXAMPLE 20

An injection having the following composition is prepared in the same manner as in Example 19.

TABLE 26

| Formulation | |
| --- | --- |
| Compound (IB) | 2 mg |
| Heroin | 2 mg |
| Hydrochloric acid | appropriate amount |
| Aqueous solution of sodium hydroxide | appropriate amount |
| Distilled water for injection | appropriate amount |
| | 2.00 mL |

EXAMPLE 21

An injection having the following composition is prepared in the same manner as in Example 19.

TABLE 27

| Formulation | |
| --- | --- |
| Compound (IVA) | 2 mg |
| Heroin | 2 mg |
| Hydrochloric acid | appropriate amount |
| Aqueous solution of sodium hydroxide | appropriate amount |
| Distilled water for injection | appropriate amount |
| | 2.00 mL |

EXAMPLE 22

An injection having the following composition is prepared in the same manner as in Example 19.

TABLE 28

| Formulation | |
| --- | --- |
| Compound (V) | 2 mg |
| Heroin | 2 mg |
| Hydrochloric acid | appropriate amount |
| Aqueous solution of sodium hydroxide | appropriate amount |
| Distilled water for injection | appropriate amount |
| | 2.00 mL |

Industrial Applicability

According to the present invention, an agent for suppressing an undesirable effect of an opioid-type analgesic (opioid), which comprises a compound having adenosine $A_{2A}$ receptor antagonistic activity or a pharmaceutically acceptable salt thereof as an active ingredient, and the like can be provided.

Description of Reference Numerals and Signs
1. FIG. 1
-♦-: Single morphine administration group
-▲-: Repeated morphine administration group
-●-: Repeated combination administration group
-■-: Repeated Compound (IA) administration group
\*\*: P<0.01 [Single morphine administration group vs. Repeated morphine administration group (Wilcoxn rank sum test)]
: P<0.01 [Repeated morphine administration group vs. Repeated combination administration group (Wilcoxn rank sum test)]
: P<0.05 [Repeated morphine administration group vs. Repeated combination administration group (Wilcoxn rank sum test)]
2. FIG. 2
\*\*: P<0.01 (Wilcoxn rank sum test)

The invention claimed is:

1. A method for suppressing an undesirable effect of an opioid, which comprises administering an effective amount of a compound represented by at least one of formulae (I) to (VIII), or a pharmaceutically acceptable salt thereof:

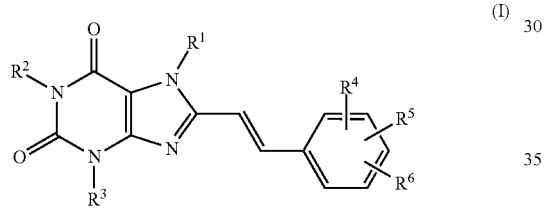
(I)

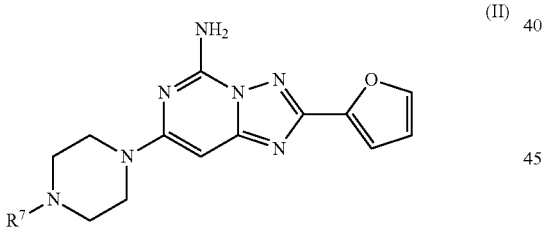
(II)

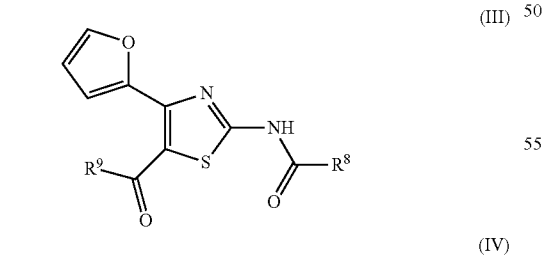
(III)

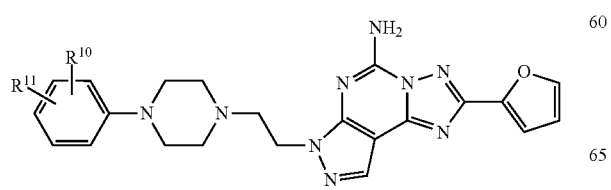
(IV)

-continued

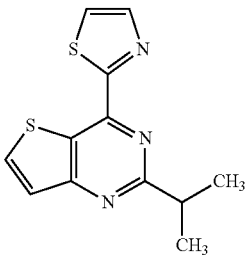
(V)

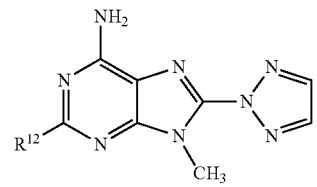
(VI)

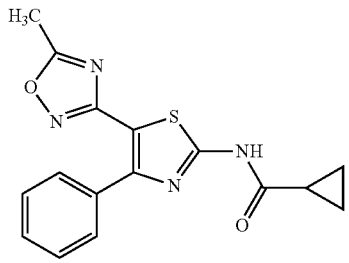
(VII)

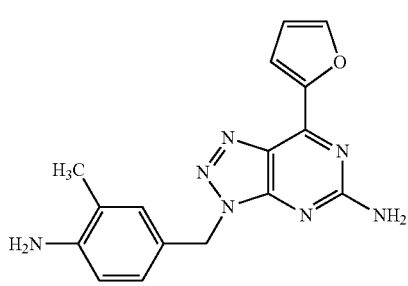
(VIII)

in which $R^1$ represents a hydrogen atom or methyl; $R^2$ and $R^3$ independently represent methyl, ethyl, propyl, butyl or isopropyl; $R^4$, $R^5$ and $R^6$ independently represent a hydrogen atom, methyl, ethyl, methoxy, ethoxy, a fluorine atom, a chlorine atom or a bromine atom; $R^7$ represents methyl, ethyl, propyl, butyl or 3-methylbutyl, each of which is optionally substituted with hydroxy; $R^8$ represents phenyl, pyridyl, pyrimidinyl or 5,6-dihydro-2H-pyridylmethyl, each of which is optionally substituted with 1 to 3 substituents selected from the group consisting of a chlorine atom, methyl, ethyl, methoxy and ethoxy; $R^9$ represents pyridyl or tetrahydropyranyl; $R^{10}$ and $R^{11}$ independently represent a hydrogen atom, a fluorine atom or 2-methoxyethoxy; and $R^{12}$ represents methyl, ethyl, propyl or butyl, wherein
said undesirable effect is analgesic tolerance.

2. The method according to claim 1, wherein the opioid is selected from the group consisting of anileridine, opium, ampromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimeheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

3. The method according to claim 1, wherein the opioid is morphine.

4. The method according to claim 1, wherein the compound is represented by at least one of formula (IA), (IB), (IC), (ID), (IIA), (IIIA), (IIIB), (IIIC), (IVA), (V), (VIA), (VII) or (VIII), or a pharmaceutically acceptable salt thereof:

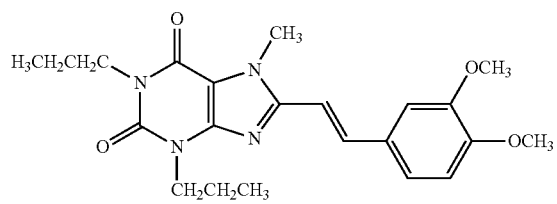
(IA)

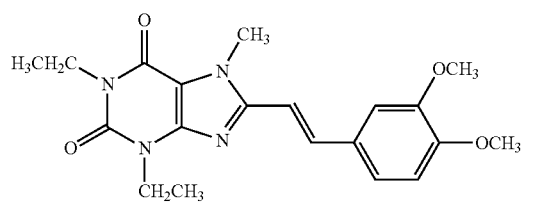
(IB)

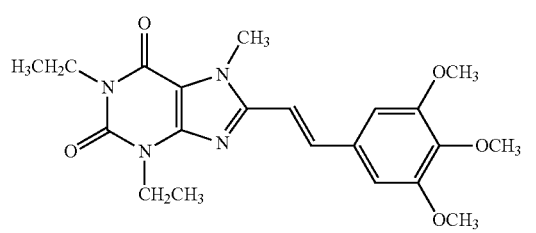
(IC)

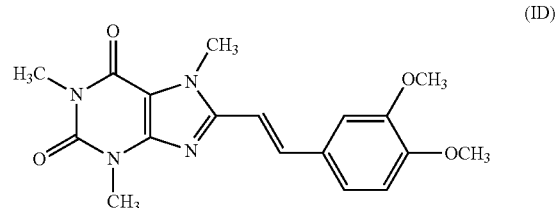
(ID)

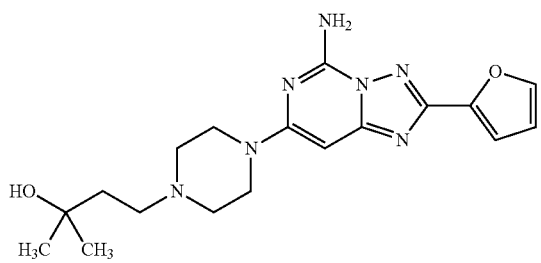
(IIA)

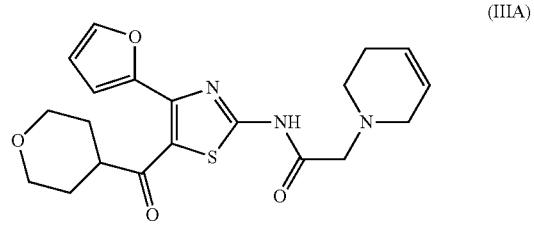
(IIIA)

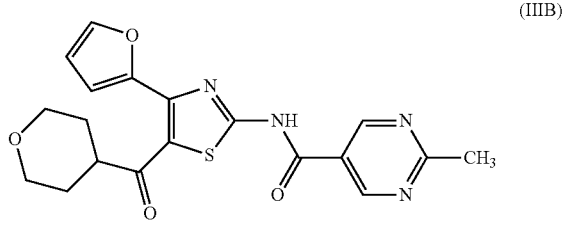
(IIIB)

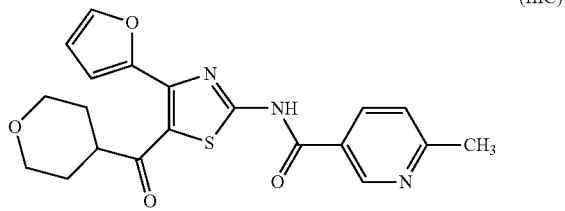
(IIIC)

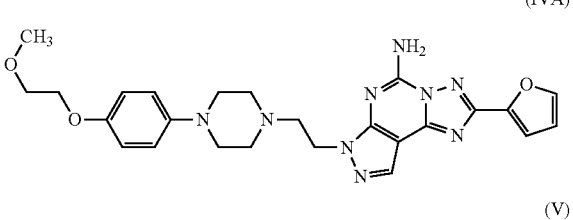
(IVA)

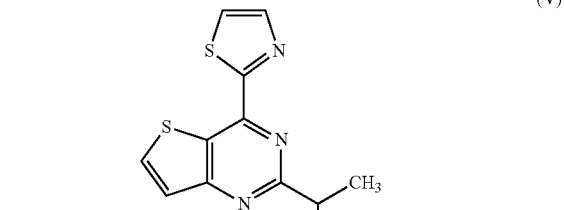
(V)

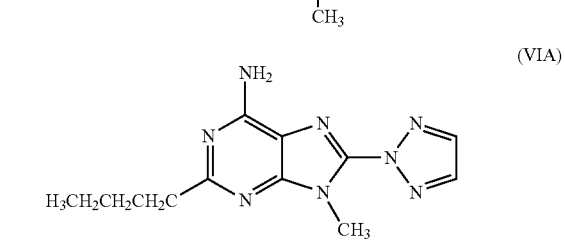
(VIA)

-continued

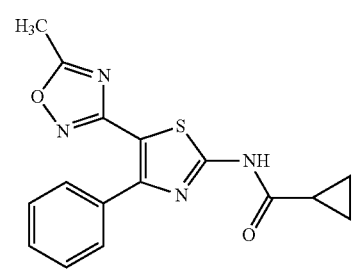
(VII)

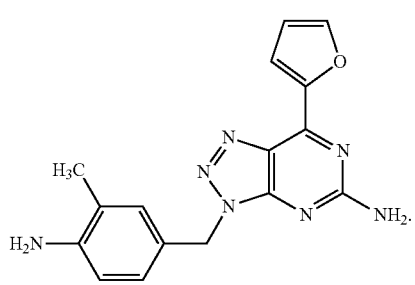
(VIII)

5. The method according to claim 1, wherein the compound is represented by at least one of formula (IA) or (IB), or a pharmaceutically acceptable salt thereof:

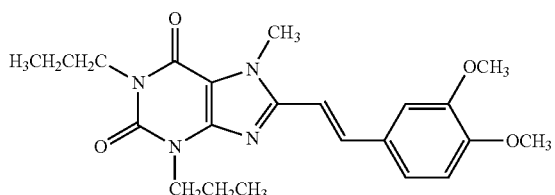
(IA)

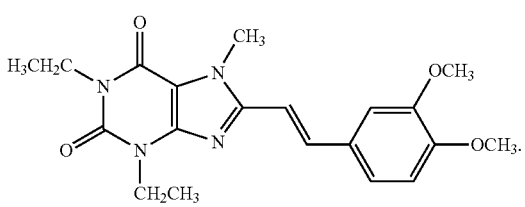
(IB)

6. The method according to claim 1, wherein the compound is represented by formula (IIIC), or a pharmaceutically acceptable salt thereof:

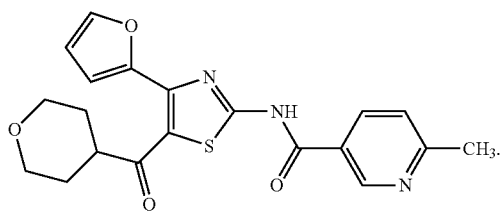
(IIIC)

7. The method according to claim 4, wherein the opioid is selected from the group consisting of anileridine, opium, ampromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

8. The method according to claim 4, wherein the opioid is morphine.

9. The method according to claim 5, wherein the opioid is selected from the group consisting of anileridine, opium, ampromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

10. The method according to claim 5, wherein the opioid is morphine.

11. The method according to claim 6, wherein the opioid is selected from the group consisting of anileridine, opium, ampromide, allylprodine, alphaprodine, alfentanil, isomethadone, ethylmethylthiambutene, ethylmorphine, ethoheptazine, etonitazene, eptazocine, endorphin, enkephalin, oxycodone, oxymorphone, clonitazene, ketobemidone, cocaine, codeine, cylmorphan, diamorphone, dioxaphetylbutyrate, didezocine, dinorphine, dihydrocodeine, dihydromorphine, dipipanone, dimethylthiambutene, dimenoxadol, dimepheptanol, sufentanil, tilidine, dextromoramide, desomorphine, tramadol, narceine, nalorphine, nalbuphene, nicomorphine, norlevorphanol, normethadone, normorphine, norpipanone, papaveretum, hydrocodone, hydroxypethidine, hydromorphone, piminodine, piritramide, fentanyl, phenazocine, phenadoxone, phenoperidine, phenomorphan, butorphanol, buprenorphine, properidine, propoxyphene, propheptazine, promedol, heroin, bezitramide, berzylmorphine, pentazocine, myrophine, methadone, metazocine, metopon, meptazinol, meperidine, morphine, levallorphan, levophenalofentanil, levorphanol, and remifentanil.

12. The method according to claim 6, wherein the opioid is morphine.

* * * * *

UNITED STATES PATENT AND TRADEMARK OFFICE
CERTIFICATE OF CORRECTION

| | | |
|---|---|---|
| PATENT NO. | : 8,865,731 B2 | Page 1 of 16 |
| APPLICATION NO. | : 12/994923 | |
| DATED | : October 21, 2014 | |
| INVENTOR(S) | : Ouchi et al. | |

It is certified that error appears in the above-identified patent and that said Letters Patent is hereby corrected as shown below:

ON THE TITLE PAGE ITEM [56]

Other Publications:
    Under Ferré et al., "addition" should read --addiction--;
    Under Snyder, "theraphy"," should read --therapy",--;
    "Yao, et al., "Adenosine A2a blockade prevents synergy between μ-opiate and cannabinoid
        CB1 receptors and eliminates heroin-seeking behavior in addicted rats", PNAS, vol.
        103, No. 20 (2006) 7877-82." (dupl. of cover) should be deleted; and
    Under Yao et al. "mu-" should read --μ- --.

IN THE DRAWINGS

SHEET 1:

Figure 2, "morphne" should read --morphine--.

IN THE SPECIFICATION

COLUMN 1:

Line 17, "effect" should read --effects--;
    Line 41, "improve" should read --improves--;
    Line 59, "heroine" should read --heroin--; and
    Line 63, "affects" should read --effects--.

COLUMN 5:

Line 4, "Vol. 267, p." should read --Vol. 267, p. 335--; and
    Line 9, "Vol. 36, p." should read --Vol. 36, p. 1333--.

Signed and Sealed this
Twelfth Day of January, 2016

Michelle K. Lee
*Director of the United States Patent and Trademark Office*

CERTIFICATE OF CORRECTION (continued)
U.S. Pat. No. 8,865,731 B2

COLUMN 6:

Line 58-66,

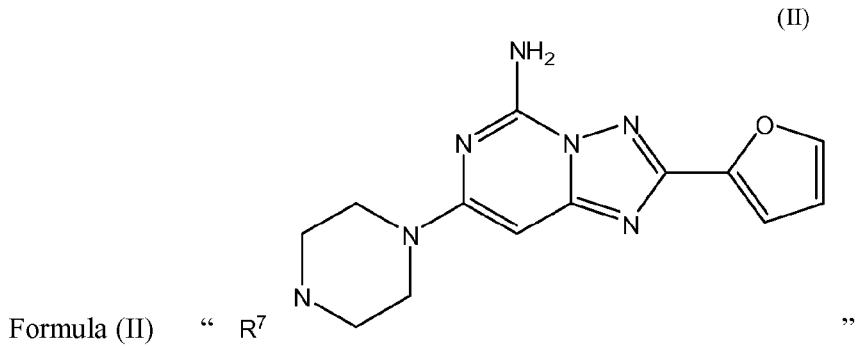

Formula (II) " R⁷ "

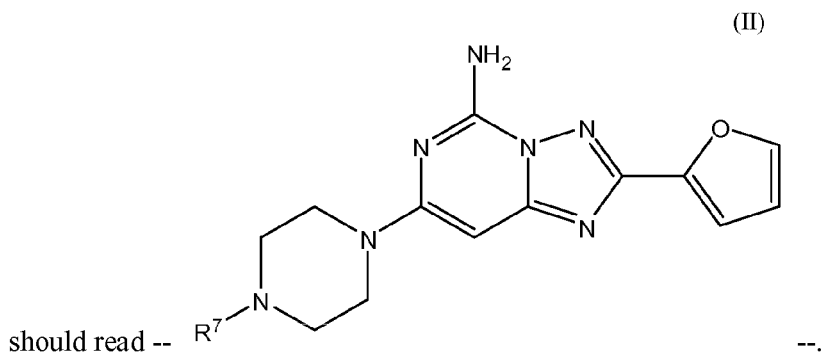

should read -- R⁷ --.

COLUMN 7:

Line 34-42,

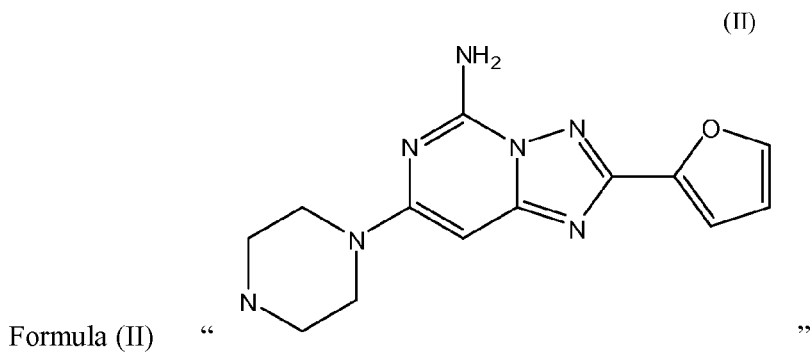

Formula (II) " "

should read -- 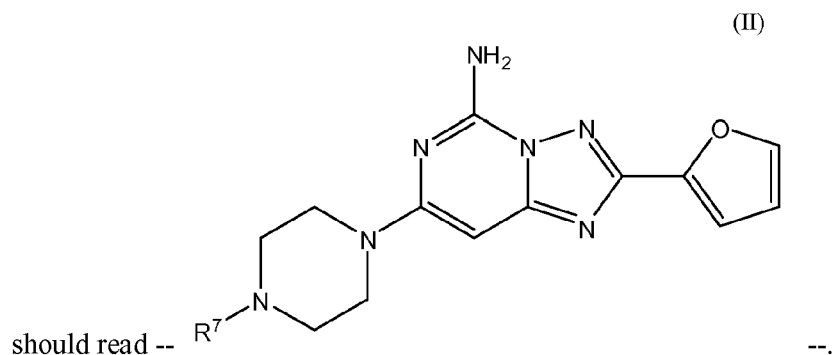 --.
COLUMN 8:
Line 1, "mula" should read --mulae-- and "(MC)," should read --(IIIC),--.
COLUMN 10:
Line 51, "mula" should read --mulae--.
COLUMN 12:
Line 1, "dorsolumbar pain," (dupl.) should be deleted; and
Line 25-30,
Formula (II)  " 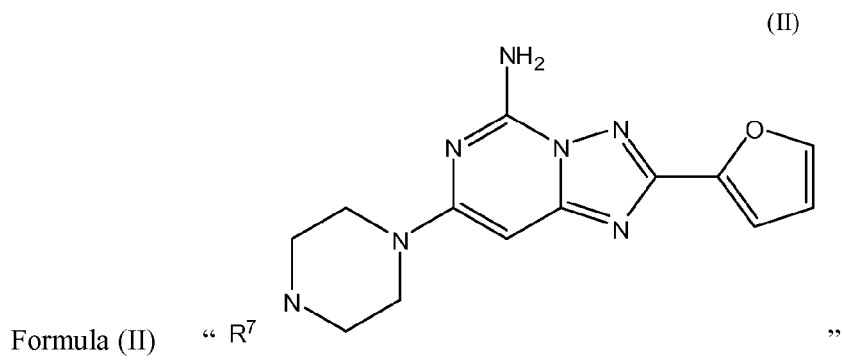 "
should read -- 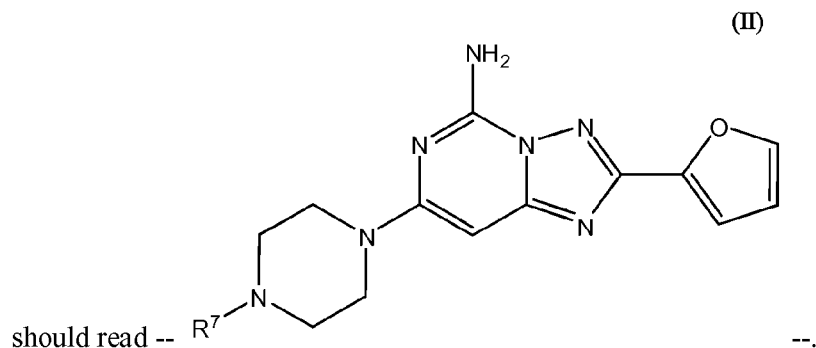 --.

COLUMN 13:
Line 55-65,
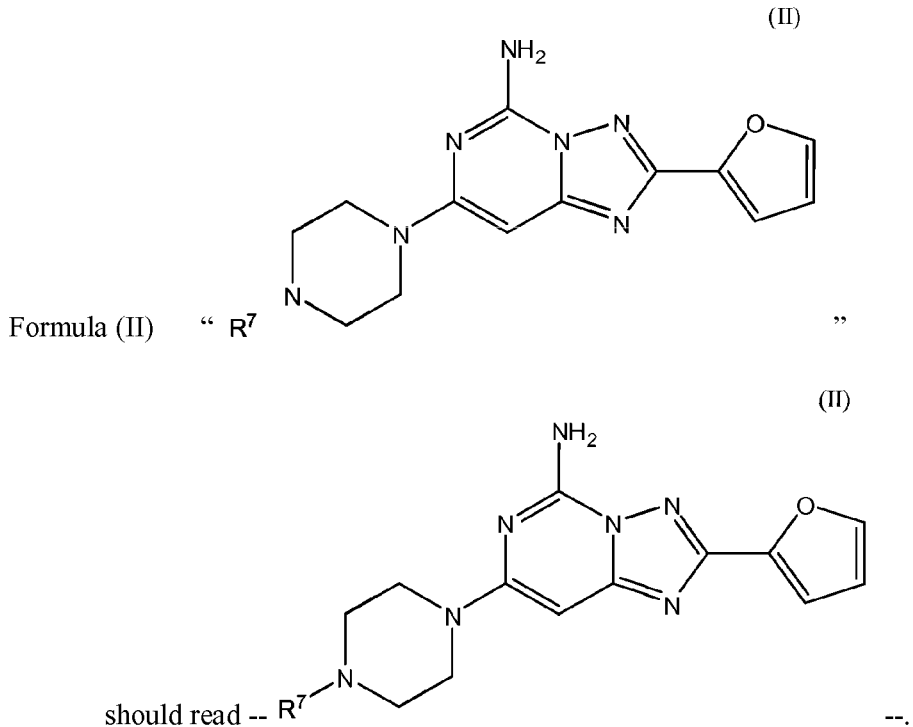
Formula (II) " R⁷ "
should read -- R⁷ --.
COLUMN 14:
Line 25, "mula" should read --mulae--.
COLUMN 16:
Line 27, "mula" should read --mulae--; and
Line 51, "mula" should read --mulae--.

CERTIFICATE OF CORRECTION (continued)
U.S. Pat. No. 8,865,731 B2

COLUMN 19:

Line 12-21,

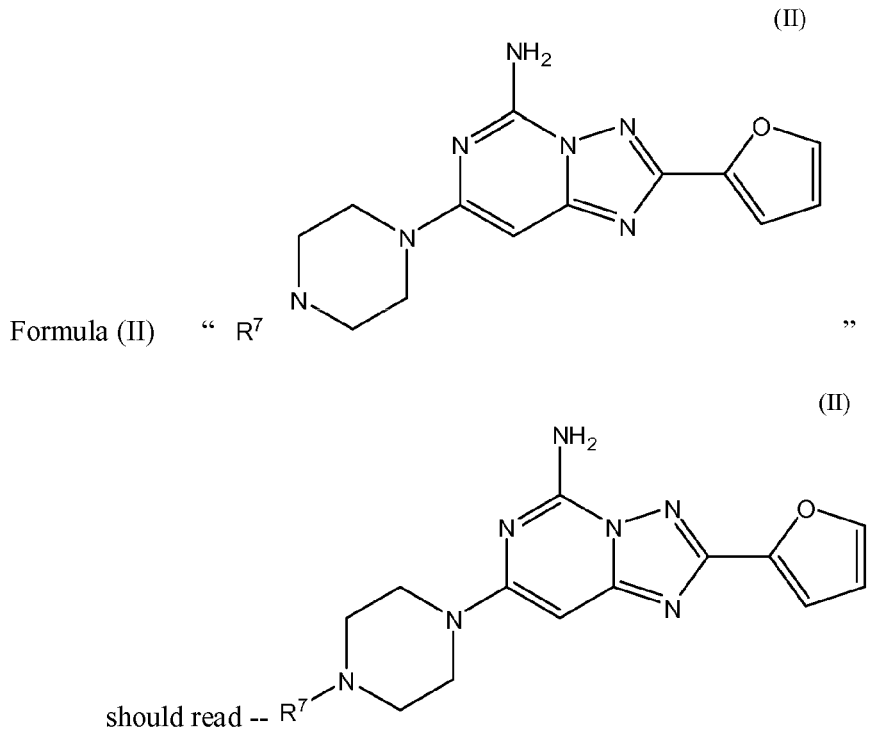

Formula (II)   " R⁷                                              "

should read -- R⁷                                              --.

COLUMN 20:

Line 19, "formula" should read --formulae--.

COLUMN 22:

Line 50, "formula" should read --formulae--.

COLUMN 24:

Line 12-20,

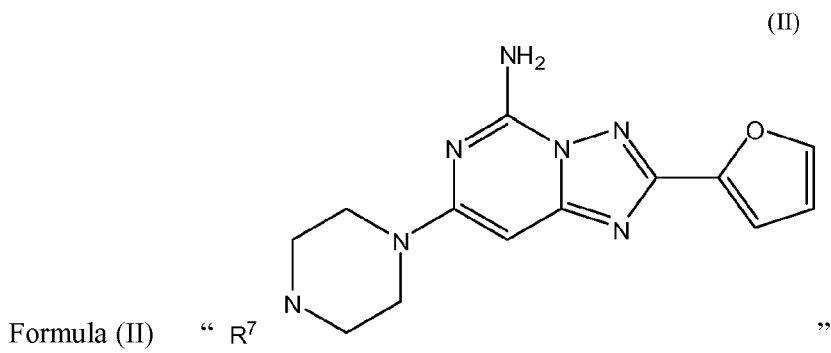

Formula (II)   " R⁷                                              "

should read -- 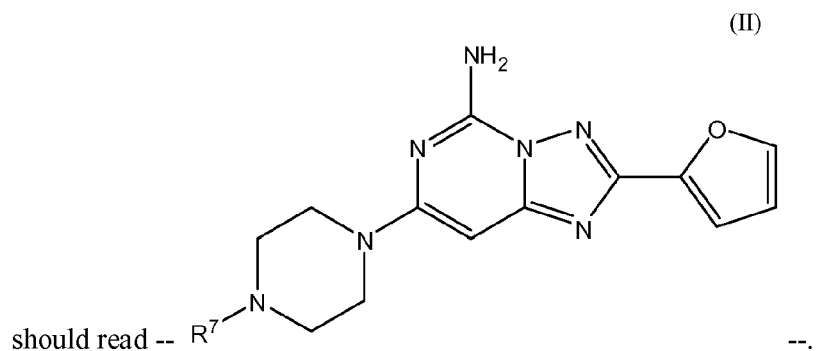 --.
COLUMN 25:
Line 53-61,
Formula (II) " 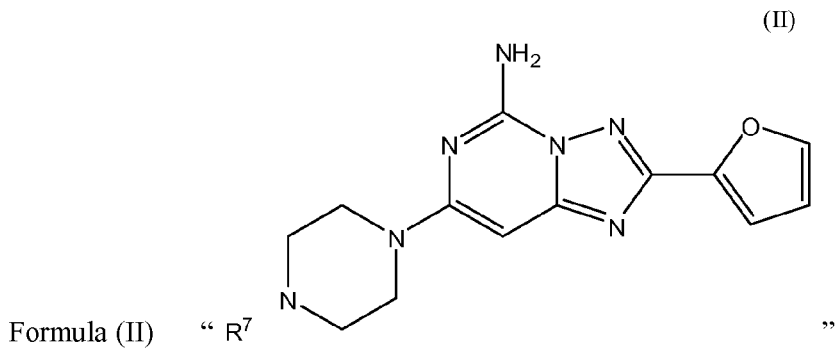 "
should read -- 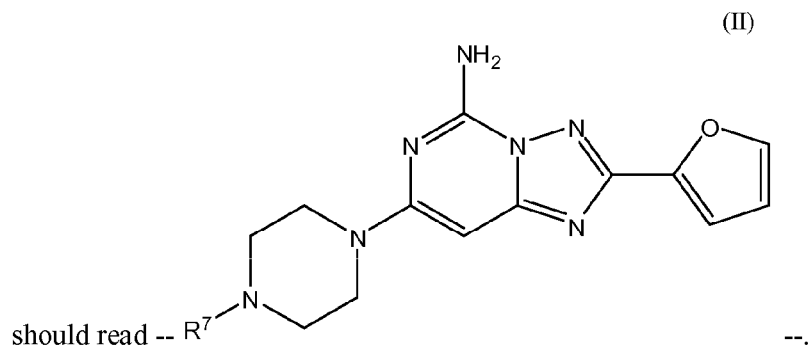 --.
COLUMN 26:
Line 19, "(MB)," should read --(IIIB),--.
COLUMN 28:
Line 32, "formula" should read --formulae--; and
Line 65, "formula" should read --formulae--.

COLUMN 30:
Line 31-38,
Formula (II) " R⁷ 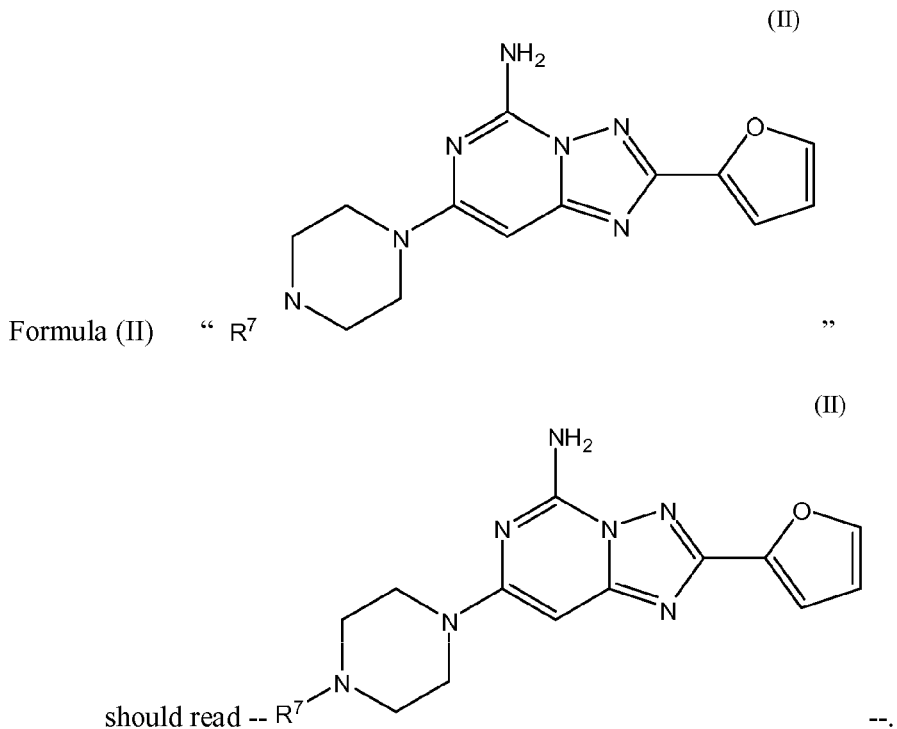 "
should read -- R⁷ --.
COLUMN 31:
Line 40, "mula" should read --mulae--; and
Line 58-67,
Formula (II) " R⁷ 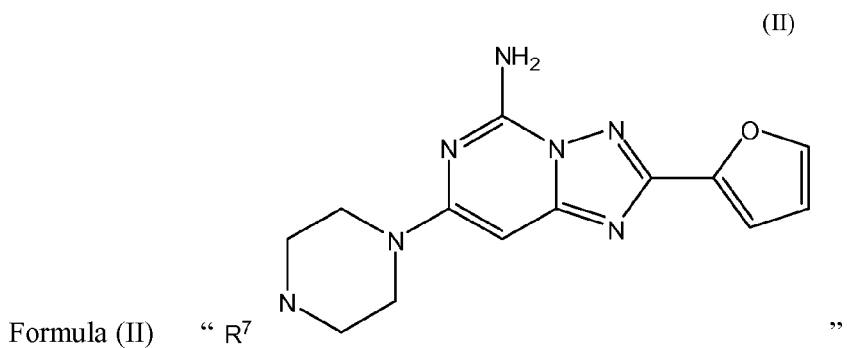 "

should read -- 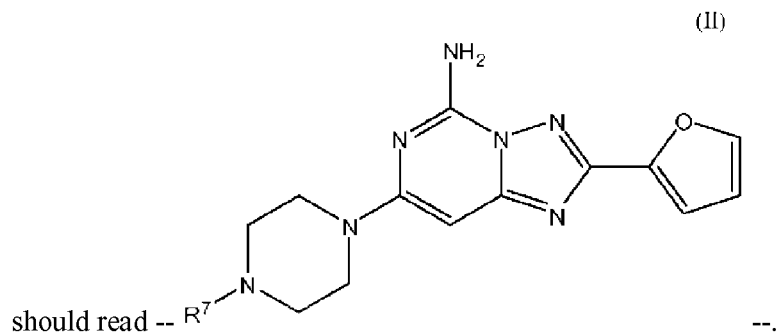 --.
COLUMN 32:
Line 18, "mula" should read --mulae--.
COLUMN 35:
Line 3-9,
Formula (II)   " 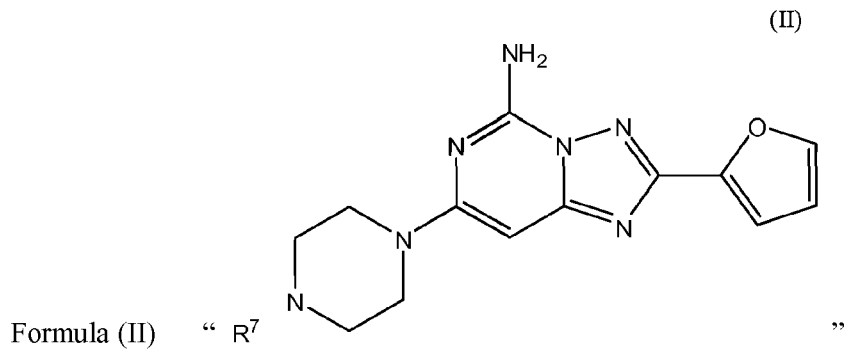 "
should read -- 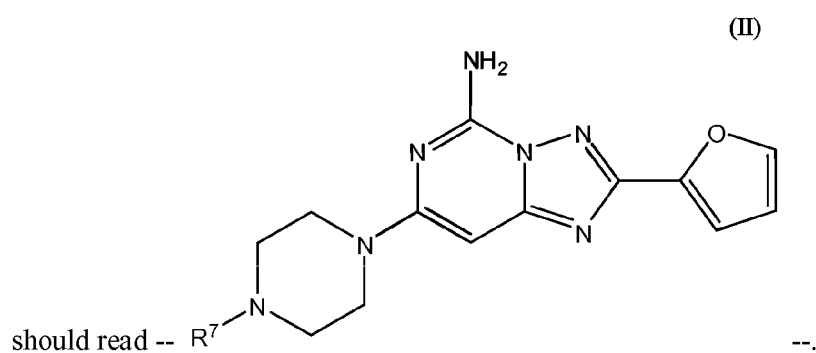 --.
COLUMN 36:
Line 6, "formula" should read --formulae--;

CERTIFICATE OF CORRECTION (continued)
U.S. Pat. No. 8,865,731 B2

Line 20-27,

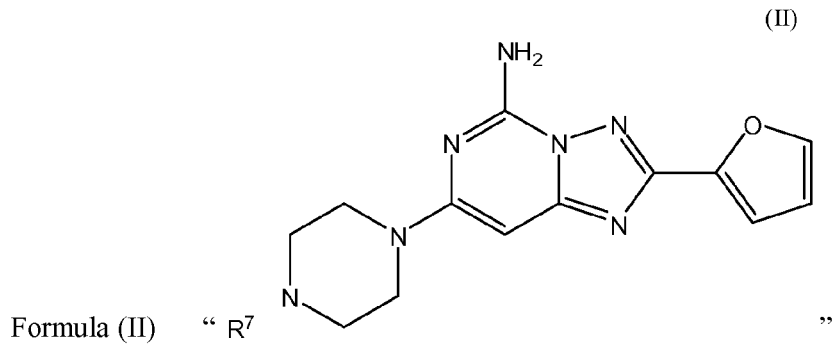

Formula (II)   " R⁷                                                                    "

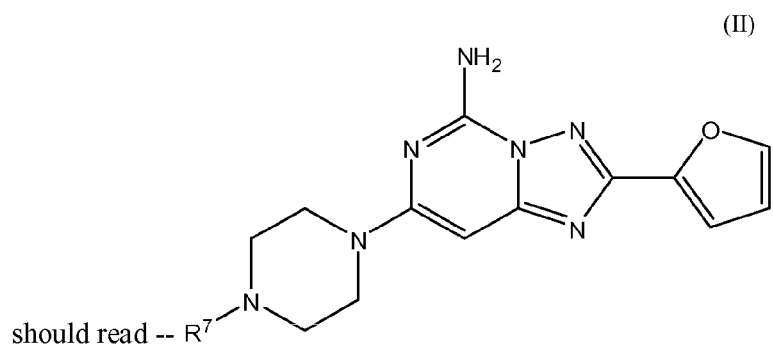

should read -- R⁷                                                                    --; and Line 43, "(IIA)," should read --(IIA), (IIIA),--.

COLUMN 39:

Line 26-33,

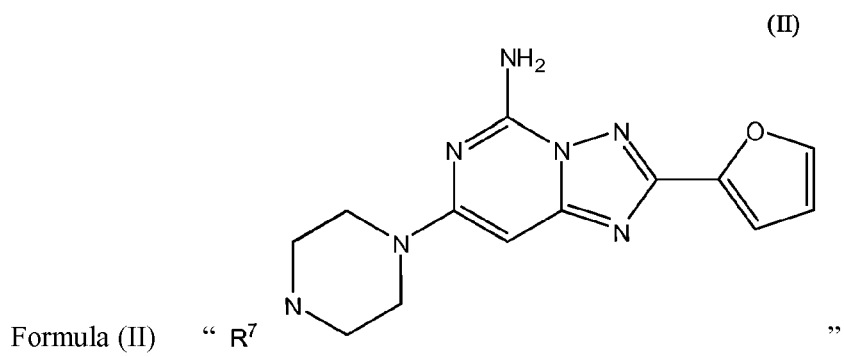

Formula (II)   " R⁷                                                                    "

CERTIFICATE OF CORRECTION (continued)
U.S. Pat. No. 8,865,731 B2 should read -- 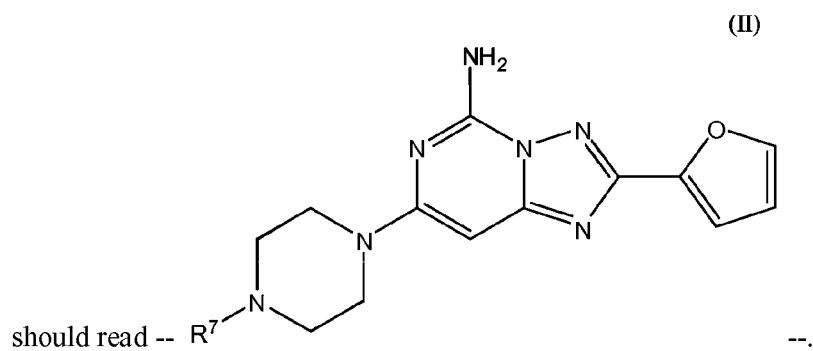 --.

COLUMN 40:

Line 31, "mula" should read --mulae--; and
Line 44-52,

Formula (II) " 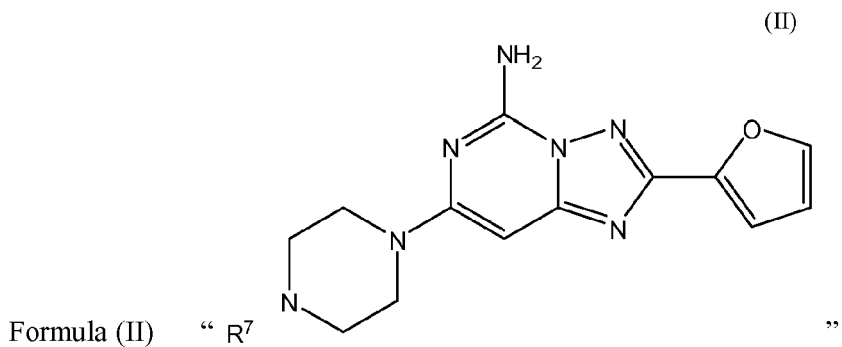 "

should read -- 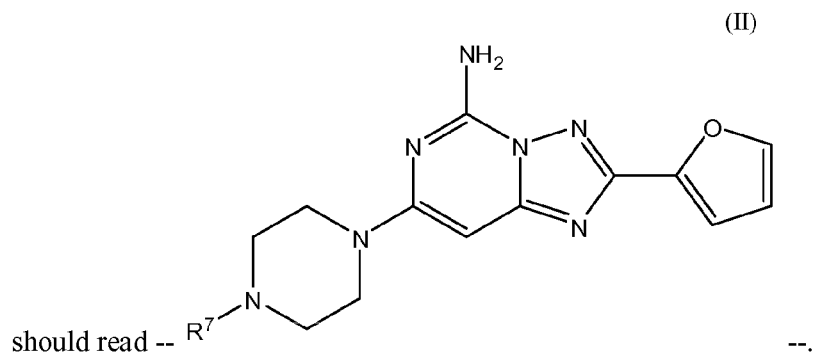 --.

COLUMN 41:

Line 1, "mula" should read --mulae--.

COLUMN 44:
Line 1-10,
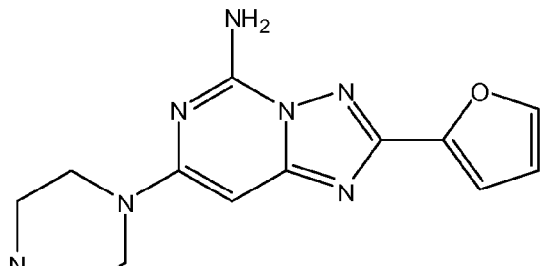
Formula (II)   " R⁷                       "
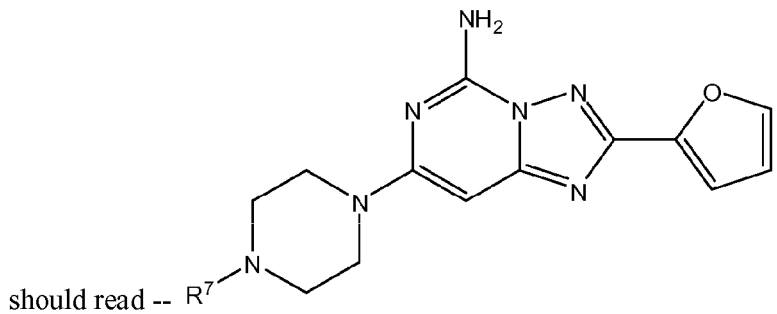
should read -- R⁷                       --.
COLUMN 45:
Line 6, "formula" should read --formulae--; and
Line 21-27,
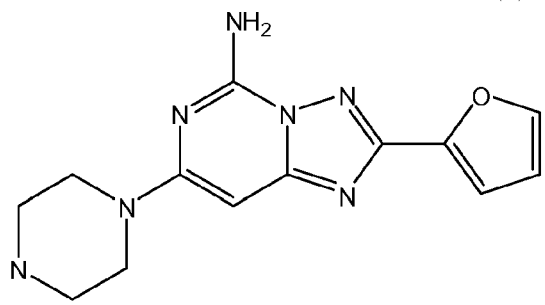
Formula (II)   " R⁷                       "

should read -- 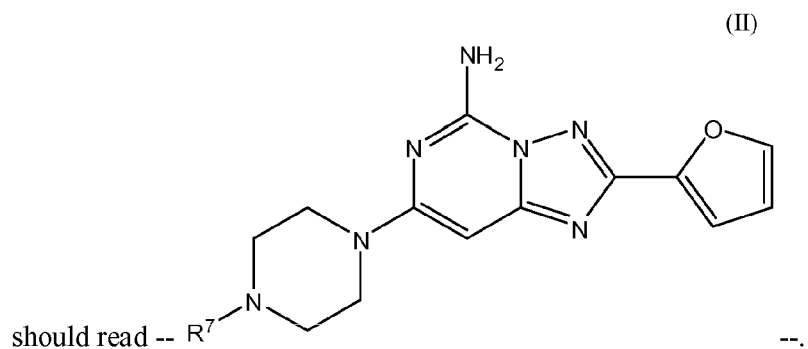 --.
COLUMN 48:
Line 32-38,
Formula (II) " 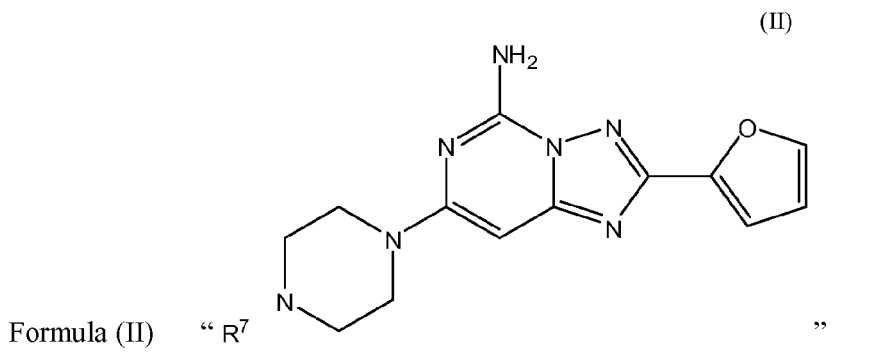 "
should read -- 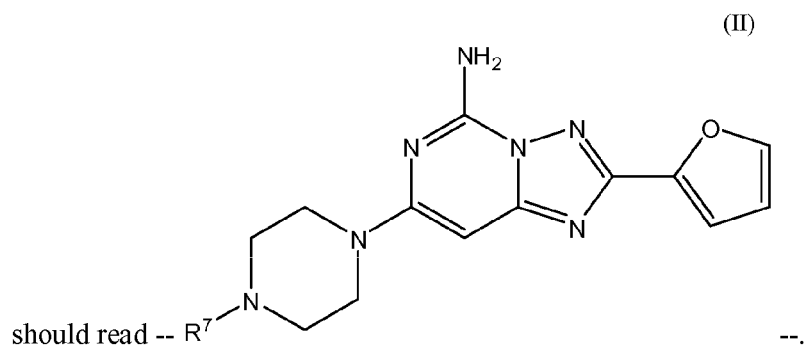 --.
COLUMN 49:
Line 41, "mula" should read --mulae--; and Line 58-67,
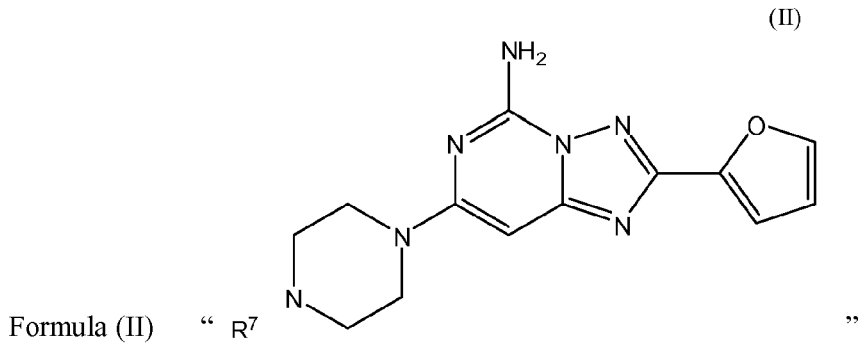
Formula (II)  " R⁷                  "
should read -- 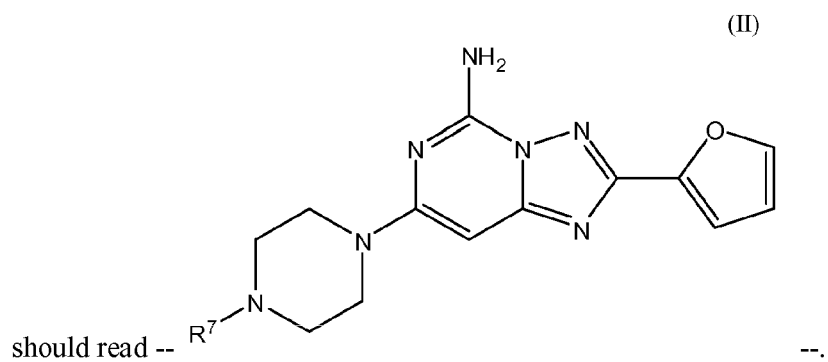 --.
COLUMN 52:
Line 41, "hydromorphone," should read --hydromorphone, piminodine,--; and
Line 56, "(ID)" should read --(b)--.
COLUMN 53:
Line 12-20,
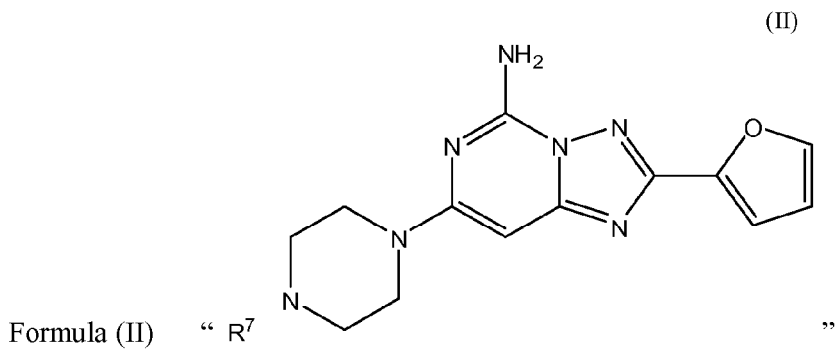
Formula (II)  " R⁷                  "

CERTIFICATE OF CORRECTION (continued)
U.S. Pat. No. 8,865,731 B2 should read -- 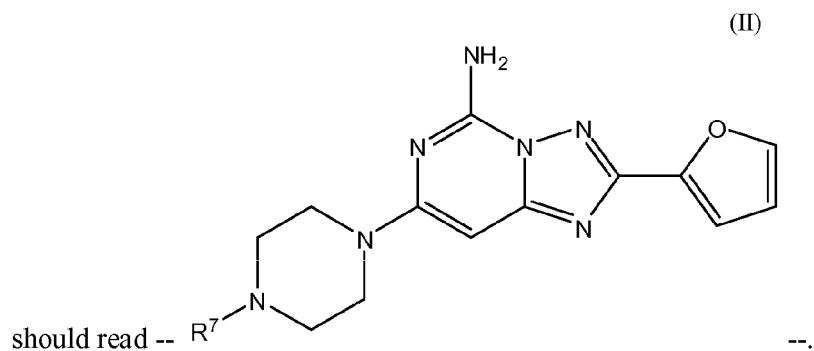 --.

COLUMN 54:

Line 21, "mula" should read --mulae--;
Line 38-46,

Formula (II) " 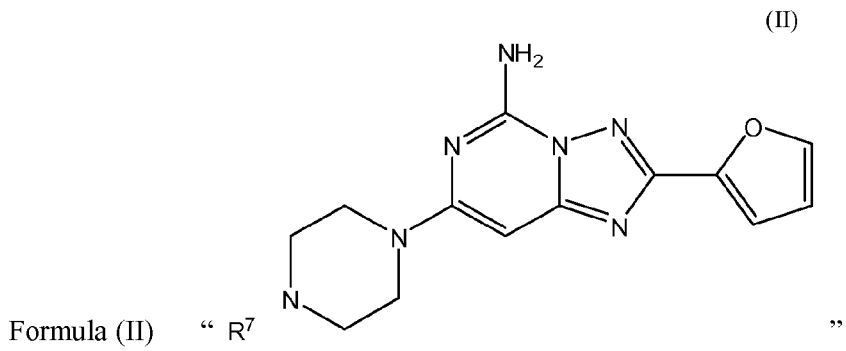 "

should read -- 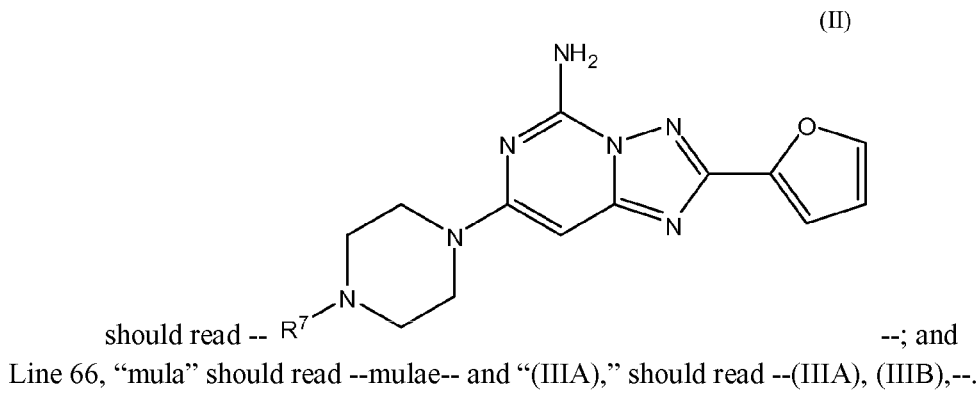 --; and
Line 66, "mula" should read --mulae-- and "(IIIA)," should read --(IIIA), (IIIB),--.

COLUMN 57:

Line 60, "activity," should read --activity;--.

COLUMN 58:
Line 12-20,
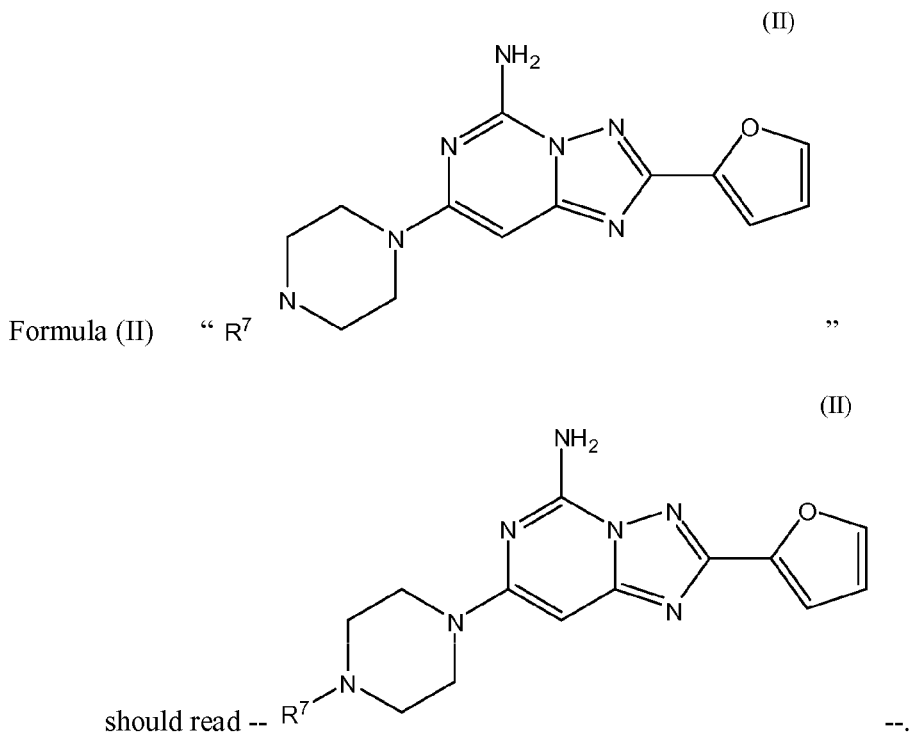
COLUMN 59:
Line 18, "formula" should read --formulae--.
COLUMN 60:
Line 66, "formula" should read --formulae--.
COLUMN 61:
Line 44, "formula" should read --formulae--.
COLUMN 62:
Line 51, "2003011864" should read --2003/011864--.
COLUMN 63:
Line 9, "it is," should read --they are,--; and
Line 67, "and the like;" should be deleted.

COLUMN 64:

Line 33, "dorsolumbar pain," (dupl.) should be deleted; and
    Line 44, "dorsolumbar pain," (dupl.) should be deleted.

COLUMN 65:

Line 4, "administrating" should read --administering--; and
    Line 23, "is," should read --is;--.

COLUMN 68:

Line 54, "a" should be deleted.

COLUMN 69:

Line 56, "a" should be deleted.

COLUMN 72:

Line 55, "(MB)" should read --(IIIB)--.